United States Patent
Teesalu et al.

(10) Patent No.: US 12,023,389 B2
(45) Date of Patent: Jul. 2, 2024

(54) COMPOSITIONS THAT TARGET TUMOR-ASSOCIATED MACROPHAGES AND METHODS OF USE THEREFOR

(71) Applicant: Sanford Burnham Prebys Medical Discovery Institute, La Jolla, CA (US)

(72) Inventors: Tambet Teesalu, Santa Barbara, CA (US); Pablo Scodeller, Tartu (EE); Erkki Ruoslahti, Rancho Santa Fe, CA (US)

(73) Assignee: Sanford Burnham Prebys Medical Discovery Institute, La Jolla, CA (US)

( * ) Notice: Subject to any disclaimer, the term of this patent is extended or adjusted under 35 U.S.C. 154(b) by 0 days.

(21) Appl. No.: 18/164,612

(22) Filed: Feb. 5, 2023

(65) Prior Publication Data

US 2024/0131201 A1    Apr. 25, 2024

Related U.S. Application Data

(63) Continuation of application No. 16/650,266, filed as application No. PCT/US2018/053550 on Sep. 28, 2018, now Pat. No. 11,571,484.

(60) Provisional application No. 62/565,356, filed on Sep. 29, 2017.

(51) Int. Cl.
  *A61K 49/00*  (2006.01)
  *C07K 7/06*  (2006.01)
  *A61K 38/00*  (2006.01)

(52) U.S. Cl.
  CPC ...... *A61K 49/0093* (2013.01); *A61K 49/0041* (2013.01); *A61K 49/0056* (2013.01); *C07K 7/06* (2013.01); *A61K 38/00* (2013.01)

(58) Field of Classification Search
  CPC ............ A61K 49/0093; A61K 49/0041; A61K 49/0056; A61K 38/00; C07K 7/06
  See application file for complete search history.

(56) References Cited

U.S. PATENT DOCUMENTS

| | | |
|---|---|---|
| 2011/0214199 A1 | 9/2011 | Coffin |
| 2011/0311616 A1 | 12/2011 | Smith et al. |
| 2016/0101150 A1 | 4/2016 | Jaynes et al. |
| 2017/0128596 A1 | 5/2017 | Multhoff et al. |

FOREIGN PATENT DOCUMENTS

| | | |
|---|---|---|
| WO | WO-0122920 A2 | 4/2001 |
| WO | WO-2017158436 A1 | 9/2017 |
| WO | WO-2019067984 A2 | 4/2019 |

OTHER PUBLICATIONS

Allen et al. The Cambridge Crystallographic Data Centre: computer-based search, retrieval, analysis and display of information Acta Cryst B35:2331-2339 (1979).
Azad et al. γ-Tilmanocept, a New Radiopharmaceutical Tracer for Cancer Sentinel Lymph Nodes, Binds to the Mannose Receptor (CD206). J. Immunol. 195:2019-2029 (2015).
Baer et al. Suppression of microRNA activity amplifies IFN-γ-induced macrophage activation and promotes anti-tumour immunity. Nat. Cell Biol. 18:790-802 (2016).
Blouw et al. The hypoxic response of tumors is dependent on their microenvironment. Cancer Cell 4:133-146 (2003).
Blykers et al. PET Imaging of Macrophage Mannose Receptor-Expressing Macrophages in Tumor Stroma Using 18F-Radiolabeled Camelid Single-Domain Antibody Fragments. J. Nucl. Med. 56:1265-71 (2015).
Cieslewicz et al. Targeted delivery of proapoptotic peptides to tumor-associated macrophages improves survival. PNAS USA 110(40):15919-15924 (2013).
De Palma et al. Cancer: Macrophages limit chemotherapy. Nature 472:303-304 (2011).
De Palma et al. Tumor-targeted interferon-alpha delivery by Tie2-expressing monocytes inhibits tumor growth and metastasis. Cancer Cell 14:299-311 (2008).
Estiarte et al. Peptidomimetics for Drug Design, in Burger's Medicinal Chemistry and Drug Discovery vol. 1 (ed. M. E. Wolff; John Wiley & Sons 1995) pp. 803-861.
Fernandes et al. Glutaredoxins: glutathione-dependent redox enzymes with functions far beyond a simple thioredoxin backup system. Antioxid. Redox Signal. 6:63-74 (2004).
Fogal et al. Mitochondrial/Cell-Surface Protein p32/gC1qR as a Molecular Target in Tumor Cells and Tumor Stroma. Cancer Res. 68:7210-7218 (2008).
Gautier et al. Gene-expression profiles and transcriptional regulatory pathways that underlie the identity and diversity of mouse tissue macrophages. Nat. Immunol. 13:1118-28 (2012).
Geijtenbeek et al. Identification of DC-SIGN, a novel dendritic cell-specific ICAM-3 receptor that supports primary immune responses. Cell 100:575-585 (2000).
Hambardzumyan et al. The role of microglia and macrophages in glioma maintenance and progression. Nat. Neurosci. 19:20-27 (2015).
Hughes et al. Perivascular M2 macrophages stimulate tumor relapse after chemotherapy. Cancer Res. 75:3479-3491 (2015).
Jameson et al. Expression of DC-SIGN by dendritic cells of intestinal and genital mucosae in humans and rhesus macaques. J. Virol. 76:1866-75 (2002).
Khramtsov et al. Janus-Faced Tumor Microenvironment and Redox. Antioxid. Redox Signal. 10:723-729 (2014).
Laakkonen et al. A tumor-homing peptide with a targeting specificity related to lymphatic vessels. Nat Personalized nanomedicine. Clinical Cancer Research 18:4889. Med. 8:751-5 (2002).
Laakkonen et al. Antitumor activity of a homing peptide that targets tumor lymphatics and tumor cells. PNAS USA 101:9381-9386 (2004).
Lammers et al. Personalized nanomedicine. Clinical Cancer Research 18:4889-4894 (2012).
Lewis et al. The Multifaceted Role of Perivascular Macrophages in Tumors. Cancer Cell 30:18-25 (2016).

(Continued)

*Primary Examiner* — Robert S Cabral
(74) *Attorney, Agent, or Firm* — PROCOPIO, CORY, HARGREAVES & SAVITCH LLP

(57) ABSTRACT

Described herein are peptides, compositions, and methods for diagnosing, detecting, imaging, monitoring, preventing, treating, or ameliorating diseases or disorders including cancer, inflammatory disorder, and autoimmune disease.

19 Claims, 19 Drawing Sheets

Specification includes a Sequence Listing.

(56) References Cited

OTHER PUBLICATIONS

Ludtke et al. In vivo selection and validation of liver-specific ligands using a new T7 phage peptide display system. Drug Deliv. 14:357-69 (2007).
Madsen et al. M2-like macrophages are responsible for collagen degradation through a mannose receptor-mediated pathway. J. Cell Biol. 202:951-966 (2013).
Magnusson et al. Extremely rapid endocytosis mediated by the mannose receptor of sinusoidal endothelial rat liver cells. Biochem. J. 257:651-656 (1989).
Mann et al. A peptide for targeted, systemic delivery of imaging and therapeutic compounds into acute brain injuries. Nat. Commun. 7:11980 (2016).
Martello et al. A microRNA targeting dicer for metastasis control. Cell 141:1195-1207 (2010).
Martinez-Pomares et al. Binding properties of the mannose receptor. Immunobiology 204:527-535 (2001).
Martinez-Pomares et al. Carbohydrate-independent recognition of collagens by the macrophage mannose receptor. Eur. J. Immunol. 36:1074-1082 (2006).
Martinez-Pomares. The mannose receptor. J. Leukoc. Biol. 92:1177-86 (2012).
Mazzieri et al. Targeting the ANG2/TIE2 Axis Inhibits Tumor Growth and Metastasis by Impairing Angiogenesis and Disabling Rebounds of Proangiogenic Myeloid Cells. Cancer Cell 19:512-526 (2011).
Movahedi et al. Nanobody-based targeting of the macrophage mannose receptor for effective in vivo imaging of tumor-associated macrophages. Cancer Res. 72:4165-4177 (2012).
Nagy. Kinetics and mechanisms of thiol-disulfide exchange covering direct substitution and thiol oxidation-mediated pathways. Antioxid. Redox Signal. 18:1623-41 (2013).
Napper et al. Collagen binding by the mannose receptor mediated through the fibronectin type II domain. Biochem. J. 395:579-86 (2006).
Noy et al. Tumor-Associated Macrophages: From Mechanisms to Therapy. Immunity 41:49-61 (2014).
Paasonen et al. New p32/gC1q12 Ligands for Targeted Tumor Drug Delivery. ChemBioChem 17:570-575 (2016).
PCT/US2018/053550 International Search Report and Written Opinion dated Dec. 26, 2018.
Pollard. Tumour-educated macrophages promote tumour progression and metastasis. Nat. Rev. Cancer 4:71-78 (2004).
Rusinko et al. Using CONCORD to construct a large database of three-dimensional coordinates from connection tables, J. Chem. Inf. Comput. Sci. 29:251 (1989).
Scodeller et al. Precision Targeting of Tumor Macrophages with a CD206 Binding Peptide. Sci Rep 7(1):14655 (2017).
Seo et al. (64)Cu-Labeled LyP-1-Dendrimer for PET-CT Imaging of Atherosclerotic Plaque. Bioconjug. Chem. 25:231-239 (2014).
Sharma et al. Depletion Of Tumor-Associated Macrophages With Clodronate Loaded PLGA Nanoparticles. Nano Life 3(4):1343005 (2013).
Sharma et al. Tumor-Penetrating Nanosystem Strongly Suppresses Breast Tumor Growth. Nano Lett. 17(3):1356-1364 (2017).
Shen et al. Tasquinimod modulates suppressive myeloid cells and enhances cancer immunotherapies in murine models. Cancer Immunol Res. 3:136-48 (2015).
Simon-Gracia et al. iRGD peptide conjugation potentiates intraperitoneal tumor delivery of paclitaxel with polymersomes. Biomaterials 104:247-257 (2016).
Squadrito et al. DICERing macrophages for reprogramming TAMs. Cell Cycle 15(23):3149-3150 (2016).
Uchida et al. Protein cage nanoparticles bearing the LyP-1 peptide for enhanced imaging of macrophage-rich vascular lesions. ACS Nano 5:2493-502 (2011).
Williams et al. Tumor-associated macrophages: unwitting accomplices in breast cancer malignancy. NPJ Breast Cancer 2:15025 (2016).
Xin et al. Anti-glioblastoma efficacy and safety of paclitaxel-loading Angiopep-conjugated dual targeting PEG-PCL nanoparticles. Biomaterials 33:8167-8176 (2012).
Yonemura et al. Inhibition of peritoneal dissemination in human gastric cancer by M MP-7-specific antisense oligonucleotide. J Exp Clin Cancer Res 20:205-212 (2001).
Zhang et al. Imaging tumor-induced sentinel lymph node lymphangiogenesis with LyP-1 peptide. Amino Acids 42:2343-51 (2012).
Zhou et al. Periostin secreted by glioblastoma stem cells recruits M2 tumour-associated macrophages and promotes malignant growth. Nat. Cell Biol. 17:170-182 (2015).
Anonymous. GME_12252—Uncharacterized protein—*Halomonas* sp. TD01—GME_12252 gene & protein. (Sep. 21, 2011) Retrieved from the Internet: URL:https://www.uniprot.org/uniprot/F7SPM6 [retrieved on Mar. 26, 2021].
Asciutto et al. Phage-Display-Derived Peptide Binds to Human CD206 and Modeling Reveals a New Binding Site on the Receptor. J Phys Chem B. 123(9): 1973-1982 (2019).
Ngambenjawong et al. Synthesis and evaluation of multivalent M2pep peptides for targeting alternatively activated M2 macrophages. J Control Release 224:103-111 (2016).

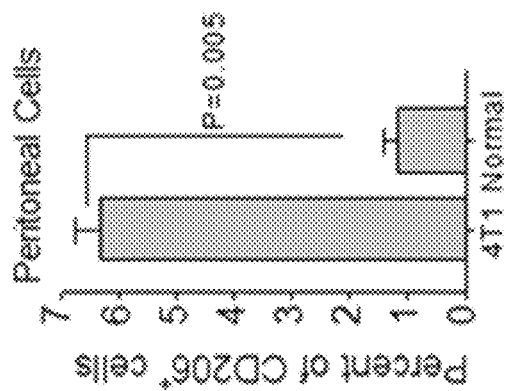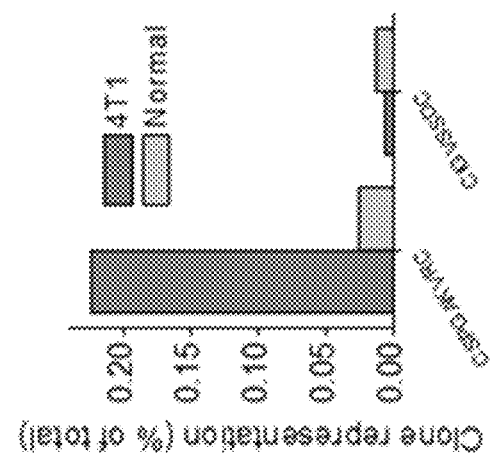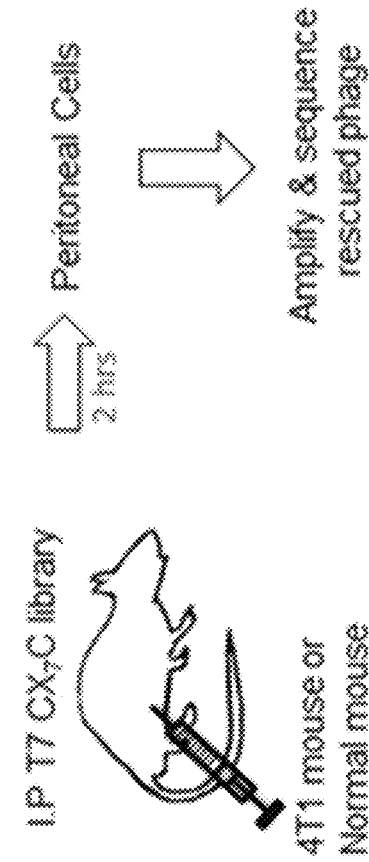
FIG. 1A FIG. 1B FIG. 1C FIG. 1D

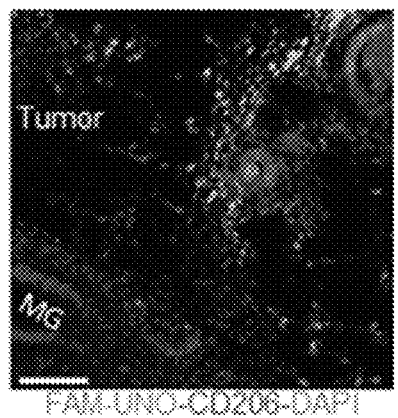 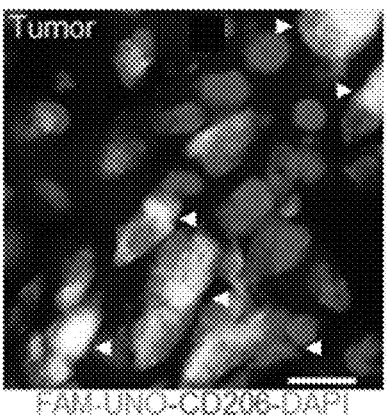 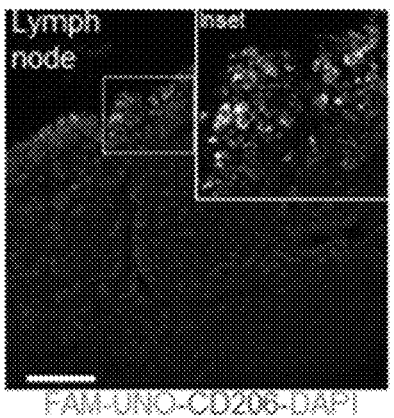
FIG. 2A  FIG. 2B  FIG. 2C
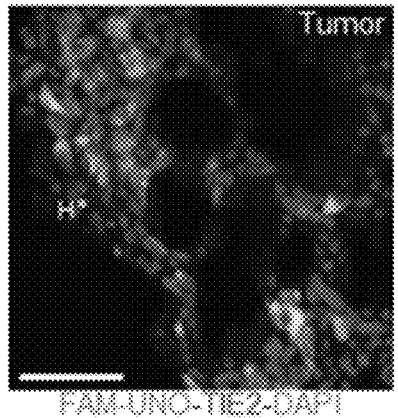 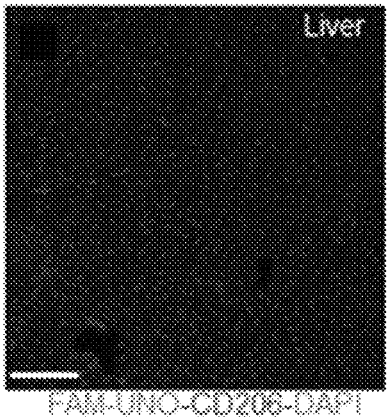 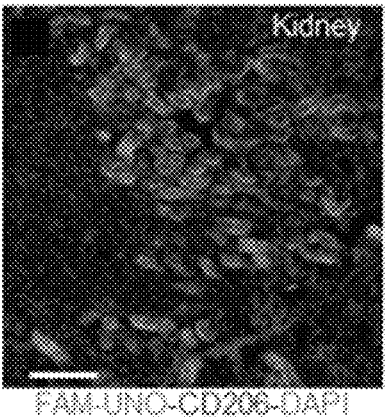
FIG. 2D  FIG. 2E  FIG. 2F
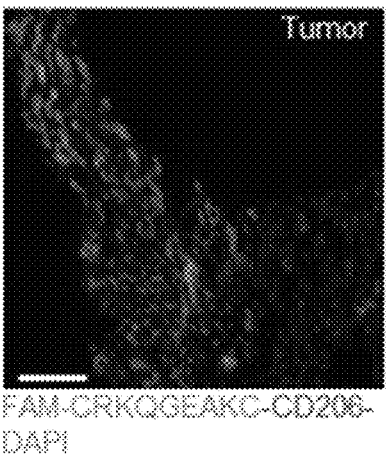 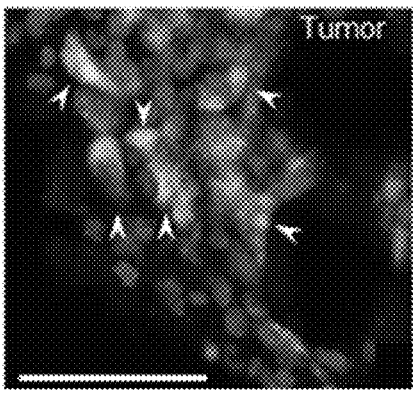 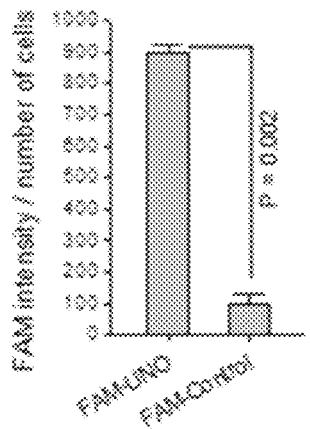
FIG. 2G  FIG. 2H  FIG. 2I

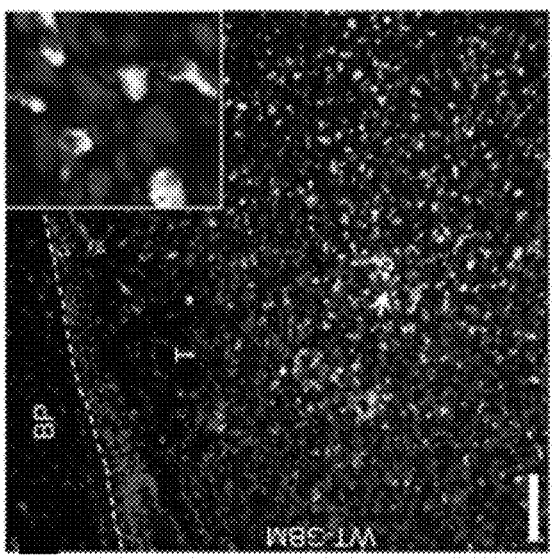
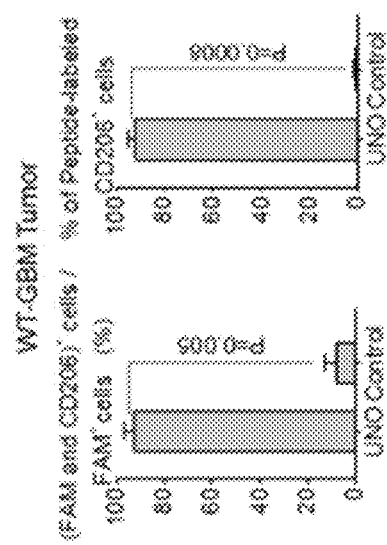
FIG. 3A
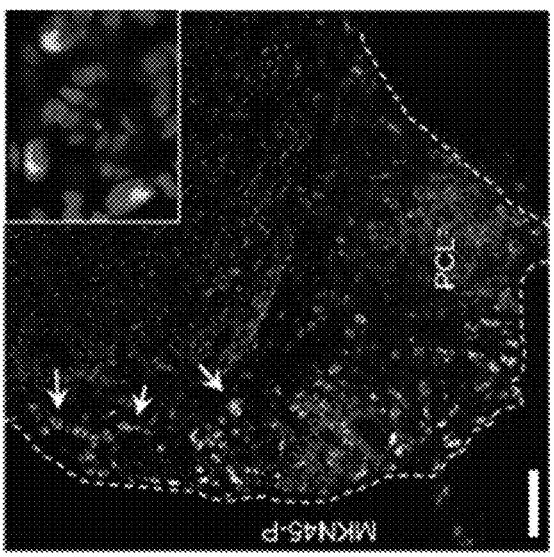
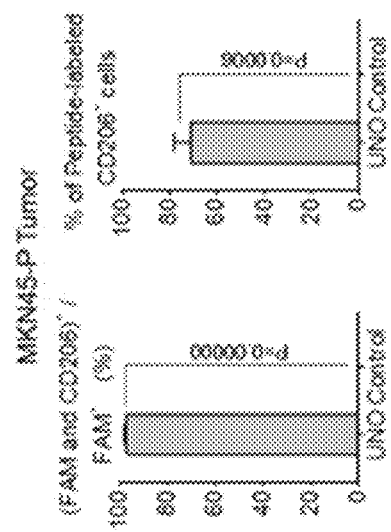
FIG. 3B
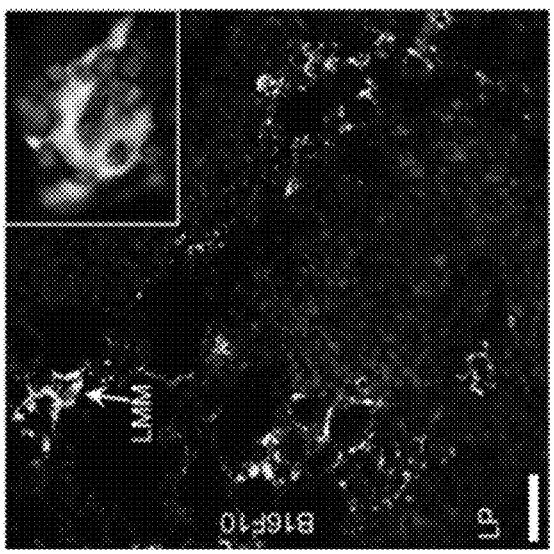
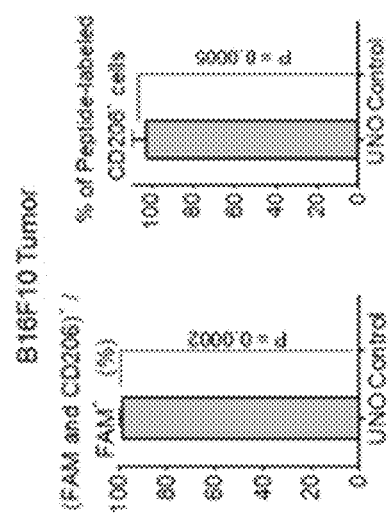
FIG. 3C

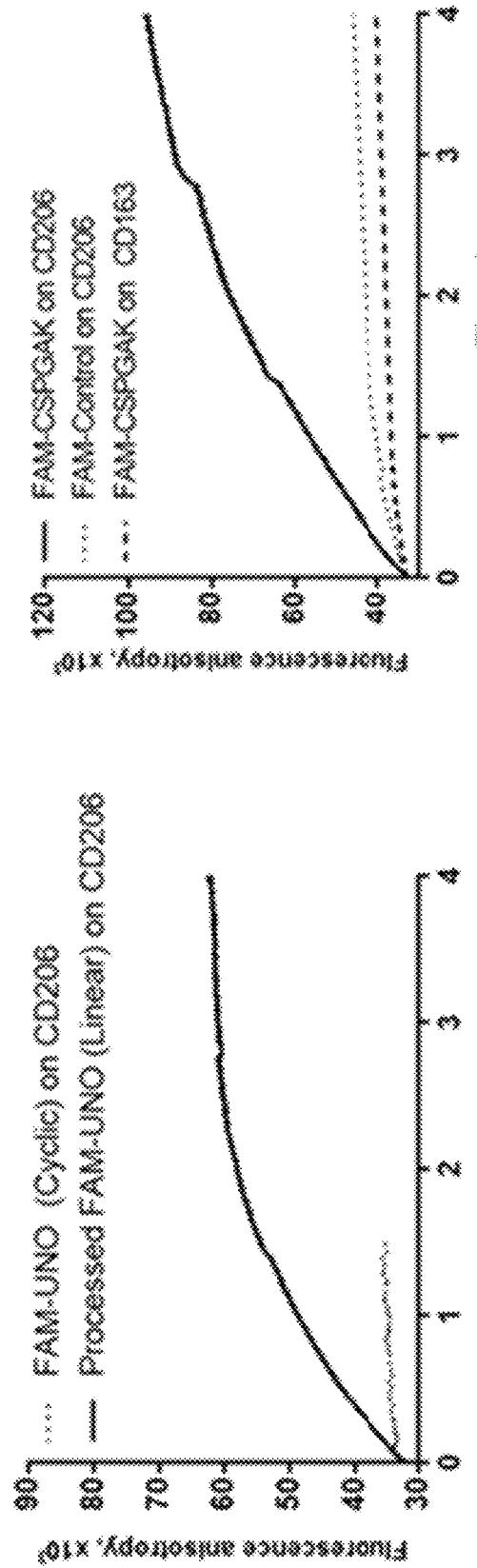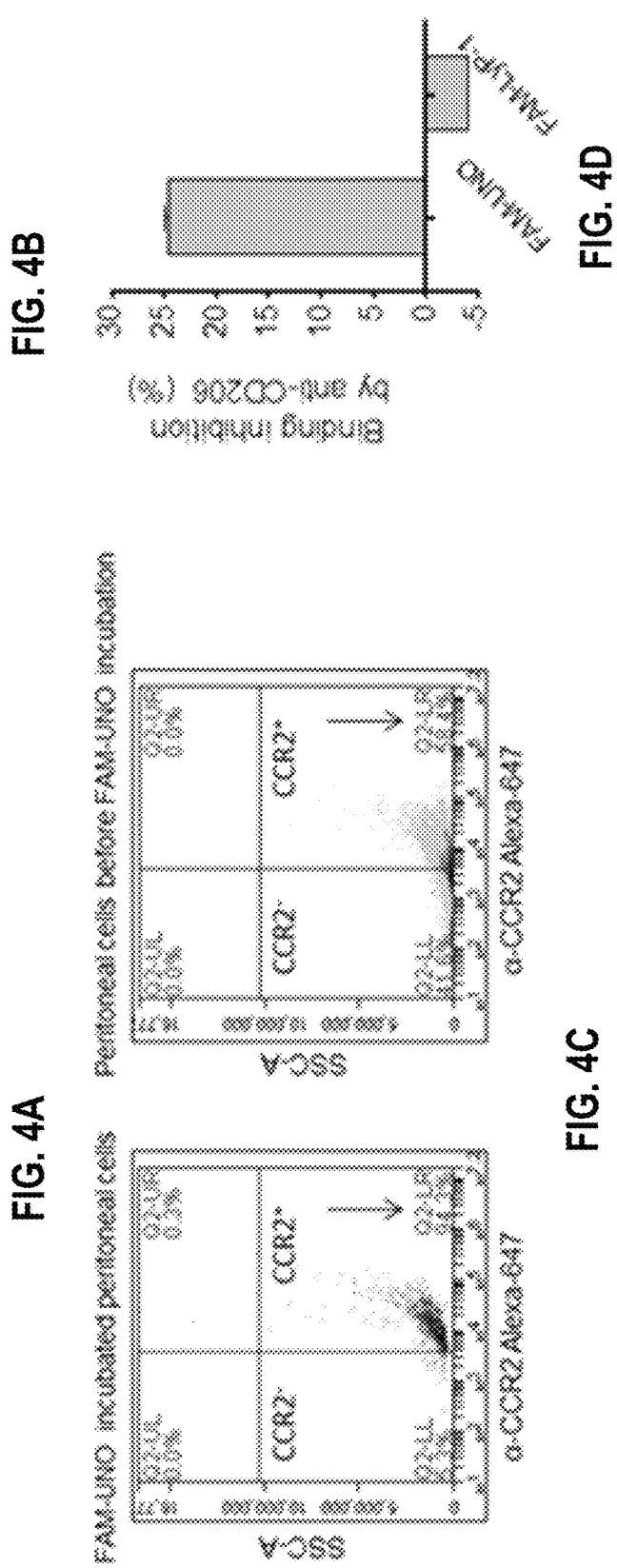
FIG. 4A  FIG. 4B  FIG. 4C  FIG. 4D

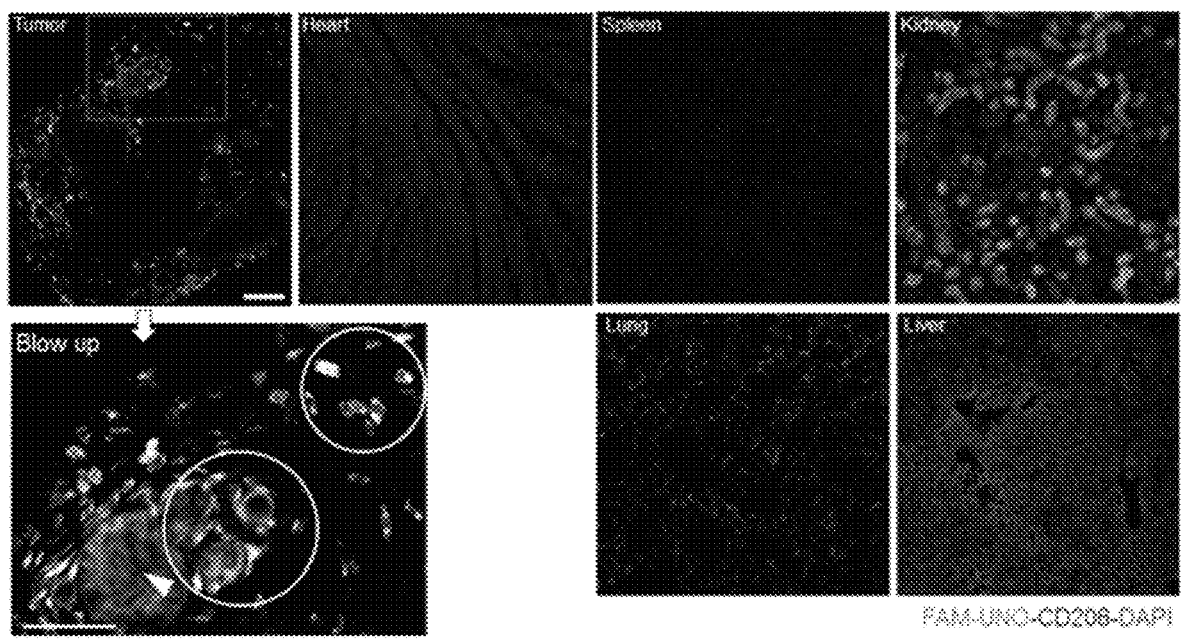
FIG. 11A
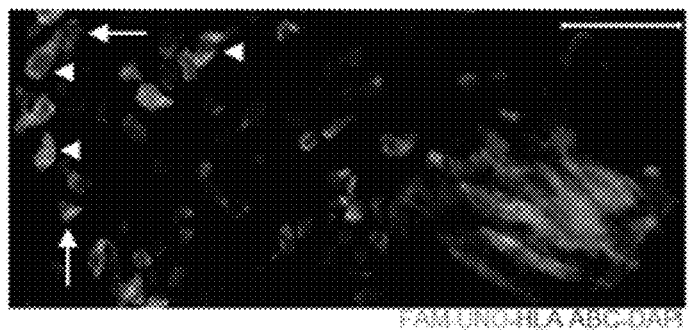
FIG. 11B
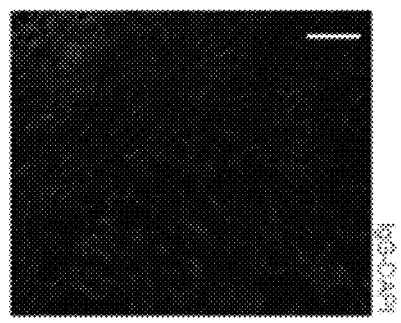
FIG. 11C
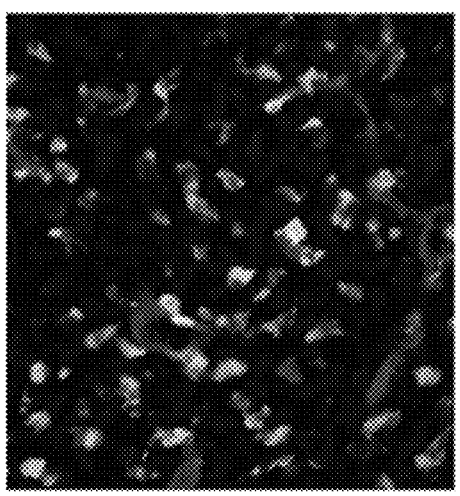
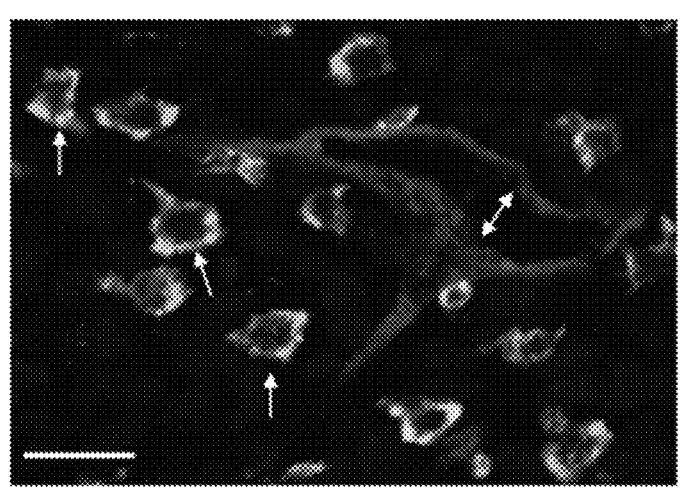
FIG. 12

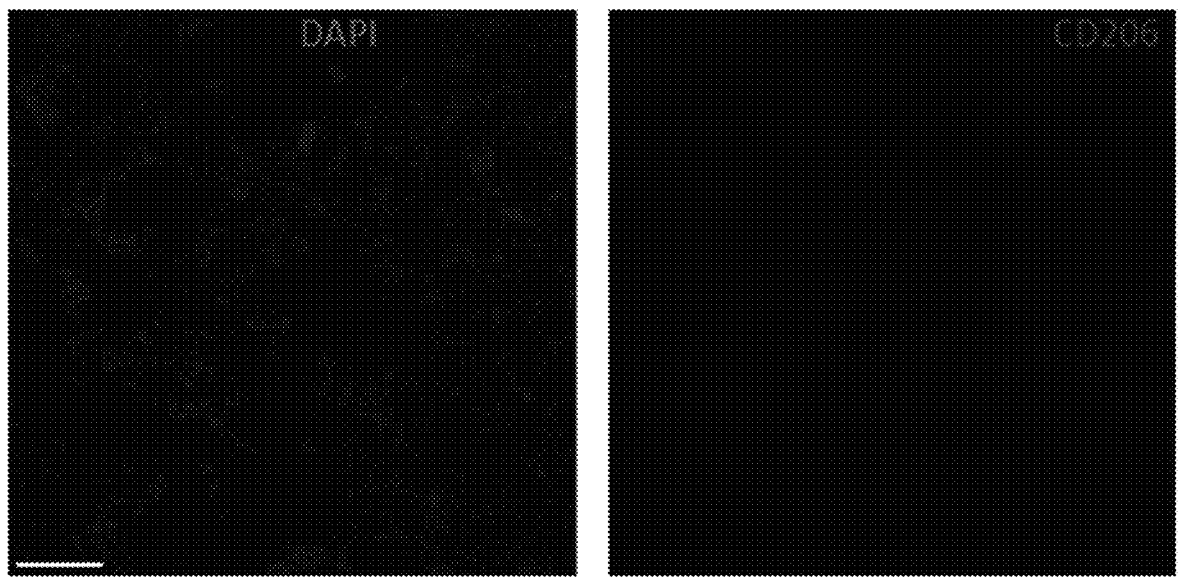

FIG. 26A

| | | | | | |
|---|---|---|---|---|---|
| Total unique peptides: | 8727 | 21-CSVGRLK | 131 | 43-CDALAPNSC | 93 |
| Sum total peptides: | 97659 | 22-CHQDF | 128 | 44-CIDGRTDLC | 92 |
| 1- CRTLRSKAC | 775 | 23-CSFDEANPC | 124 | 45-CMNVESSPC | 91 |
| 2- CRRTRQRSC | 500 | 24-CRNRA | 123 | 46-CREKNSQRC | 91 |
| 3-CIGNK | 420 | 25-CVSDRKVAC | 123 | 47-CLVRPERKC | 90 |
| 4-CVLNESGDC | 216 | 26-CKRGRFAKL | 120 | 48-CRKRMNRTC | 90 |
| 5-CRDKRGSKC | 194 | 27-CAQPNSR | 115 | 49-CVDITSPDC | 89 |
| 6-CVGRKVRGC | 193 | 28-CRPTRRVSC | 114 | 50-CSYEKEPVC | 86 |
| 7-CKRPNENVC | 183 | 29-CRNGLNKRC | 113 | ... | |
| 8-CNRRTKIGC | 182 | 30-CGFRSD | 112 | 2140-CSPGAKVRC | 10 |
| 9-CSPKMRATC | 180 | 31-CRKTVGPRC | 112 | | |
| 10-CKRTRRREC | 176 | 32-CEVMQRKRC | 107 | | |
| 11-CLSSITPEC | 169 | 33-CVASVKBKC | 106 | | |
| 12-CVDQDPL | 163 | 34-CDANQ | 106 | | |
| 13-CRGTRSNRC | 157 | 35-CRRTAIKKC | 106 | | |
| 14-CGPCQEGLC | 153 | 36-CDSRSRKBC | 105 | | |
| 15-CMTLRSRKC | 147 | 37-CLSKRTPRC | 105 | | |
| 16-CSTKTSLKC | 146 | 38-CVDSEATDC | 105 | | |
| 17-CGDEA | 146 | 39-CPRTAKVLC | 105 | | |
| 18-CTTSTGADC | 141 | 40-CQSRSPRNC | 101 | | |
| 19-CSTLKRRVC | 136 | 41-CNKNGTAPC | 101 | | |
| 20-CRGVAKVRC | 133 | 42-CTDRHSTNC | 94 | | |

FIG. 26B under CA152327, CA188883 and CA030199 from the National Cancer Institute (NCI) of the National Institutes of Health (NIH). The government has certain rights in the invention.
COMPOSITIONS THAT TARGET TUMOR-ASSOCIATED MACROPHAGES AND METHODS OF USE THEREFOR

CROSS-REFERENCE TO RELATED APPLICATIONS

This application claims the benefit of U.S. Provisional Patent Application No. 62/565,356 filed on Sep. 29, 2017. Priority is claimed pursuant to 35 U.S.C. § 119. The above noted patent application is incorporated by reference as if set forth fully herein.

STATEMENT AS TO FEDERALLY SPONSORED RESEARCH

This invention was made with government support under CA152327, CA188883 and CA030199 from the National Cancer Institute (NCI) of the National Institutes of Health (NIH). The government has certain rights in the invention.

SEQUENCE LISTING

The instant application contains a Sequence Listing which has been submitted electronically in ASCII format and is hereby incorporated by reference in its entirety. Said ASCII copy, created on Sep. 14, 2018, is named 42256-741-601-seqlist_ST25.txt and is 15,185 bytes in size.

INCORPORATION BY REFERENCE

All publications, patents, and patent applications mentioned in this specification are herein incorporated by reference to the same extent as if each individual publication, patent, or patent application was specifically and individually indicated to be incorporated by reference, and as if set forth in their entireties.

BACKGROUND OF THE INVENTION

Tumor-associated macrophages displaying a M2-like phenotype (M2 TAMs) play major roles in progression of solid tumors, including epithelial and mesenchymal tumors, glia-derived tumors, and melanoma. M2-like TAMs promote tumor growth and progression by stimulating tumor cell proliferation and by secreting factors that promote angiogenesis, such as VEGF-A6. M2 TAMs also induce transient openings in tumor neovessels that allow malignant cells to enter the bloodstream, promoting metastatic dissemination of solid tumors. M2-like TAMs increase in number after chemotherapy and contribute to tumor relapse. They also limit the efficacy of chemotherapies and support immunosuppressive microenvironment in tumors. Therefore, there remains a need for mechanisms for targeting M2 TAMs such as for treatment or diagnostic imaging purposes.

SUMMARY OF THE INVENTION

Provided herein, in some embodiments, are isolated peptides or peptidomimetics comprising the amino acid sequence CSPGAK (SEQ ID NO: 6). In some embodiments, the isolated peptides or peptidomimetics comprise the amino acid sequence CSPGAKVRC (SEQ ID NO: 1). In some embodiments, the peptides or peptidomimetics are conformationally constrained. In some embodiments, the peptides or peptidomimetics are cyclic. In some embodiments, the peptides or peptidomimetics are linear. In some embodiments, the peptides are modified peptides. In some embodiments, the peptides are methylated peptides. In some embodiments, the peptides or peptidomimetics comprise a methylated amino acid segment. In some embodiments, the peptides or peptidomimetics are N- or C-methylated in at least one position. In some embodiments, the peptides or peptidomimetics have a length of no more than 100 amino acid residues. In some embodiments, the peptides or peptidomimetics have a length of no more than 50 amino acid residues. In some embodiments, the peptides or peptidomimetics have a length of no more than 20 amino acid residues. In some embodiments, the peptides or peptidomimetics have a length of no more than 15 amino acid residues. In some embodiments, the peptides or peptidomimetics have a length of no more than 10 amino acid residues.

Provided herein, in some embodiments, are compositions comprising the isolated peptides or peptidomimetics of any of the preceding embodiments. In some embodiments, the compositions selectively home to tumor tissue. In some embodiments, the compositions selectively home to MRC1-expressing tumor-associated macrophages (MEMs). In some embodiments, the compositions further comprise a detectable agent. In some embodiments, the detectable agent is a fluorescent molecule or a radionuclide. In some embodiments, the detectable agent is linked to the isolated peptide or peptidomimetic. In some embodiments, the detectable agent is Feridex, a tantalum compound, iodine, radioactive iodine, an organic iodo acid, iron oxide, gadolinium, an enzyme, biotin, a metal, barium sulfate, diatrizoic acid sodium salt dehydrate, Lissamine Rhodamine PE, Rhodamine, a radioisotope, a ferromagnetic compound, a paramagnetic compound, a diamagnetic compound, indium-111, technetium-99, carbon-11, carbon-13, or any combination thereof. In some embodiments, the compositions further comprise a nanoparticle. In some embodiments, the nanoparticle is a polymersome. In some embodiments, the polymersome is a polyethylene glycol-polycaprolactone polymersome. In some embodiments, the polyethylene glycol-polycaprolactone polymersome has a diameter of less than 1000 nanometers. In some embodiments, the polyethylene glycol-polycaprolactone polymersome has a diameter of less than 500 nanometers. In some embodiments, the polyethylene glycol-polycaprolactone polymersome has a diameter of about 120 nanometers. In some embodiments, the isolated peptide or peptidomimetic is coated onto the polyethylene glycol-polycaprolactone polymersome. In some embodiments, the polyethylene glycol-polycaprolactone polymersome is loaded with a therapeutic agent. In some embodiments, the compositions further comprise a therapeutic agent. In some embodiments, the therapeutic agent is linked to the isolated peptide or peptidomimetic. In some embodiments, the therapeutic agent is a therapeutic protein, a therapeutic compound, a therapeutic composition, a chemotherapeutic agent, a cancer chemotherapeutic agent, a radiopharmaceutical, a toxin, a cytotoxic agent, Abraxane, paclitaxel, taxol, imatinib, a virus, a nucleic acid molecule, an antibody, a small interfering RNA, a microRNA, a polypeptide, a peptide, an anti-angiogenic agent, a pro-angiogenic agent, an anti-inflammatory agent, a TGF-β inhibitor, a β-2 agonist, an endothelin (ET-1) receptor antagonist, interferon-a and tasquinimod, or any combination thereof.

Provided herein, in some embodiments, are methods for directing a moiety to a MRC1-expressing tumor associated macrophage in a subject, comprising administering to the subject a composition comprising the moiety linked to an isolated peptide or peptidomimetic comprising the amino acid sequence CSPGAK (SEQ ID NO: 6) or a peptidomimetic thereof. In some embodiments, the isolated peptide or peptidomimetic comprises the amino acid sequence CSPGAKVRC (SEQ ID NO: 1) or a peptidomimetic thereof. In some embodiments, the peptide or peptidomimetic is conformationally constrained. In some embodiments, the peptide or peptidomimetic is cyclic. In some embodiments, the peptide or peptidomimetic is linear. In some embodiments, the peptide is a modified peptide. In some embodiments, the peptide is a methylated peptide. In some embodiments, the peptide or peptidomimetic comprises a methylated amino acid segment. In some embodiments, the peptide or peptidomimetic is N- or C-methylated in at least one position. In some embodiments, the peptide or peptidomimetic the peptide or peptidomimetic thereof has a length of no more than 100 amino acid residues. In some embodiments, the peptide or peptidomimetic has a length of no more than 50 amino acid residues. In some embodiments, the peptide or peptidomimetic has a length of no more than 20 amino acid residues. In some embodiments, the peptide or peptidomimetic has a length of no more than 15 amino acid residues. In some embodiments, the peptide or peptidomimetic has a length of no more than 10 amino acid residues. In some embodiments, the moiety comprises a detectable agent. In some embodiments, the detectable agent is a fluorescent molecule or a radionuclide. In some embodiments, the detectable agent is linked to the isolated peptide or peptidomimetic. In some embodiments, the detectable agent is Feridex, a tantalum compound, iodine, radioactive iodine, an organic iodo acid, iron oxide, gadolinium, an enzyme, biotin, a metal, barium sulfate, diatrizoic acid sodium salt dehydrate, Lissamine Rhodamine PE, Rhodamine, a radioisotope, a ferromagnetic compound, a paramagnetic compound, a diamagnetic compound, indium-111, technetium-99, carbon-11, carbon-13, or any combination thereof. In some embodiments, the moiety further comprises a nanoparticle. In some embodiments, the nanoparticle is a polymersome. In some embodiments, the polymersome is a polyethylene glycol-polycaprolactone polymersome. In some embodiments, the polyethylene glycol-polycaprolactone polymersome has a diameter of less than 1000 nanometers. In some embodiments, the polyethylene glycol-polycaprolactone polymersome has a diameter of less than 500 nanometers. In some embodiments, the polyethylene glycol-polycaprolactone polymersome has a diameter of about 120 nanometers. In some embodiments, the isolated peptide or peptidomimetic is coated onto the polyethylene glycol-polycaprolactone polymersome. In some embodiments, the polyethylene glycol-polycaprolactone polymersome is loaded with a therapeutic agent. In some embodiments, the moiety comprises a therapeutic agent. In some embodiments, the therapeutic agent is linked to the isolated peptide or peptidomimetic. In some embodiments, the therapeutic agent is a therapeutic protein, a therapeutic compound, a therapeutic composition, a chemotherapeutic agent, a cancer chemotherapeutic agent, a radiopharmaceutical, a toxin, a cytotoxic agent, Abraxane, paclitaxel, taxol, imatinib, a virus, a nucleic acid molecule, an antibody, a small interfering RNA, a microRNA, a polypeptide, a peptide, an anti-angiogenic agent, a pro-angiogenic agent, an anti-inflammatory agent, a TGF-β inhibitor, a β-2 agonist, an endothelin (ET-1) receptor antagonist, interferon-a and tasquinimod, or any combination thereof. In some embodiments, the composition is administered intravenously, intraperitoneally, intramuscularly, subcutaneously, intracavitarally, or transdermally.

Provided herein, in some embodiments, are methods of diagnosing a subject with a disease or disorder, comprising administering to the subject a composition comprising a detectable agent linked to an isolated peptide or peptidomimetic comprising the amino acid sequence CSPGAK (SEQ ID NO: 6) or a peptidomimetic thereof. In some embodiments, the isolated peptide or peptidomimetic comprises the amino acid sequence CSPGAKVRC (SEQ ID NO: 1) or a peptidomimetic thereof. In some embodiments, the isolated peptide or peptidomimetic is conformationally constrained. In some embodiments, the isolated peptide or peptidomimetic is cyclic. In some embodiments, the isolated peptide or peptidomimetic is linear. In some embodiments, the peptide is a modified peptide. In some embodiments, the peptide is a methylated peptide. In some embodiments, the isolated peptide or peptidomimetic comprises a methylated amino acid segment. In some embodiments, the isolated peptide or peptidomimetic is N- or C-methylated in at least one position. In some embodiments, the isolated peptide or peptidomimetic has a length of no more than 100 amino acid residues. In some embodiments, the isolated peptide or peptidomimetic has a length of no more than 50 amino acid residues. In some embodiments, the isolated peptide or peptidomimetic has a length of no more than 20 amino acid residues. In some embodiments, the isolated peptide or peptidomimetic has a length of no more than 15 amino acid residues. In some embodiments, the isolated peptide or peptidomimetic has a length of no more than 10 amino acid residues. In some embodiments, the detectable agent is a fluorescent molecule or a radionuclide. In some embodiments, the detectable agent is linked to the isolated peptide or peptidomimetic. In some embodiments, the detectable agent is Feridex, a tantalum compound, iodine, radioactive iodine, an organic iodo acid, iron oxide, gadolinium, an enzyme, biotin, a metal, barium sulfate, diatrizoic acid sodium salt dehydrate, Lissamine Rhodamine PE, Rhodamine, a radioisotope, a ferromagnetic compound, a paramagnetic compound, a diamagnetic compound, indium-111, technetium-99, carbon-11, carbon-13, or any combination thereof. In some embodiments, the composition further comprises a nanoparticle. In some embodiments, the nanoparticle is a polymersome. In some embodiments, the polymersome is a polyethylene glycol-polycaprolactone polymersome. In some embodiments, the polyethylene glycol-polycaprolactone polymersome has a diameter of less than 1000 nanometers. In some embodiments, the polyethylene glycol-polycaprolactone polymersome has a diameter of less than 500 nanometers. In some embodiments, the polyethylene glycol-polycaprolactone polymersome has a diameter of about 120 nanometers. In some embodiments, the isolated peptide or peptidomimetic is coated onto the polyethylene glycol-polycaprolactone polymersome. In some embodiments, the disease or disorder is cancer, an inflammatory disorder, or an autoimmune disease. In some embodiments, the composition is administered intravenously, intraperitoneally, intramuscularly, subcutaneously, intracavitarally, or transdermally.

Provided herein, in some embodiments, are methods of treating a subject with a disease or disorder comprising administering to the subject a composition comprising a therapeutic agent linked to an isolated peptide or peptidomimetic comprising the amino acid sequence CSPGAK (SEQ ID NO: 6) or a peptidomimetic thereof. In some embodiments, the isolated peptide or peptidomimetic comprises the amino acid sequence CSPGAKVRC (SEQ ID NO: 1) or a peptidomimetic thereof. In some embodiments, the isolated peptide or peptidomimetic is conformationally constrained. In some embodiments, the isolated peptide or peptidomimetic is cyclic. In some embodiments, the isolated peptide or peptidomimetic is linear. In some embodiments, the isolated peptide is a modified peptide. In some embodiments, the isolated peptide is a methylated peptide. In some embodiments, the isolated peptide or peptidomimetic comprises a methylated amino acid segment. In some embodiments, the isolated peptide or peptidomimetic is N- or C-methylated in at least one position. In some embodiments, the isolated peptide or peptidomimetic has a length of no more than 100 amino acid residues. In some embodiments, the isolated peptide or peptidomimetic has a length of no more than 50 amino acid residues. In some embodiments, the isolated peptide or peptidomimetic has a length of no more than 20 amino acid residues. In some embodiments, the isolated peptide or peptidomimetic has a length of no more than 15 amino acid residues. In some embodiments, the isolated peptide or peptidomimetic has a length of no more than 10 amino acid residues. In some embodiments, the composition further comprises a nanoparticle. In some embodiments, the nanoparticle is a polymersome. In some embodiments, the polymersome is a polyethylene glycol-polycaprolactone polymersome. In some embodiments, the polyethylene glycol-polycaprolactone polymersome has a diameter of less than 1000 nanometers. In some embodiments, the polyethylene glycol-polycaprolactone polymersome has a diameter of less than 500 nanometers. In some embodiments, the polyethylene glycol-polycaprolactone polymersome has a diameter of about 120 nanometers. In some embodiments, the isolated peptide or peptidomimetic is coated onto the polyethylene glycol-polycaprolactone polymersome. In some embodiments, the polyethylene glycol-polycaprolactone polymersome is loaded with the therapeutic agent. In some embodiments, the therapeutic agent is a therapeutic protein, a therapeutic compound, a therapeutic composition, a chemotherapeutic agent, a cancer chemotherapeutic agent, a radiopharmaceutical, a toxin, a cytotoxic agent, Abraxane, paclitaxel, taxol, imatinib, a virus, a nucleic acid molecule, an antibody, a small interfering RNA, a microRNA, a polypeptide, a peptide, an anti-angiogenic agent, a pro-angiogenic agent, an anti-inflammatory agent, a TGF-β inhibitor, a β-2 agonist, an endothelin (ET-1) receptor antagonist, interferon-a and tasquinimod, or any combination thereof. In some embodiments, the disease or disorder is cancer, an inflammatory disorder, or an autoimmune disease. In some embodiments, the composition is administered intravenously, intraperitoneally, intramuscularly, subcutaneously, intracavitarally, or transdermally.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 shows the identification of CSPGAKVRC ("UNO"; SEQ ID NO: 1) in breast cancer mice. FIG. 1A illustrates the phage library screening method used to identify UNO. FIG. 1B shows the number of CD206+ cells in 4T1 mice compared to normal mice. FIG. 1C shows highly repeated sequences identified from the phage library screen. FIG. 1D shows a measure of the frequency of phage clones encoding UNO compared to a random control peptide in the mice.

FIG. 2 shows that FAM-UNO accumulates in CD206+, TIE2+ macrophages in breast tumors and lymph node. FAM-UNO accumulated in macrophages within tumors and lymph nodes positive for CD206 staining (FIG. 2A, FIG. 2B, FIG. 2C) and TIE2 (FIG. 2D, and FIG. 2H). FAM-UNO showed very low accumulation in the liver (FIG. 2E), but signal was seen in the kidneys (FIG. 2F). The control peptide did not give any signal in CD206+ macrophages or elsewhere in the tumor (FIG. 2G and FIG. 2I).

FIG. 3 shows fluorescence imaging of FAM-UNO accumulation in CD206+ macrophages in glioblastoma, gastric carcinoma, and melanoma. FIG. 3A shows FAM-UNO homing to glioblastoma (WT-GBM). FIG. 3B shows FAM-UNO homing to a peritoneal carcinomatosis lesion (PCL). FIG. 3C shows FAM-UNO homing to experimental melanoma metastases in the lungs.

FIG. 4 shows UNO specificity for CD206. FIG. 4A shows the change in fluorescence anisotropy of FAM-UNO (dotted line) and FAM-UNO in DTT (solid line) while incubating with mouse recombinant CD206. FIG. 4B shows the change in fluorescence anisotropy of FAM-CSPGAK (SEQ ID NO: 6) with mouse recombinant CD206 (solid line) or with CD163 (dotted line) and of FAM-CPMTDNE (control; SEQ ID NO: 7) with CD206 (dashed line). FIG. 4C shows FAM-UNO binding to CCR2+ macrophages. FIG. 4D shows FAM-UNO binding to peritoneal cells is inhibited by pre-incubating with anti-CD206 in comparison to FAM-LyP-1.

FIG. 6 shows that FAM-UNO can be used to image metastasis-draining lymph nodes.

FIG. 11 shows fluorescence imaging of FAM-UNO accumulation in MEMs in MCF-7 breast cancer. FIG. 11A shows the presence of FAM-UNO in MCF-7 tumors. FIG. 11B shows that FAM-UNO does not home to cancer cells. FIG. 11C shows that MCF-7 tumors are leaky.

FIG. 12 shows fluorescence imaging of FAM-UNO internalized by perivascular cells in WT-GBM tumor.

FIG. 23 shows fluorescence imaging of FAM-CSPGAK (SEQ ID NO: 6) accumulation in MEMs.

FIG. 26 shows that CSPGAKVRC (SEQ ID NO: 1) is not selected in phage library screening on cultured CD206⁻ mouse macrophages. FIG. 26A shows cultured RAW 267.4 mouse macrophages stained with rat anti-CD206 (red) and counterstained with DAPI (blue). FIG. 26B shows the top 50 hits and the rank for CSPGAKVRC (SEQ ID NO: 1) from a phage display screen using the CD206⁻ RAW 267.4 cells.

DETAILED DESCRIPTION OF THE INVENTION

Figure 5A:
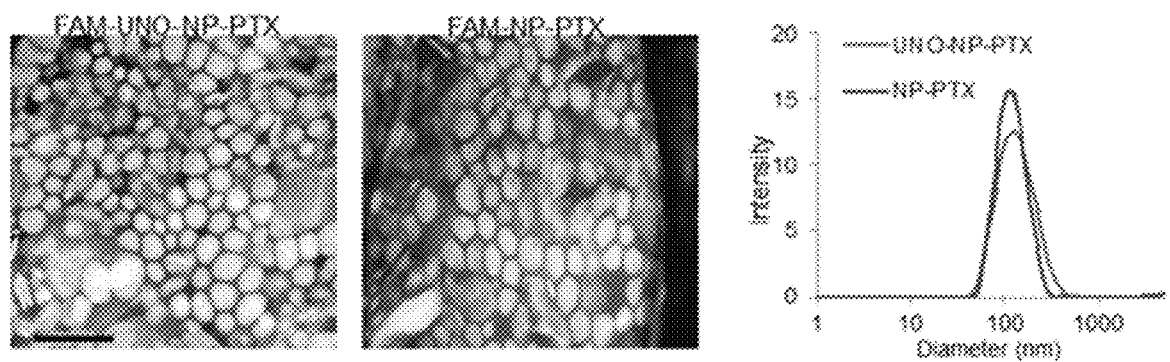
FIG. 5A shows characterization of FAM-UNO derivatized, paclitaxel loaded, polymeric vesicles ("FAM-UNO-NP-PTX") using transmission electron microscopy images and Dynamic Light Scattering profile.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Certain Definitions

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All references cited herein are incorporated by reference in their entirety as though fully set forth. Singleton et al., Dictionary of Microbiology and Molecular Biology 3rd ed., J. Wiley & Sons (New York, NY 2001); March, Advanced Organic Chemistry Reactions, Mechanisms and Structure 5th ed., J. Wiley & Sons (New York, NY 2001); and Sambrook and Russel, Molecular Cloning: A Laboratory Manual 3rd ed., Cold Spring Harbor Laboratory Press (Cold Spring Harbor, N Y 2001), provide one skilled in the art with a general guide to many of the terms used in the present application.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the given value. Where particular values are described in the application and claims, unless otherwise stated the term "about" should be assumed to mean an acceptable error range for the particular value.

When indicating the number of substituents, the term "one or more" refers to the range from one substituent to the highest possible number of substitution, e.g. replacement of one hydrogen up to replacement of all hydrogens by substituents.

The term "optional" or "optionally" denotes that a subsequently described event or circumstance can but need not occur, and that the description includes instances where the event or circumstance occurs and instances in which it does not.

The term "nucleic acid" as used herein generally refers to one or more nucleobases, nucleosides, or nucleotides. For example, a nucleic acid may include one or more nucleotides selected from adenosine (A), cytosine (C), guanine (G), thymine (T) and uracil (U), or variants thereof. A nucleotide generally includes a nucleoside and at least 1, 2, 3, 4, 5, 6, 7, 8, 9, 10, or more phosphate ($PO_3$) groups. A nucleotide can include a nucleobase, a five—carbon sugar (either ribose or deoxyribose), and one or more phosphate groups. Ribonucleotides include nucleotides in which the sugar is ribose. Deoxyribonucleotides include nucleotides in which the sugar is deoxyribose. A nucleotide can be a nucleoside monophosphate, nucleoside diphosphate, nucleoside triphosphate or a nucleoside polyphosphate.

As used herein, the terms "polypeptide", "protein" and "peptide" are used interchangeably and refer to a polymer of amino acid residues linked via peptide bonds and which may be composed of two or more polypeptide chains. The terms "polypeptide", "protein" and "peptide" refer to a polymer of at least two amino acid monomers joined together through amide bonds. An amino acid may be the L-optical isomer or the D-optical isomer. More specifically, the terms "polypeptide", "protein" and "peptide" refer to a molecule composed of two or more amino acids in a specific order; for example, the order as determined by the base sequence of nucleotides in the gene or RNA coding for the protein. Proteins are essential for the structure, function, and regulation of the body's cells, tissues, and organs, and each protein has unique functions. Examples are hormones, enzymes, antibodies, and any fragments thereof. In some cases, a protein can be a portion of the protein, for example, a domain, a subdomain, or a motif of the protein. In some cases, a protein can be a variant (or mutation) of the protein, wherein one or more amino acid residues are inserted into, deleted from, and/or substituted into the naturally occurring (or at least a known) amino acid sequence of the protein. A protein or a variant thereof can be naturally occurring or recombinant.

As used herein, the term "biological sample" means any biological material from which polynucleotides, polypeptides, biomarkers, and/or metabolites can be prepared and examined. Non-limiting examples encompasses whole blood, plasma, saliva, cheek swab, fecal specimen, urine specimen, cell mass, or any other bodily fluid or tissue.

The terms "administer," "administering", "administration," and the like, as used herein, refer to the methods that may be used to enable delivery of compounds or compositions to the desired site of biological action. These methods include, but are not limited to oral routes (p.o.), intraduodenal routes (i.d.), parenteral injection (including intravenous (i.v.), subcutaneous (s.c.), intraperitoneal (i.p.), intramuscular (i.m.), intravascular or infusion (inf.)), topical (top.) and rectal (p.r.) administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated; for example a reduction and/or alleviation of one or more signs, symptoms, or causes of a disease, or any other desired alteration of a biological system. For example, an "effective amount" for therapeutic uses can be an amount of an agent that provides a clinically significant decrease in one or more disease symptoms. An appropriate "effective" amount may be determined using techniques, such as a dose escalation study, in individual cases.

The term "subject" or "patient" encompasses mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human. The term "animal" as used herein comprises human beings and non-human animals. In one embodiment, a "non-human animal" is a mammal, for example a rodent such as rat or a mouse.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

The term "preventing" or "prevention" of a disease state denotes causing the clinical symptoms of the disease state not to develop in a subject that can be exposed to or predisposed to the disease state, but does not yet experience or display symptoms of the disease state.

The terms "pharmaceutical composition" and "pharmaceutical formulation" (or "formulation") are used interchangeably and denote a mixture or solution comprising a therapeutically effective amount of an active pharmaceutical ingredient together with one or more pharmaceutically acceptable excipients to be administered to a subject, e.g., a human in need thereof.

The term "pharmaceutical combination" as used herein, means a product that results from mixing or combining more than one active ingredient.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use. "Pharmaceutically acceptable" can refer a material, such as a carrier or diluent, which does not abrogate the biological activity or properties of the compound, and is relatively nontoxic, e.g., the material may be administered to an individual without causing undesirable biological effects or interacting in a deleterious manner with any of the components of the composition in which it is contained.

The terms "pharmaceutically acceptable excipient", "pharmaceutically acceptable carrier", "pharmaceutically acceptable vehicle" and "therapeutically inert excipient" can be used interchangeably and denote any pharmaceutically acceptable ingredient in a pharmaceutical composition having no therapeutic activity and being non-toxic to the subject administered, such as disintegrators, binders, fillers, solvents, buffers, tonicity agents, stabilizers, antioxidants, surfactants, carriers, diluents, excipients, preservatives or lubricants used in formulating pharmaceutical products The term "pharmaceutically acceptable salts" denotes salts which are not biologically or otherwise undesirable. Pharmaceutically acceptable salts include both acid and base addition salts. A "pharmaceutically acceptable salt" can refer to a formulation of a compound or agent that does not cause significant irritation to an organism to which it is administered and/or does not abrogate the biological activity and properties of the compound or agent.

The term "label," as used herein, refers to a detectable agent or compound, composition, or solid support, which can be conjugated directly or indirectly (e.g., via covalent or non-covalent means, alone or encapsulated) to a protein or peptide. The label may be detectable by itself (e.g., radioisotope labels, chemiluminescent dye, electrochemical labels, metal chelates, latex particles, or fluorescent labels) or, in the case of an enzymatic label, may catalyze chemical alteration of a substrate compound or composition which is detectable (e.g., enzymes such as horseradish peroxidase, alkaline phosphatase, and the like). The label employed in the current invention could be, but is not limited to alkaline phosphatase; glucose-6-phosphate dehydrogenase ("G6PDH"); horseradish peroxidase (HRP); chemiluminescent molecules such as isoluminol, fluorescent molecules such as fluorescein and rhodamine compounds; ribozymes; and dyes. The label may also be a specific binding molecule which itself may be detectable (e.g., biotin, avidin, streptavidin, digioxigenin, maltose, oligohistidine, e.g., hex-histidine, 2, 4-dinitrobenzene, phenylarsenate, ssDNA, dsDNA, and the like). The utilization of a label produces a signal that may be detected by means such as detection of electromagnetic radiation or direct visualization, and that can optionally be measured.

As used herein, the term "substantially the same amino acid sequence" includes an amino acid sequence that is similar, but not identical to, the naturally-occurring amino acid sequence. For example, an amino acid sequence, e.g., polypeptide, that has substantially the same amino acid sequence as a flagellin protein can have one or more modifications such as amino acid additions, deletions, or substitutions relative to the amino acid sequence of the naturally-occurring flagellin protein, provided that the modified polypeptide retains substantially at least one biological activity of flagellin such as immunoreactivity. The "percentage similarity" between two sequences is a function of the number of positions that contain matching residues or conservative residues shared by the two sequences divided by the number of compared positions times 100. In this regard, conservative residues in a sequence is a residue that is physically or functionally similar to the corresponding reference residue, e.g., that has a similar size, shape, electric charge, chemical properties, including the ability to form covalent or hydrogen bonds, or the like. The "percentage identity" between two sequences is a function of the number of positions that contain matching residues shared by the two sequences divided by the number of compared positions times 100.

As used herein, the term "conservative variant" refers to an amino acid sequence in which a first amino acid is replaced by a second amino acid or amino acid analog having at least one similar biochemical property, which can be, for example, similar size, charge, hydrophobicity or hydrogen-bonding capacity. For example, a first hydrophobic amino acid can be conservatively substituted with a second (non-identical) hydrophobic amino acid such as alanine, valine, leucine, or isoleucine, or an analog thereof. Similarly, a first basic amino acid can be conservatively substituted with a second basic amino acid such as arginine or lysine, or an analog thereof. In the same way, a first acidic amino acid can be conservatively substituted with a second acidic amino acid such as aspartic acid or glutamic acid, or an analog thereof, or an aromatic amino acid such as phenylalanine can be conservatively substituted with a second aromatic amino acid or amino acid analog, for example, tyrosine.

As used herein, the term "peptide" refers to peptides, proteins, fragments of proteins and the like.

As used herein, the term "peptidomimetic" refers to a peptide-like molecule that has the activity (e.g., binding affinity and/or specificity) of the peptide upon which it is structurally based. Such peptidomimetics include chemically modified peptides, peptide-like molecules containing non-naturally occurring amino acids, and peptoids and have an activity such as selective homing activity of the peptide upon which the peptidomimetic is derived (see, for example, Goodman and Ro, Peptidomimetics for Drug Design, in "Burger's Medicinal Chemistry and Drug Discovery" Vol. 1 (ed. M. E. Wolff; John Wiley & Sons 1995), pages 803-861).

An isolated peptide or peptidomimetic of the invention, or a homing molecule of the invention as discussed further below, can be cyclic, or otherwise conformationally constrained. As used herein, a "conformationally constrained" molecule, such as a peptide or peptidomimetic, is one in which the three-dimensional structure is maintained substantially in one spatial arrangement over time. Conformationally constrained molecules can have improved properties such as increased affinity, metabolic stability, membrane permeability or solubility. Methods of conformational constraint are well known in the art and include cyclization.

As used herein in reference to a peptide or peptidomimetic, the term "cyclic" refers to a structure including an intramolecular bond between two non-adjacent amino acids or amino acid analogues. The cyclization can be effected through a covalent or non-covalent bond. Intramolecular bonds include, but are not limited to, backbone to backbone, side-chain to backbone and side-chain to side-chain bonds. A preferred method of cyclization is through formation of a disulfide bond between the side-chains of non-adjacent amino acids or amino acid analogs. Residues capable of forming a disulfide bond include, for example, cysteine (Cys), penicillamine (Pen), β,β-pentamethylene cysteine (Pmc), β,β-pentamethylene-β-mercaptopropionic acid (Pmp) and functional equivalents thereof.

As used herein, the term "fragment" includes a peptide, polypeptide or protein segment of amino acids of the full-length protein, provided that the fragment retains reactivity with at least one antibody in sera of disease patients.

Targeting Tumor-Associated Macrophages

Disclosed herein are peptides that selectively target tumor-associated macrophages (TAMs) expressing the multi-ligand endocytic receptor mannose receptor (CD206/MRC1). These MRC1-expressing TAMs (MEMs) contribute to tumor immunosuppression, angiogenesis, metastasis, and relapse. Thus, the present disclosure teaches compositions and methods for targeting these M2-like TAMs that enable the elimination and/or reprogramming of these cells. This discovery has profound implications for treating or preventing diseases and conditions that in which M2-like TAMs play a central role.

Tumor-associated macrophages displaying a M2-like phenotype (M2 TAMs) play major roles in progression of solid tumors, including epithelial and mesenchymal tumors, glia-derived tumors, and melanoma. M2-like TAMs promote tumor growth and progression by stimulating tumor cell proliferation, and by secreting factors that promote angiogenesis, such as VEGF-A. M2 TAMs also induce transient openings in tumor neovessels that allow malignant cells to enter the bloodstream, promoting metastatic dissemination of solid tumors. K2-like TAMs increase in number after chemotherapy and contribute to tumor relapse. They also limit the efficacy of chemotherapies and support immunosuppressive microenvironment in tumors. The immunosuppressive effect is partly mediated through expression of ligands for the inhibitor receptors PD-1 (programmed cell death protein 1) and cytotoxic T-Lymphocyte Antigen-4 (cnA-4). The M2 differentiation state is supported in part by the exposure to Th2 cytokines, such as IL-4 and IL-13, which results in (1) upregulation of the anti-inflammatory cytokine, IL-10, (2) decreased expression of pro-inflammatory cytokines, (3) amplification of metabolic pathways that suppress adaptive immune responses, and (4) upregulation of cell-surface scavenger receptors such as the mannose receptor (MMR/CD206) and the hemoglobin/haptoglobin scavenger receptor (CD163). M2-like TAMs are derived from circulating monocytes that may already express M2 associated markers (such as CD206), which are further upregulated upon extravasation of the cells at the tumor site and by exposure to factors in the perivascular tumor microenvironment. The appreciation of the central role of TAMs in tumorigenesis and resistance to therapies has inspired multiple studies aimed to eliminate or reprogram TAMs.

Activated TAMs overexpress cell surface p32 protein, a molecule that can be targeted by LyP-1 peptide, its higher-affinity version TT1, and a low-molecular-weight peptidomimetic compound. Remarkably, treatment of tumor mice with the LyP-1 peptide or LyP-1-targeted clodronate nanoparticles caused decrease in TAMs in tumor models, resulting in partial tumor growth inhibition. However, cell surface p32 is expressed on activated TAMs, and on other types of cells in tumors, and does not allow specific targeting of M2-skewed macrophages. The Manocept™ family of multi-mannose analogue diagnostic imaging compounds targets the lectin domain of CD206. A $^{99m}$Tc-labeled version of Manocept™, y-Tilmanocept, is FDA approved for imaging of lymph nodes that drain from a primary tumor and have the highest probability of harboring cancer cells. However, mannose and its analogues are not specific for CD206: they also bind other mannose receptors, such as CD209 expressed in the skin and intestinal and genital mucosa. In addition, a nanobody that recognizes CD206 has been developed and its $^{99m}$Tc and $^{18}$F-labeled versions have been used for PET imaging of MEMs in mice. However, it is not known if the nanobody is internalized by the CD206-positive cells. Recently, a 10-mer peptide, RP-182, was reported to bind CD206. RP-182 is composed of alternating hydrophobic and hydrophilic amino acids, and is not specific to CD206, as it also binds RelE, SIRP-a, CD47 and TGM2. Finally, other groups have identified peptides that appear to target TAMs, however, the receptors for these peptides are unknown. Disclosed herein are the identity and characterization of peptides that selectively target MRC1-expressing tumor-associated macrophages (MEMs), including a peptide codenamed "UNO" that targets CD206 on MEMs across a spectrum of solid tumors of different types.

In vivo peptide phage display screens were performed in mice bearing 4T1 metastatic breast tumors to identify peptides that target peritoneal macrophages. Deep sequencing of the peptide-encoding inserts in the selected phage pool revealed enrichment of the peptide CSPGAKVRC (codenamed "UNO"; SEQ ID NO: 1). Intravenously injected FAM-labeled UNO (FAM-UNO) homed to tumor and sentinel lymph node MEMs in different cancer models: 4T1 and MCF-7 breast carcinoma, B16F10 melanoma, WT-GBM glioma and MKN45-P gastric carcinoma. Fluorescence anisotropy assays showed that FAM-UNO interacts with recombinant CD206 when subjected to reducing conditions. Interestingly, the GSPGAK (SEQ ID NO: 2) motif is present in all CD206-binding collagens. FAM-UNO was able to transport drug-loaded nanoparticles into MEMs, whereas particles without the peptide were not taken up MEMs. In ex vivo organ imaging, FAM-UNO showed significantly higher accumulation in sentinel lymph nodes than a control peptide. Accordingly, the peptides disclosed herein have applications for diagnostic imaging and therapeutic targeting of MEMs in various disease environments such as in solid tumors.

Accordingly in vivo phage display on peritoneal cells of tumor bearing mice was used to identify probes for M2-like TAMs, a cell population recognized to play increasingly important roles in tumor growth and metastasis. The UNO peptide has been found to target MEMs in solid tumors of different origin. UNO is specific for MEMs, and it effectively delivers payloads, including nanoparticles, into the tumors. In vivo phage display has been successfully used to identify peptides that home to tumors, including macrophages in them. As this method primarily targets tumor endothelium, it was necessary to remove the endothelial cells in earlier screens for it to yield LyP-1 peptide, shown to recognize tumor lymphatics and activated TAMs. Here, to focus the screening on TAMs, peritoneal macrophages from tumor-bearing mice were used as the target rather than tumors. FAM-UNO accumulated in M2-like TAMs in all 5 different solid tumor models tested, suggesting that the peptide targets MEMs independently of the origin of the malignancy and location of the tumor. The specificity of UNO is different from the TAM-targeting peptide, LyP-1, which is not selective for MEMs. The selectivity of UNO for MEMs was evident from the extensive colocalization of systemically injected FAM-UNO with CD206, (see quantifications of (FAM and CD206)$^+$ cells/FAM cells of FIG. 3). The experiments of FIG. 4C showed that FAM-UNO mainly (95%) binds macrophages. These results lead us to conclude that FAM-UNO does not bind macrophages other than MEMs. Our data indicate that the target molecule (receptor) for UNO in MEMs is CD206.

First, the immunofluorescence results show that UNO is highly selective for CD206$^+$ cells. Second, linearized FAM-UNO and FAM-CSPGAK bind to recombinant CD206 in fluorescence anisotropy assay. Third, binding of FAM-UNO peptide to peritoneal cells is reduced after pre-incubation with an anti-CD206 blocking antibody. That the antibody inhibition was only partial may be because the anti-CD206 antibody used in this study is monoclonal and the binding epitope on CD206 is likely to be different from the binding epitope for the peptide. CD206 is a modular protein composed of 3 domains: (1) a mannose-binding lectin domain located closest to the plasma membrane composed of 8 consecutive C-type carbohydrate recognition domains (CRDs); (2) a conserved fibronectin type-II (FNII) domain that interacts with type I, III and IV collagens and their degradation and denaturation products; (3) a cysteine-rich domain homologous to the ricin B chain that interacts with sulfated glycans. The sharing of the UNO sequence by collagens and the antibody inhibition data implicate the collagen-binding domain of CD206 in the UNO interaction. Importantly, UNO does not only act as a cellular membrane-docking ligand but is also robustly internalized in CD206-expressing macrophages. This observation agrees with the known physiological role of CD206 as an endocytic receptor for cellular uptake of its ligands, including collagens. Following internalization, CD206 dissociates from its ligands and is recycled back to the cell surface. The ability of UNO peptide to carry the coupled FAM reporter into the MEMs suggests that the peptide can be used for intracellular delivery of therapeutically relevant payloads. Previously, targeting the pro-apoptotic peptide D[KLAKLAK]2 to M2 macrophages was shown to result in improved survival in a mouse syngeneic colon cancer model. Moreover, interferon-a delivery by TIE-2 expressing TAMs in an orthotopic glioma model activated innate and adaptive antitumor responses, which translated into inhibition of cancer progression and near-complete abrogation of metastasis.

Tasquinimod, a small molecule antagonist of the 160 calcium-binding protein A9 (160A9), was recently shown to inhibit MEMs and enhance immunotherapy in prostate and B16 melanoma models. Finally, siRNA knockdown of the endoribonuclease DICER to reprogram M2 macrophages shows therapeutic promise. MEM-directed delivery with UNO peptide could potentially enhance the efficacy of such approaches. The data shows that in addition to enabling delivery of molecular payloads, UNO is capable of guiding drug-loaded nanoparticles to MEMs. Cells of monocytic/macrophage lineage have an inherent ability to effectively take up foreign particles, including nanoparticles. However, the polymersome data show that MEMs did not take up these nanoparticles unless they were coated with FAM-UNO.

UNO can be used in peptide-mediated delivery of polymersome-encapsulated drugs and silicon nanoparticle-encapsulated siRNA to various disease targets. The potential applications of this MEM-targeting peptide extend beyond therapy. UNO-based imaging agents could be developed into companion diagnostic tests to stratify patients for therapeutic targeting of MEMs and to assess the efficacy of cancer treatments. Moreover, it has been reported that the presence of MEMs in lymph nodes is elevated in early cancer in humans. Here, data shows that UNO homes to MEMs in the lymph nodes, making it potentially suitable for sentinel lymph node imaging.

Peptides and Peptidomimetics

Disclosed herein are isolated peptides or peptidomimetics which can be useful for medical imaging or therapeutic treatment. Also disclosed are compositions comprising the isolated peptides or peptidomimetics described herein. In some embodiments, the peptide or peptidomimetic comprises an amino acid sequence selected from Table 1. In some embodiments, the peptide or peptidomimetic comprises a conservative variant of an amino acid sequence selected from Table 1. In some embodiments, the peptide or peptidomimetic comprises an amino acid sequence selected from SEQ ID NOs: 1, 2, 6, or 8-30. In some embodiments, the peptide or peptidomimetic comprises a conservative variant of an amino acid sequence selected from SEQ ID NOs: 1, 2, 6, or 8-30. In some embodiments, the peptide or peptidomimetic comprises the amino acid sequence CSPGAKVRC (SEQ ID NO: 1). In some embodiments, the peptide or peptidomimetic comprises a conservative variant of the amino acid sequence CSPGAKVRC (SEQ ID NO: 1). In some embodiments, the peptide or peptidomimetic comprises the amino acid sequence CSPGAK (SEQ ID NO: 6). In some embodiments, the peptide or peptidomimetic comprises a conservative variant of the amino acid sequence CSPGAK (SEQ ID NO: 6). In some embodiments, the peptide or peptidomimetic comprises the amino acid sequence GSPGAK (SEQ ID NO: 2). In some embodiments, the peptide or peptidomimetic comprises a conservative variant of the amino acid sequence GSPGAK (SEQ ID NO: 2).

In some embodiments, the peptide or peptidomimetic targets or selectively homes to tumor tissue. In some embodiments, the peptide or peptidomimetic targets or selectively homes to solid tumor tissue. In some embodiments, the peptide or peptidomimetic targets or selectively homes to tumor tissue that is a sarcoma, carcinoma, or blastoma. In some embodiments, the sarcoma is Askin's tumor, sarcoma botryoides, chondrosarcoma, Ewing's sarcoma, malignant hemangioendothelioma, malignant schwannoma, osteosarcoma, or soft tissue sarcoma. In some embodiments, soft tissue sarcoma includes alveolar soft part sarcoma, angiosarcoma, desmoid tumor, epithelioid sarcoma, fibrosarcoma, gastrointestinal stromal tumor, Kaposi's sarcoma, liposarcoma, lymphangiosarcoma, neurofibrosarcoma, rhabdomyosarcoma, or synovial sarcoma. In some embodiments, the blastoma is hepatoblastoma, medulloblastoma, nephroblastoma, neuroblastoma, pancreatoblastoma, pleuropulmonary blastoma, retinoblastoma, glioblastoma multiforme, or gonadoblastoma. In some embodiments, the carcinoma is adenocarcinoma, squamous cell carcinoma, adenosquamous carcinoma, anaplastic carcinoma, large cell carcinoma, or small cell carcinoma.

In some embodiments, the peptide or peptidomimetic targets or selectively homes to immune cells. In some embodiments, the peptide or peptidomimetic targets or selectively homes to macrophages. In some embodiments, the peptide or peptidomimetic targets or selectively homes to tumor-associated macrophages. In some embodiments, the peptide or peptidomimetic targets or selectively homes to tumor-associated macrophages having a M2-like phenotype. In some embodiments, the peptide or peptidomimetic targets or selectively homes to CD206. In some embodiments, the peptide or peptidomimetic targets or selectively homes to human CD206. In some embodiments, the peptide or peptidomimetic targets or selectively homes to MRC1/CD206-expressing tumor-associated macrophages (MEMs). In some embodiments, the peptide or peptidomimetic targets or selectively homes to TIE2-expressing tumor-associated macrophages (MEMs).

In some embodiments, the peptide or peptidomimetic is conformationally constrained. In some embodiments, the peptide or peptidomimetic is cyclic. In some embodiments, the peptide or peptidomimetic comprises a disulfide bond. In some embodiments, the peptide or peptidomimetic comprises a cyclic structure formed by a disulfide bond. In some embodiments, the peptide or peptidomimetic comprises a cyclic structure or a non-cyclic structure in which the non-cyclic structure has increased affinity for a target molecule. In some embodiments, the peptide or peptidomimetic has a cyclic structure formed by a disulfide bond and has increased affinity for the target molecule after the disulfide bond is broken. In some embodiments, the target molecule is a surface molecule expressed on tumor-associated macrophages. In some embodiments, the target molecule is CD206.

In some embodiments, the peptide or peptidomimetic comprises a modified peptide. In some embodiments, the peptide is alkylated. In some embodiments, the peptide comprises a methylated amino acid. In some embodiments, the peptide is N- or C-methylated in at least one position or residue. In some embodiments, the peptide is acylated in at least one position or residue. In some embodiments, the peptide is glycosylated in at least one position or residue.

In some embodiments, the peptide or peptidomimetic has a length of no greater than 300 residues. In some embodiments, the peptide or peptidomimetic has a length of no greater than 250 residues. In some embodiments, the peptide or peptidomimetic has a length of no greater than 200 residues. In some embodiments, the peptide or peptidomimetic has a length of no greater than 150 residues. In some embodiments, the peptide or peptidomimetic has a length of no greater than 100 residues. In some embodiments, the peptide or peptidomimetic has a length of no greater than 80 residues. In some embodiments, the peptide or peptidomimetic has a length of no greater than 60 residues. In some embodiments, the peptide or peptidomimetic has a length of no greater than 40 residues. In some embodiments, the peptide or peptidomimetic has a length of no greater than 20 residues. In some embodiments, the peptide or peptidomimetic has a length of no greater than 10 residues. In some embodiments, the peptide or peptidomimetic has a length of no greater than 9 residues. In some embodiments, the peptide or peptidomimetic has a length of no greater than 6 residues.

In some embodiments, the peptide or peptidomimetic has at least 70%, at least 80%, or at least 90% sequence identity with an amino acid selected from Table 1. In some embodiments, the peptide or peptidomimetic has at least 70%, at least 80%, or at least 90% sequence identity with an amino acid sequence selected from SEQ ID NOs: 1, 2, 6, or 8-30. In some embodiments, the peptide or peptidomimetic has at least 70%, at least 80%, or at least 90% sequence identity with the amino acid sequence CSPGAKVRC (SEQ ID NO:

1). In some embodiments, the peptide or peptidomimetic has at least 70%, at least 80%, or at least 90% sequence identity with the amino acid sequence CSPGAK (SEQ ID NO: 6). In some embodiments, the peptide or peptidomimetic has at least 70%, at least 80%, or at least 90% sequence identity with the amino acid sequence GSPGAK (SEQ ID NO: 2).

In some embodiments, the peptide or peptidomimetic comprises two or more repeats of an amino acid sequence. In some embodiments, the peptide or peptidomimetic comprises at least two repeats, at least three repeats, at least four repeats, at least five repeats, at least six repeats, at least seven repeats, at least eight repeats, at least nine repeats, or at least ten repeats of an amino acid sequence. In some embodiments, the peptide or peptidomimetic comprises two or more repeats of an amino acid sequence selected from Table 1. In some embodiments, the peptide or peptidomimetic comprises two or more repeats of an amino acid sequence selected from SEQ ID NOs: 1, 2, 6, or 8-30. In some embodiments, the peptide or peptidomimetic comprises two or more repeats of the amino acid sequence CSPGAKVRC (SEQ ID NO: 1). In some embodiments, the peptide or peptidomimetic comprises two or more repeats of the amino acid sequence CSPGAK (SEQ ID NO: 6). In some embodiments, the peptide or peptidomimetic comprises two or more repeats of the amino acid sequence GSPGAK (SEQ ID NO: 2). In some embodiments, the peptide or peptidomimetic comprises two or more repeats of a conservative variant of an amino acid sequence selected from Table 1. In some embodiments, the peptide or peptidomimetic comprises two or more repeats of a conservative variant of an amino acid sequence selected from SEQ ID NOs: 1, 2, 6, or 8-30. In some embodiments, the peptide or peptidomimetic comprises two or more repeats of a conservative variant of the amino acid sequence CSPGAKVRC (SEQ ID NO: 1). In some embodiments, the peptide or peptidomimetic comprises two or more repeats of a conservative variant of the amino acid sequence CSPGAK (SEQ ID NO: 6). In some embodiments, the peptide or peptidomimetic comprises two or more repeats of a conservative variant of the amino acid sequence GSPGAK (SEQ ID NO: 2).

When a peptidomimetic is described as comprising an amino acid sequence, it is understood that the peptidomimetic comprises a structure that mimics the structure or shape of the amino acid sequence. A variety of peptidomimetics are known in the art including, for example, peptide-like molecules which contain a constrained amino acid, a non-peptide component that mimics peptide secondary structure, or an amide bond isostere. A peptidomimetic that contains a constrained, non-naturally occurring amino acid can include, for example, an α-methylated amino acid; α,α-dialkylglycine or α-aminocycloalkane carboxylic acid; an N α-Cα cyclized amino acid; an Nα-methylated amino acid; a β- or γ-amino cycloalkane carboxylic acid; an α, β-unsaturated amino acid; a β,β-dimethyl or β-methyl amino acid; a β-substituted-2,3-methano amino acid; an N—Cδ or Cα-C 67 cyclized amino acid; a substituted proline or another amino acid mimetic. A peptidomimetic which mimics peptide secondary structure can contain, for example, a nonpeptidic β-turn mimic; γ-turn mimic; mimic of β-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylenesulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

Methods for identifying a peptidomimetic are well known in the art and include, for example, the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). This structural depository is continually updated as new crystal structures are determined and can be screened for compounds having suitable shapes, for example, the same shape as a peptide of the invention, as well as potential geometrical and chemical complementarity to a target molecule. Where no crystal structure of a peptide of the invention or a target molecule that binds the peptide is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of a peptide of the invention, for example, with activity in selectively homing to tumor lymphatic vasculature.

TABLE 1 listing of sequences

| SEQ ID NO | Peptide sequence | FIG. |
|---|---|---|
| 1 | CSPGAKVRC | N/A |
| 2 | GSPGAK | N/A |
| 3 | CGEKRTRGC | N/A |
| 4 | CGNKRTRGC | N/A |
| 5 | CRKQGEAKC | N/A |
| 6 | CSPGAK | N/A |
| 7 | CPMTDNE | N/A |
| 8 | CDSRSRKRC | FIG. 1c |
| 9 | CPKGAGSKC | FIG. 1c |
| 10 | CRKGTLGRC | FIG. 1c |
| 11 | CVKGTVKTC | FIG. 1c |
| 12 | CRGTIRGRC | FIG. 1c |
| 13 | CLDRRKKPC | FIG. 1c |
| 14 | CPARRSNRC | FIG. 1c |
| 15 | CKDSAEMRC | FIG. 1c |
| 16 | CERSNNVSC | FIG. 1c |
| 17 | CGKRAPFRC | FIG. 1c |
| 18 | CVSSSSGRC | FIG. 1c |
| 19 | CTVAGSGPC | FIG. 1c |
| 20 | CIGNSKKKC | FIG. 1c |
| 21 | CVRLREKRC | FIG. 1c |

TABLE 1-continued listing of sequences

| SEQ ID NO | Peptide sequence | FIG. |
|---|---|---|
| 22 | CRKKSRAQC | FIG. 1c |
| 23 | CAANDYSDC | FIG. 1c |
| 24 | CLEDDSAKC | FIG. 1c |
| 25 | CNDKS | FIG. 1c |
| 26 | CVGRKVRGC | FIG. 1c |
| 27 | CVDRRESRC | FIG. 1c |
| 28 | CRQEEESRC | FIG. 1c |
| 29 | CGKTRYSRC | FIG. 1c |
| 30 | CIGVSSDC | FIG. 1d |
| 31 | CRTLRSKAC | FIG. 26 |
| 32 | CRRTRQRSC | FIG. 26 |
| 33 | CIGNK | FIG. 26 |
| 34 | CVLNESGDC | FIG. 26 |
| 35 | CRDKRGSKC | FIG. 26 |
| 36 | CKRPNENVC | FIG. 26 |
| 37 | CNRRTKIGC | FIG. 26 |
| 38 | CSPKMRATC | FIG. 26 |
| 39 | CKRTRRREC | FIG. 26 |
| 40 | CLSSITPEC | FIG. 26 |
| 41 | CVDQDPL | FIG. 26 |
| 42 | CRGTRSNRC | FIG. 26 |
| 43 | CGPCQEGLC | FIG. 26 |
| 44 | CMTLRSRKC | FIG. 26 |
| 45 | CSTKTSLKC | FIG. 26 |
| 46 | CGDEA | FIG. 26 |
| 47 | CTTSTGADC | FIG. 26 |
| 48 | CSTLKRRVC | FIG. 26 |
| 49 | CRGVAKVRC | FIG. 26 |
| 50 | CSVGRLK | FIG. 26 |
| 51 | CHQDF | FIG. 26 |
| 52 | CSFDEANPC | FIG. 26 |
| 53 | CRNRA | FIG. 26 |
| 54 | CVSDRKVAC | FIG. 26 |
| 55 | CKRGRFAKL | FIG. 26 |
| 56 | CAQPNSR | FIG. 26 |
| 57 | CRPTRRVSC | FIG. 26 |
| 58 | CRNGLNKRC | FIG. 26 |
| 59 | CGFRSD | FIG. 26 |
| 60 | CRKTVGPRC | FIG. 26 |
| 61 | CEVMQRKRC | FIG. 26 |
| 62 | CVASVKRKC | FIG. 26 |
| 63 | CDANQ | FIG. 26 |
| 64 | CRRTAIKKC | FIG. 26 |
| 65 | CLSKRTPRC | FIG. 26 |
| 66 | CVDSEATDC | FIG. 26 |
| 67 | CPRTAKVLC | FIG. 26 |
| 68 | CQSRSPRNC | FIG. 26 |
| 69 | CNKNGTAPC | FIG. 26 |
| 70 | CTDRHSTNC | FIG. 26 |
| 71 | CDALAPNSC | FIG. 26 |
| 72 | CIDGRTDLC | FIG. 26 |
| 73 | CMNVESSPC | FIG. 26 |
| 74 | CREKNSQRC | FIG. 26 |
| 75 | CLVRPERKC | FIG. 26 |
| 76 | CRKMNRTC | FIG. 26 |
| 77 | CVDITSPDC | FIG. 26 |
| 78 | CSYEKEPVC | FIG. 26 |

Detectable Tags or Agents

Disclosed herein are detectable tags or agents that are conjugated, attached, or associated with the compositions, peptides, or peptidomimetics to enable detection of molecular targets. In some embodiments, the detectable agent is directly linked to the peptide through a covalent bond. In some embodiments, the detectable agent is indirectly linked to the peptide or peptidomimetic. For example, the detectable agent can be stored within an interior space of a vesicle such as a liposome or polymersome that displays the peptide or peptidomimetic on the exterior surface. In some embodiments, the detectable agent is an affinity tag, a fluorescent label, a radionuclide, or other detectable molecule. Exemplary affinity tags include, but are not limited to, biotin, desthiobiotin, histidine, polyhistidine, myc, hemagglutinin (HA), FLAG, glutathione S transferase (GST), or derivatives thereof. In some embodiments, the affinity tag is recognized by avidin, streptavidin, nickel, or glutathione. In some embodiments, the fluorescent label is a fluorophore, a fluorescent protein, a fluorescent peptide, quantum dots, a fluorescent dye, a fluorescent material, or variations or combinations thereof.

Exemplary fluorophores include, but are not limited to, Alexa-Fluor dyes (e.g., Alexa Fluor® 350, Alexa Fluor® 405, Alexa Fluor® 430, Alexa Fluor® 488, Alexa Fluor® 500, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor®

647, Alexa Fluor® 660, Alexa Fluor® 680, Alexa Fluor® 700, and Alexa Fluor® 750), APC, Cascade Blue, Cascade Yellow and R-phycoerythrin (PE), DyLight 405, DyLight 488, DyLight 550, DyLight 650, DyLight 680, DyLight 755, DyLight 800, FITC, Pacific Blue, PerCP, Rhodamine, and Texas Red, Cy5, Cy5.5, Cy7.

Examples of fluorescent peptides include GFP (Green Fluorescent Protein) or derivatives of GFP (e.g., EBFP, EBFP2, Azurite, mKalama1, ECFP, Cerulean, CyPet, YFP, Citrine, Venus, YPet).

Examples of fluorescent dyes include, but are not limited to, xanthenes (e.g., rhodamines, rhodols and fluoresceins, and their derivatives); bimanes; coumarins and their derivatives (e.g., umbelliferone and aminomethyl coumarins); aromatic amines (e.g., dansyl; squarate dyes); benzofurans; fluorescent cyanines; indocarbocyanines; carbazoles; dicyanomethylene pyranes; polymethine; oxabenzanthrane; xanthene; pyrylium; carbostyl; perylene; acridone; quinacridone; rubrene; anthracene; coronene; phenanthrecene; pyrene; butadiene; stilbene; porphyrin; pthalocyanine; lanthanide metal chelate complexes; rare-earth metal chelate complexes; and derivatives of such dyes. In some embodiments, the fluorescein dye is, but not limited to, 5-carboxyfluorescein, fluorescein-5-isothiocyanate, fluorescein-6-isothiocyanate and 6-carboxyfluorescein. In some embodiments, the rhodamine dye is, but not limited to, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, and rhodamine 101 sulfonyl chloride (sold under the tradename of TEXAS RED®). In some embodiments, the cyanine dye is Cy3, Cy3B, Cy3.5, Cy5, Cy5.5, Cy7, IRDYE680, Alexa Fluor 750, IRDye800CW, or ICG.

Fluorescent labels are detected by any suitable method. For example, a fluorescent label is detected by exciting the fluorochrome with the appropriate wavelength of light and detecting the resulting fluorescence, e.g., by microscopy, visual inspection, via photographic film, by the use of electronic detectors such as charge coupled devices (CCDs), or photomultipliers. In some embodiments, the one or more probe(s) are labeled with the same fluorescent label. In some embodiments, the one or more probe(s) are labeled with different fluorescent labels.

In some embodiments, the peptide or peptidomimetic is radiolabeled using a radiometal. The radiometal can be attached to the peptide using a bifunctional chelating agent (BFCA). Examples of suitable radionuclides for diagnostic imaging include $^{99m}Tc$, $^{111}In$, $^{68/66}Ga$, $^{18}F$, $^{123}I$, $^{64}Cu$. Examples of BFCAs include mercaptoacetyltriglycine; diaminedithiol; 2-hydrazinonicotinic acid; N-succinimidyl-4-[$^{18}F$]fluorobenzoate; 1,4,8,11-tetraazacyclotetradecane-1,4,8,11-tetraacetic acid; N-succinimidyl-3-iodobenzoate; N-succinimidyl-5-iodo-3-pyridinecarboxylate; diethylenetriaminepentaacetic acid; 1,4,7,10-tetraazacyclododecane-1,4,7,10-tetraacetic acid; and 1,4,7-triazacyclononane-1,4,7-triacetic acid.

In some embodiments, the detectable agent is Feridex, a tantalum compound, iodine, radioactive iodine, an organic iodo acid, iron oxide, gadolinium, an enzyme, biotin, a metal, barium sulfate, diatrizoic acid sodium salt dehydrate, Lissamine Rhodamine PE, Rhodamine, a radioisotope, a ferromagnetic compound, a paramagnetic compound, a diamagnetic compound, indium-111, technetium-99, carbon-11, or carbon-13.

Diseases and Disorders

In some aspects, disclosed herein are peptides, compositions, and methods for diagnosing, detecting, monitoring, and/or treating various diseases or disorders such as cancer and autoimmune or inflammatory diseases or disorders. Examples of cancers include medulloblastoma, melanoma, hepatocellular carcinoma, breast cancer, lung cancer, prostate cancer, bladder cancer, ovarian cancer, leukemia, lymphoma, renal carcinoma, pancreatic cancer, epithelial carcinoma, gastric cancer, colon carcinoma, duodenal cancer, pancreatic adenocarcinoma, mesothelioma, glioblastoma multiforme, astrocytoma, multiple myeloma, prostate carcinoma, hepatocellular carcinoma, cholangiosarcoma, pancreatic adenocarcinoma, head and neck squamous cell carcinoma, colorectal cancer, intestinal-type gastric adenocarcinoma, cervical squamous-cell carcinoma, osteosarcoma, epithelial ovarian carcinoma, acute lymphoblastic lymphoma, myeloproliferative neoplasms, and sarcoma. Cancer cells that can be treated by the methods of this disclosure include cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

Inflammation is an important process in the normal defense mechanisms against various pathogens, and leukocytes are the principal cellular mediators of inflammation. Inflammation is characterized histologically by the accumulation of leukocytes in the affected tissue due to migration of circulating leukocytes out of the vasculature, a process which is actively mediated and precisely controlled by leukocytes, the cytokines they produce, and the vascular endothelium.

Inflammation is usually a normal, healthy response to injury or infection. However, excessive or uncontrolled inflammatory responses can lead to the pathologic inflammation seen in many rheumatologic and inflammatory disorders, where the inflammation, rather than promoting healing, seriously damages normal tissues, resulting in chronic pain, contributing to a wide variety of serious disorders, in some cases increasing the risk of cancer and heart disease, and in some cases even causing death. Inflammatory bowel disease (IBD), for example, is a debilitating and progressive disease involving inflammation of the gastrointestinal tract. Symptoms include abdominal pain, cramping, diarrhea and bleeding.

One indication of such inflammatory diseases is the presence of inflammatory cells such as neutrophils and macrophages at local sites of inflammation. Inflammation is a response of vascularized tissue to infection and/or injury and it is affected by adhesion of leukocytes to the endothelial cells of blood vessels and their infiltration into the surrounding tissues. Such local concentrations can be detected by invasive methods requiring biopsy procedures and pathology analysis. The inflammatory state can also lie systemic, e.g. polypeptides secreted by inflammatory cells become detectable in the blood serum.

Non-limiting examples of autoimmune disease include inflammatory bowel disease, rheumatoid arthritis, diabetes mellitus, celiac disease, autoimmune thyroid disease, autoimmune liver disease, Addison's Disease, Sjögren's Syndrome, transplant rejection, graft vs. host disease, or host vs. graft disease.

Diagnosing, Detecting, and Monitoring Diseases and Disorders

In some aspects, disclosed herein are compositions and methods for carrying out diagnostic or medical imaging in a subject. In some embodiments, the imaging is carried out on a subject by administering a composition comprising a peptide or peptidomimetic and a detectable agent. In some embodiments, the composition is administered intravenously. In some embodiments, the method of medical imaging is carried out by administering to the subject a composition comprising a peptide or peptidomimetic and a detectable agent linked to the peptide and detecting a detectable signal of the detectable agent. For example, following administration of the composition, the subject or a biological sample obtained from the subject can be analyzed such as by a medical imaging technique to detect, locate, and/or quantify the detectable signal of the detectable agent. In some embodiments, the signal is detected in the lymph nodes. In some embodiments, the signal is detected in tumor tissue. In some embodiments, the signal is detected in solid tumor tissue.

Provided herein, in some embodiments, are methods for directing a moiety to a MRC1-expressing tumor associated macrophage in a subject, comprising administering to the subject a composition comprising the moiety linked to an isolated peptide or peptidomimetic comprising the amino acid sequence CSPGAK (SEQ ID NO: 6) or a peptidomimetic thereof.

Provided herein, in some embodiments, are methods of diagnosing a subject with a disease or disorder, comprising administering to the subject a composition comprising a detectable agent linked to an isolated peptide or peptidomimetic comprising the amino acid sequence CSPGAK (SEQ ID NO: 6) or a peptidomimetic thereof.

Provided herein, in some embodiments, are methods of performing medical imaging on a subject with a disease or disorder, comprising administering to the subject a composition comprising a detectable agent linked to an isolated peptide or peptidomimetic comprising the amino acid sequence CSPGAK (SEQ ID NO: 6) or a peptidomimetic thereof.

In some embodiments, the peptide or peptidomimetic comprises an amino acid sequence as described throughout the present disclosure including any of the sequences in Table 1. In some embodiments, the peptide or peptidomimetic comprises the amino acid sequence of SEQ ID NO: 1. In some embodiments, the peptide or peptidomimetic comprises the amino acid sequence of SEQ ID NO: 6. In some embodiments, the peptide is a homing molecule that selectively targets or homes to a target tissue. In some embodiments, the homing molecule selectively targets or homes to macrophages. In some embodiments, the homing molecule selectively targets or homes to tumor tissue. In some embodiments, the homing molecule selectively targets or homes to solid tumor tissue. In some embodiments, the homing molecule selectively targets or homes to tumor-associated macrophages. In some embodiments, the homing molecule selectively targets or homes to CD206. In some embodiments, the homing molecule selectively homes or targets MRC1/CD206-expressing tumor-associated macrophages (MEMs). In some embodiments, the homing molecule does not accumulate in the liver. In some embodiments, the peptide shows low accumulation in the liver. In some embodiments, the peptide does not accumulate in healthy or non-malignant tissue. In some embodiments, the peptide does not accumulate in healthy lymph nodes. In some embodiments, the peptide or peptidomimetic has a cyclic structure that inhibits binding or association with a target molecule. In some embodiments, the peptide or peptidomimetic has a cyclic structure that linearizes under reducing conditions. In some embodiments, the peptide or peptidomimetic exhibits high affinity for the target molecule under reducing conditions. In some embodiments, the peptide or peptidomimetic exhibits high affinity for the target molecule within tumor tissue.

In some embodiments, the detectable agent is directly linked to the peptide. In some embodiments, the peptide is radiolabeled. In some embodiments, the detectable agent is indirectly linked to the peptide. In some embodiments, the detectable agent is noncovalently linked to the peptide. For example, the peptide may be conjugated to a polymer and then used to prepare polymersomes containing the detectable agent within the interior space. Other examples of detectable labels that can be used to enhance medical imaging include quantum dots for optical imaging, magnetic nanoparticles such as magnetic iron oxide nanoparticles (IONPs) for magnetic resonance imaging (MRI).

In some embodiments, the imaging method utilizes an imaging technique such as X-ray, magnetic resonance imaging (MRI), single photon emission computed tomography (SPECT), positron emission tomography (PET), computed tomography (CT) perfusion imaging, or magnetic particle imaging.

The present methods can be useful for detecting the presence of tumor tissue such as solid tumors. Following administration of a composition comprising a peptide and a detectable agent, the tumor tissue is visualized. In some embodiments, the method allows detection of tumor-associated M2-like macrophages that are involved in immune suppression and cancer survival. If the image is positive for the presence of such tumor tissue, the tumor can be evaluated to provide valuable information to the clinician with regard to the stage of development of the cancer and the presence or probability of metastasis. In a method of imaging tumor tissue, the composition administered contains a detectable label that allows detection or visualization of in tumors, for example in breast tumors or in osteosarcomas. For in vivo diagnostic imaging of such tumor tissue, a homing molecule selective for the desired tumor is linked to a detectable agent that, upon administration to the subject, is detectable external to the subject. Such a detectable label can be, for example, a radionuclide that can be visualized using a solid scintillation detector.

In some aspects, disclosed herein are methods for diagnosing, detecting, or monitoring a cancer in a subject. In some embodiments, the cancer is medulloblastoma, melanoma, hepatocellular carcinoma, breast cancer, lung cancer, prostate cancer, bladder cancer, ovarian cancer, leukemia, lymphoma, renal carcinoma, pancreatic cancer, epithelial carcinoma, gastric cancer, colon carcinoma, duodenal cancer, pancreatic adenocarcinoma, mesothelioma, glioblastoma multiforme, astrocytoma, multiple myeloma, prostate carcinoma, hepatocellular carcinoma, cholangiosarcoma, pancreatic adenocarcinoma, head and neck squamous cell carcinoma, colorectal cancer, intestinal-type gastric adenocarcinoma, cervical squamous-cell carcinoma, osteosarcoma, epithelial ovarian carcinoma, acute lymphoblastic lymphoma, myeloproliferative neoplasms, or sarcoma.

In some aspects, disclosed herein are methods of diagnosing, detecting, or monitoring an immune disorder in a subject using a composition comprising peptide or peptidomimetic and a detectable agent. In some embodiments, the immune disorder is an autoimmune disease or disorder. In some embodiments, the immune disorder is an inflammatory disease. In some embodiments, the immune disorder is inflammatory bowel disease, rheumatoid arthritis, diabetes mellitus, celiac disease, autoimmune thyroid disease, autoimmune liver disease, Addison's Disease, Sjögren's Syndrome, transplant rejection, graft vs. host disease, or host vs. graft disease. In certain embodiments, the immune disorder is IBD. In certain embodiments, the IBD is ulcerative colitis. In certain embodiments, the IBD is Crohn's disease. In some embodiments, the subject is a mammal. In some embodiments, the subject is a human.

In some aspects, disclosed herein are methods for detecting inflammatory markers for use in diagnosis and prevention of inflammatory disease. In some embodiments, the marker of inflammation is a composition comprising a peptide or peptidomimetic and a detectable agent. In some embodiments, the peptide or peptidomimetic comprises an amino acid sequence of SEQ ID NO: 1. In some embodiments, the peptide or peptidomimetic comprises an amino acid sequence of SEQ ID NO: 6. In some embodiments, the peptide or peptidomimetic comprises an amino acid sequence of any of the SEQ ID NOs in Table 1. In some embodiments, the presence, absence, or level of the inflammatory marker predicts a severity or status of the inflammatory disease or condition.

In some aspects, disclosed herein are methods for monitoring the status or progression or regression of an inflammatory disease or condition. In some embodiments, the presence or level of an inflammatory marker can be determined, and the severity of the inflammatory disease or condition can be inferred based on the presence or level of the inflammatory marker.

In some embodiments, the frequency of at least one type of inflammation-associated cells can be determined, and the severity of the inflammatory disease or condition can be inferred based on the count or frequency of the at least one type of inflammation associated cells. In some embodiments, the inflammation associated cells are macrophages. In some embodiments, the macrophages are tumor-associated macrophages. In some embodiments, the macrophages at CD206-expressing tumor-associated macrophages. In some embodiments, the macrophages are not tumor-associated macrophages. In some embodiments, the macrophages are CD206-expressing non-tumor associated macrophages. In some embodiments, the inflammation associated cells are dendritic cells. In some embodiments, the inflammation associated cells are T cells. In some embodiments, the inflammation associated cells are Th cells. In some embodiments, the inflammation associated cells are neutrophils. In some embodiments, the inflammation associated cells are inflammatory monocytes. In some embodiments, the inflammation associated cells are epithelial cells. In some embodiments, the inflammation associated cells are CD4+ cells, CD4+CD44+ cells, CD4+CD25+ cells, CD8+ cells, CD8+CD44+ cells, colonic DCs, colonic macrophages, or any combination thereof.

In some aspects, disclosed herein are methods for monitoring, screening, or determining the efficiency of a drug candidate for treatment of an inflammatory disease or condition. For example, the presence or level of at least one inflammation related marker in a subject can be determined prior to treatment with a drug candidate and compared with the presence or level of the at least one inflammation related marker in the subject post treatment of the drug candidate. In some embodiments, the presence or level of at least one inflammation associated cells in a subject can be determined prior to treatment with a drug candidate and compared with the presence or level of the at least one inflammation associated cells in the subject post treatment of the drug candidate.

Methods of Treatment

In another aspect, disclosed herein are compositions and methods for treating a subject for a cancer, an autoimmune disease, or an inflammatory disorder. In some embodiments method comprises administering to the subject a composition comprising a peptide or peptidomimetic and a drug or payload comprising the drug. In some embodiments, the peptide or peptidomimetic is associated with the drug or payload. In some embodiments, the peptide or peptidomimetic is conjugated or linked to a payload comprising a drug or other therapeutic compound for treating a subject for a disease or disorder and/or preventing the disease or disorder. In some embodiments, the peptide or peptidomimetic comprises an amino acid sequence as described throughout the present disclosure including any of the sequences in Table 1. For example, in some embodiments, methods of treating a subject with a disease or disorder comprise administering to the subject a composition comprising a therapeutic agent linked to an isolated peptide or peptidomimetic comprising the amino acid sequence CSPGAK (SEQ ID NO: 6) or a peptidomimetic thereof.

In some embodiments, the peptide or peptidomimetic is a homing molecule that selectively targets or homes to a target tissue. In some embodiments, the homing molecule selectively targets or homes to macrophages. In some embodiments, the homing molecule selectively targets or homes to tumor tissue. In some embodiments, the homing molecule selectively targets or homes to solid tumor tissue. In some embodiments, the homing molecule selectively targets or homes to tumor-associated macrophages. In some embodiments, the homing molecule selectively targets or homes to CD206. In some embodiments, the homing molecule selectively homes or targets MRC1/CD206-expressing tumor-associated macrophages (MEMs). In some embodiments, the homing molecule does not accumulate in the liver. In some embodiments, the peptide or peptidomimetic shows low accumulation in the liver. In some embodiments, the peptide or peptidomimetic does not accumulate in healthy or non-malignant tissue. In some embodiments, the peptide or peptidomimetic does not accumulate in healthy lymph nodes.

In some embodiments, the peptide or peptidomimetic is radiolabeled. In some embodiments, the peptide is radiolabeled or peptidomimetic using a radiometal. The radiometal can be attached to the peptide using a bifunctional chelating agent (BFCA). Examples of suitable radiometals for therapeutic treatment of diseases such as cancer include $^{111}$In, $^{64/67}$Cu, $^{90}$Y, $^{177}$Lu, and $^{213}$Bi. In some embodiments, the composition comprises a radiometal as a drug or payload that is targeted to a tissue by the peptide or peptidomimetic.

In some embodiments, the peptide or peptidomimetic is associated with a drug or payload as part of a vesicle or hollow sphere. In some embodiments, the vesicle is a liposome. In some embodiments, the liposome comprises phospholipids. In some embodiments, the liposome comprises polyethylene glycol. In some embodiments, the liposome comprises a lipid bilayer. In some embodiments, the liposome comprises two lipid bilayers. In some embodiments, a liposome has a diameter of at least 50 nm, at least 100 nm, at least 200 nm, at least 300 nm, at least 400 nm, at least 500 nm, at least 600 nm, at least 700 nm, at least 800 nm, at least 900 nm, at least 1000 nm, at least 2000 nm, at least 3000 nm, at least 4000 nm, or at least 5000 nm or higher. In some embodiments, a liposome has a diameter from about 50 nm to about 100 nm, from about 100 nm to about 200 nm, from about 200 nm to about 300 nm, from about 300 nm to about 400 nm, from about 400 nm to about 500 nm, from about 500 nm to about 600 nm, from about 600 nm to about 700 nm, from about 700 nm to about 800 nm, from about 800 nm to about 900 nm, from about 900 nm to about 1000 nm, from about 1000 nm to about 2000 nm, from about 2000 nm to about 3000 nm, from about 3000 nm to about 4000 nm, from about 4000 to about 5000 nm, or higher than about 5000 nm.

In some embodiments, the vesicle is a polymersome. Polymersomes are a type of vesicle made using amphiphilic synthetic block copolymers. Examples of suitable block copolymers include polyethylene glycol-polycaprolactone (PEG(5000)-PCL(10000)) and maleimide-polyethylene glycol-polycaprolactone (Mal-PEG(5000)-PCL(10000)). Polymers that can be used in making polymersomes include poly(ethylene glycol) (PEG/PEO), poly(2-methyloxazoline), polydimethylsiloxane (PDMS), polycaprolactone (PCL), polylactide (PLA), and polymethyl methacrylate (PMMA). In some embodiments, the liposome or polymersome comprises the peptide or peptidomimetic on the outer surface for binding to or recognition by a target molecule such as CD206.

In some embodiments, the peptide or peptidomimetic is conjugated to the block copolymers and then processed to form polymersomes containing the drug or payload. In some embodiments, a polymersome has a diameter of about 120 nm. In some embodiments, a polymersome has a diameter of at least 50 nm, at least 100 nm, at least 200 nm, at least 300 nm, at least 400 nm, at least 500 nm, at least 600 nm, at least 700 nm, at least 800 nm, at least 900 nm, at least 1000 nm, at least 2000 nm, at least 3000 nm, at least 4000 nm, or at least 5000 nm or higher. In some embodiments, a polymersome has a diameter from about 50 nm to about 100 nm, from about 100 nm to about 200 nm, from about 200 nm to about 300 nm, from about 300 nm to about 400 nm, from about 400 nm to about 500 nm, from about 500 nm to about 600 nm, from about 600 nm to about 700 nm, from about 700 nm to about 800 nm, from about 800 nm to about 900 nm, from about 900 nm to about 1000 nm, from about 1000 nm to about 2000 nm, from about 2000 nm to about 3000 nm, from about 3000 nm to about 4000 nm, from about 4000 to about 5000 nm, or higher than about 5000 nm.

In another aspect, disclosed herein are methods for treating cancer using targeted therapy. In some embodiments, the therapy is targeted to tumor tissue. In some embodiments, the therapy is targeted to solid tumor tissue. In some embodiments, the therapy is targeted to immune cells. In some embodiments, the therapy is targeted to macrophages. In some embodiments, the therapy is targeted to CD206-expressing cells. In some embodiments, the therapy is targeted to CD206-expressing M2 macrophages. In some embodiments, the therapy is targeted to CD206-expressing tumor-associated M2 macrophages. In some embodiments, the composition is used to perform chemotherapy. In some embodiments, the composition is used to perform immunotherapy. In some embodiments, the composition is used to perform radiation therapy. In some embodiments, the drug or payload comprises a chemotherapeutic agent. In some embodiments, the drug or payload comprises an antibody. In some embodiments, the drug or payload comprises a genetic vector such as a virus.

In certain embodiments, the methods of this disclosure comprise administering to a subject a composition comprising a drug or payload. In some embodiments, the methods provide a therapy including, for example, chemotherapy, radiation, an anti-cancer agent, or any combinations thereof. In some embodiments, the administered composition accumulates within tumor tissue such as solid tumor tissue. In some embodiments, the administered composition is targeted to tumor tissue through peptides that bind CD206-expressing macrophages infiltrating the tumor tissue. Anti-cancer agents include, but are not limited to, chemotherapeutic agents, radiotherapeutic agents, cytokines, immune checkpoint inhibitors, anti-angiogenic agents, apoptosis-inducing agents, anti-cancer antibodies and/or anti-cyclin-dependent kinase agents.

In some embodiments, the composition is administered in a liquid dosage form, a solid dosage form, a suppository, an inhalable dosage form, an intranasal dosage form, in a liposomal formulation, a dosage form comprising nanoparticles, a dosage form comprising microparticles, a polymeric dosage form, or any combinations thereof. In some embodiments, the composition comprises a drug or payload (e.g., immune checkpoint inhibitor, chemotherapeutic agent, radionuclide, etc.). In some embodiments, the composition comprising the drug or payload is administered by injection (such as subcutaneously or intravenously).

In some embodiments, the composition is administered over a period of about 1 week to about 2 weeks, about 2 weeks to about 3 weeks, about 3 weeks to about 4 weeks, about 4 weeks to about 5 weeks, about 6 weeks to about 7 weeks, about 7 weeks to about 8 weeks, about 8 weeks to about 9 weeks, about 9 weeks to about 10 weeks, about 10 weeks to about 11 weeks, about 11 weeks to about 12 weeks, about 12 weeks to about 24 weeks, about 24 weeks to about 48 weeks, about 48 weeks or about 52 weeks, or longer. In some embodiments, the composition is administered over a period of at least 1 week, at least 2 weeks, at least 3 weeks, at least 4 weeks, at least 6 weeks, at least 7 weeks, at least 8 weeks, at least 9 weeks, at least 10 weeks, 11, at least 12 weeks, at least 24 weeks, at least 48 weeks, or at least 52 weeks or longer. In some embodiments, the composition is administered once daily, twice daily, once every week, once every two weeks, once every three weeks, once every four weeks (or once a month), once every 8 weeks (or once every 2 months), once every 12 weeks (or once every 3 months), or once every 24 weeks (once every 6 months).

Examples of chemotherapeutic agents include alkylating agents, plant alkaloids, antitumor antibiotics, antimetabolites, topoisomerase I inhibitors, topoisomerase II inhibitors, and miscellaneous antineoplastics. Exemplary chemotherapeutic agents can include, without limitation, anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®), Ibrutinib, idelalisib, and brentuximab vedotin.

Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifext); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplext); Cyclophosphamide (Endoxant, Cytoxan®, Neosar®, Procytox®, Revimmune®); and Bendamustine HCl (Treanda®).

Exemplary anthracyclines can include, without limitation, e.g., doxorubicin (Adriamycin® and Rubex®); bleomycin (Lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin.

Exemplary vinca alkaloids include, but are not limited to, vinorelbine tartrate (Navelbine®), Vincristine (Oncovin®), and Vindesine (Eldisine R)); vinblastine (also known as vinblastine sulfate, vincaleukoblastine and VLB, Alkaban-AQ® and Velban®); and vinorelbine (Navelbine®).

Exemplary proteosome inhibitors can, but are not limited to, bortezomib (Velcade®); carfilzomib (PX-171-007, (S)-4-Methyl-N—((S)-1-(((S)-4-methyl-1-((R)-2-methyloxiran-2-yl)-1-oxopentan-2-yl)amino)-1-oxo-3-phenylpropan-2- yl)-2-4S)-2-(2-morpholinoacetamido)-4-phenylbutanamido)-pentanamide); marizomib (NPI-0052); ixazomib citrate (MLN-9708); delanzomib (CEP-18770); and O-Methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-L-serinamide (ONX-0912).

In some embodiments, immunotherapy comprises the destruction of tumor cells by directly targeting the tumor cells or indirectly stimulating immune responses. In some embodiments, immunotherapy comprises targeting immune molecular checkpoints using checkpoint receptor inhibitors, such as anti-T-lymphocyte-associated antigen 4 (CTLA-4), anti-Programmed Cell Death 1 (PD-1) antibodies, anti-T-cell immunoglobulin domain and mucin domain-3 (TIM-3), and anti-lymphocyte activation gene 3 (LAG3).

In some examples, the immunotherapy comprises an immune checkpoint activator, such as an agonist of costimulation by CD27 (e.g., an agonist antibody that binds to CD27), an agonist of costimulation by CD40 (e.g., an agonist antibody 10 that binds to CD40), an agonist of costimulation by OX40 (e.g., an agonist antibody that binds to OX40), an agonist of costimulation by GITR (e.g., an agonist antibody that binds to GITR), an agonist of costimulation by CD137 (e.g., an agonist antibody that binds to CD137), an agonist of costimulation by CD28 (e.g., an agonist antibody that binds to CD28), an agonist of costimulation by ICOS (e.g., an agonist antibody that binds to ICOS).

In some examples, the immunotherapy comprises an immune checkpoint inhibitor, such as an antagonist of PD-1 (e.g., an antagonist antibody that binds to PD-1), an antagonist of PD-L1 (e.g., an antagonist antibody that binds to PD-L1), an antagonist of CTLA-4 (e.g., an antagonist antibody that binds to CTLA-4), an antagonist of A2AR (e.g., an antagonist antibody that binds to A2AR), an antagonist of B7-H3 (e.g., an antagonist antibody that binds to B7-H3), an antagonist of B7-H4 (e.g., an antagonist antibody that binds to B7-H4), an antagonist of BTLA (e.g., an antagonist antibody that binds to BTLA), an antagonist of IDO (e.g., an antagonist antibody that binds to IDO), an antagonist of KIR (e.g., an antagonist antibody that binds to KIR), an antagonist of LAG3 (e.g., an antagonist antibody that binds to LAG3), an antagonist of TIM-3 (e.g., an antagonist antibody that binds to TIM3).

In some embodiments, the immunotherapy comprises an immune checkpoint regulator. In one example, the immune checkpoint regulator is TGN1412. In one example, the immune checkpoint regulator is NKTR-214. In one example, the immune checkpoint regulator is MEDI0562. In one example, the immune checkpoint regulator is MEDI6469. In one example, the immune checkpoint regulator is MEDI6383. In one example, the immune checkpoint regulator is JTX-2011. In one example, the immune checkpoint regulator is Keytruda (pembrolizumab). In one example, the immune checkpoint regulator is Opdivo (nivolumab). In one example, the immune checkpoint regulator is Yervoy (ipilimumab). In one example, the immune checkpoint regulator is tremelimumab. In one example, the immune checkpoint regulator is Tecentriq (atezolizumab). In one example, the immune checkpoint regulator is MGA271. In one example, the immune checkpoint regulator is indoximod. In one example, the immune checkpoint regulator is Epacadostat. In one example, the immune checkpoint regulator is lirilumab. In one example, the immune checkpoint regulator is BMS-986016. In one example, the immune checkpoint regulator is MPDL3280A. In one example, the immune checkpoint regulator is avelumab. In one example, the immune checkpoint regulator is durvalumab. In one example, the immune checkpoint regulator is MEDI4736. In one example, the immune checkpoint regulator is MEDI4737. In one example, the immune checkpoint regulator is TRX518. In one example, the immune checkpoint regulator is MK-4166. In one example, the immune checkpoint regulator is urelumab (BMS-663513). In one example, the immune checkpoint regulator is PF-05082566 (PF-2566).

FIGURE DESCRIPTIONS

FIG. 1. Identification of CSPGAKVRC ("UNO") in breast cancer mice. A, Naive phage library was injected intraperitoneally in 4T1 tumor-bearing mice and age-matched normal mice, and allowed to circulate for two h. Peritoneal cells were collected, the accompanying phages were rescued and the peptide-encoding segment of phage DNA was sequenced. B, Higher number of $CD206^+$ cells were seen in the 4T1 mice than normal mice. Peritoneal cells were extracted from the mice, seeded on coverslips, allowed to attach for 2 h, fixed, permeabilized, and stained for CD206. $CD206^+$ cells were counted from 6 different confocal images, 2 from each mouse. C, Highly repeated sequences obtained from the first round of the biopanning experiment shown schematically in panel A. D, Frequency of phage clones encoding UNO or a randomly picked peptide (CIGVSSDC) divided by the total number of repeated sequences) in the 4T1 tumor-bearing and normal mice.

Figure 25:
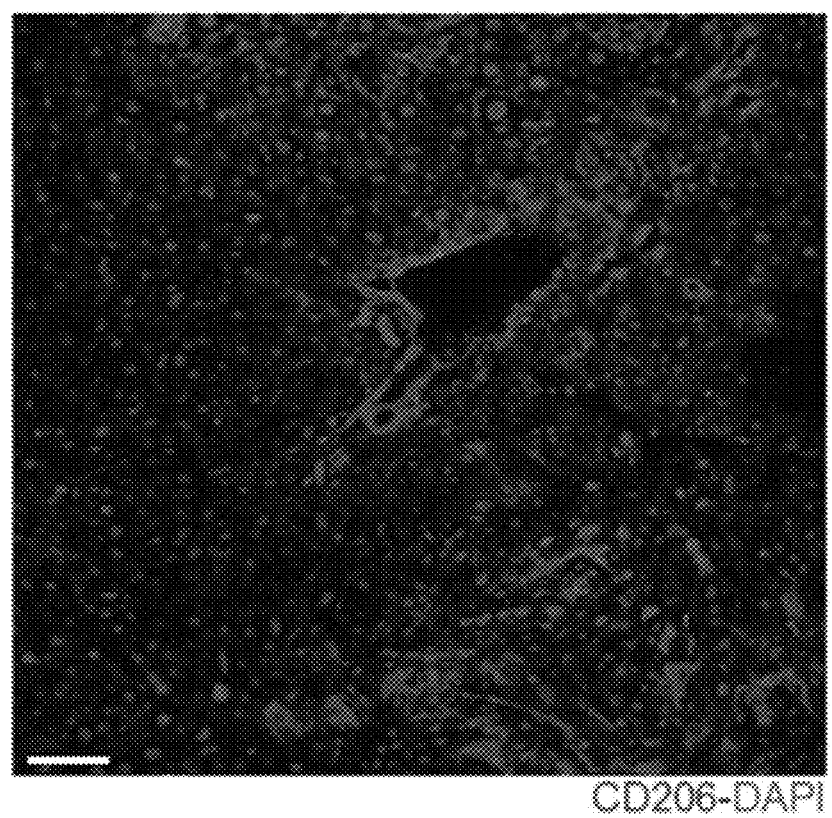
FIG. 25 shows a liver section from a 4T1 tumor mouse imaged using higher gain than in FIG. 2.

FIG. 2. FAM-UNO accumulates in $CD206^+$, $TIE2^+$ macrophages in breast tumors and lymph node. Thirty nmoles of FAM-UNO or FAM-CRKQGEAKC (SEQ ID NO: 5) control peptide were injected intravenously into 4T1 tumor-bearing mice and allowed to circulate for 2 h. Mice were then sacrificed and tumor and tissues were analyzed by immunofluorescence using rabbit anti-FAM (green) and rat anti-CD206 or rat anti-TIE2 (red) antibodies, and counterstained with DAPI. All images were taken under the same imaging conditions. FAM-UNO accumulated in macrophages within tumors and lymph nodes positive for CD206 staining (A, B, C) and TIE2 (D, and H: Blow up of D). FAM-UNO showed very low accumulation in the liver (E), but signal was seen in the kidneys (F), which is the normal excretion route for peptides. No signal or only traces of FAM-UNO were observed in the spleen, heart and lungs in images taken under the same conditions (shown in FIG. 10). To ascertain that anti-CD206 is capable of detecting CD206 in the liver, an image was acquired with longer exposure time from an uninjected animal (FIG. 25). The charge matched control peptide, CRKQGEAKC (SEQ ID NO: 5), did not give any signal in $CD206^+$ macrophages or elsewhere in the tumor (G and I). Green: FAM-peptide; Red: CD206 or TIE2, Blue: DAPI. Representative fields from multiple sections prepared from at least 3 tumors (n≥3 mice) are shown. The graph in panel I shows mean+SEM of FAM signal quantified as described in materials and methods Scale bars: 100 μm for A, B, C, E, F, G and 50 μm for D and H.

FIG. 3. FAM-UNO accumulates in $CD206^+$ macrophages in glioblastoma, gastric carcinoma, and melanoma. Thirty nmoles of FAM-UNO or FAM-control peptide were injected intravenously into mice and allowed to circulate for 2 h. Mice were then sacrificed and tumor and tissues were analyzed by immunofluorescence using rabbit anti-FAM (green) and rat anti-CD206 (red) antibodies, and counterstained with DAPI. A, Homing to glioblastoma (WT-GBM).

Figures 15A, 15B, 15C:
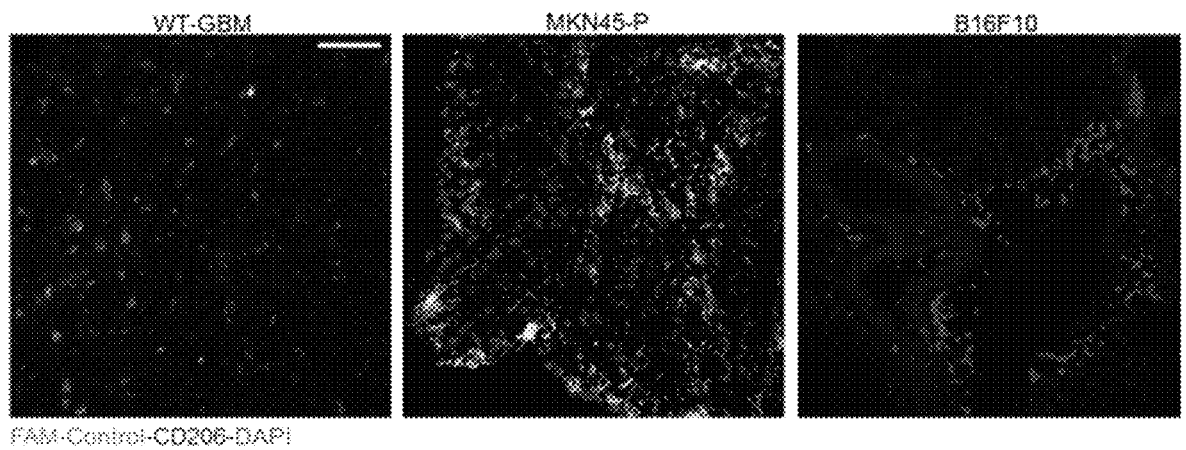
FIG. 15 shows FAM-control peptide (CRKQGEAKC; SEQ ID NO: 5) does not accumulate in MEMs in gastric carcinoma (FIG. 15B), glioblastoma (FIG. 15A) and melanoma (FIG. 15C) tumors using immunofluorescence.

Signal was seen exclusively within the tumor (T) and not in brain parenchyma (BP). B, Homing to a peritoneal carcinomatosis lesion (PCL) induced by i.p. inoculation of gastric carcinoma cell line MKN4-5P. C, Homing to experimental melanoma metastases in the lungs. The metastases were induced by i.v. inoculation of B16F10 melanoma cells. FAM signal was seen in lung metastases (LMM), and not in noncancerous lung parenchyma (LP). The arrows point to examples of FAM and CD206 colocalization in each panel. The insets show CD206-positive individual cells with internalized FAM-UNO signal. A parallel experiment with the control peptide (FAM-Control) is shown in FIG. 15A-C; images of spleens from mice injected with FAM-Control peptide are shown in FIG. 19. Blue: DAPI. Representative fields from multiple sections (n≥3) prepared from at least 3 tumors are shown. Scale bar: 50 µm. Images shown are representative fields from multiple sections (≥3) prepared from at least 3 tumors (n≥3 mice). The graphs show mean+SEM of FAM signal quantified as described in Materials and Methods.

FIG. 4. UNO specificity for CD206. A, Change in fluorescence anisotropy of FAM-UNO (dotted line) and FAM-UNO in DTT (solid line) while incubating with mouse recombinant CD206. B, Change in fluorescence anisotropy of FAM-CSPGAK with mouse recombinant CD206 (solid line) or with CD163 (dotted line) and of FAM-CPMTDNE (control) with CD206 (dashed line). C, FAM-UNO binds selectively to CCR2$^+$ macrophages collected from the peritoneal cavity of 4T1 tumor-bearing mice, as 94.3% of FAM cells are CCR2$^+$ cells. The analysis was done gating for the FAM population (left panel). In these 4T1 tumor bearing mice, 58% of peritoneal cells are macrophages, i.e. CCR2$^+$ cells (right panel). D, FAM-UNO binding to peritoneal cells is inhibited by preincubating with 10 µg/mL of anti-CD206, whereas the preincubation with anti CD206 antibody had no effect on FAM-LyP-1 binding. In panels A and D are shown representative graphs from three independent experiments. In panels c and d are shown results from three independent experiments (n=3 mice) and bars of panel D represents mean+SEM.

FIG. 5. A, Characterization of FAM-UNO derivatized, paclitaxel loaded, polymeric vesicles ("FAM-UNO-NP-PTX"). Transmission electron microscopy images (two panels on the left, scale bar: 200 nm) and Dynamic Light Scattering profile (right panel). Polymeric vesicles are composed of the copolymer polyethylene glycol-polycaprolactone. B, C, FAM-UNO guides cargo-loaded nanoparticles inside MEMs. FAM-UNO-NP-PTX were intravenously injected in mice bearing MCF-7 tumors, 21 days after orthotopic inoculation of 5×10$^6$ cells. The particles were allowed to circulate for 6 h. The mice were then sacrificed, and tumors and tissues were analyzed by immunofluorescence using rabbit anti-FAM (green) and rat anti-CD206 (red) antibodies and counterstained with DAPI (blue). Images shown are representative fields from multiple sections (3) prepared from 3 tumors (n=3 mice).

Figure 6A:
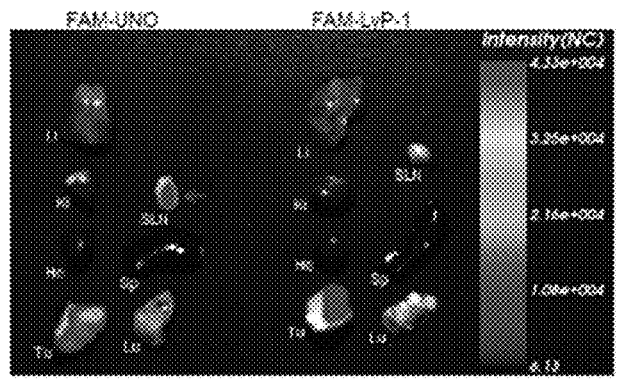
FIG. 6A shows mouse organs imaged for FAM-UNO or FAM-1-LyP-1 using a live imaging system in FITC.
Figure 6B:
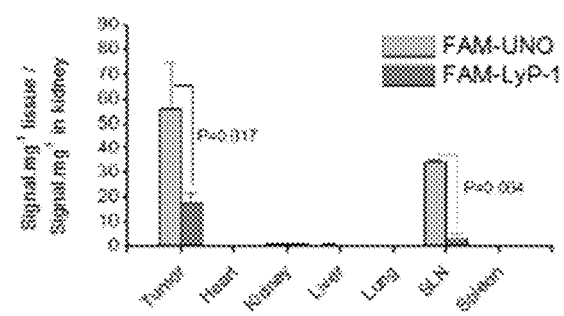
FIG. 6B shows the quantification of the signal in each organ from FIG. 6A.

FIG. 6. FAM-UNO can be used to image metastasis-draining lymph nodes. A, FAM-UNO and FAM-LyP-1 were injected i.p. at doses of 30 nmoles in 4T1 tumor-bearing mice. Peptides were allowed to circulate for two h, mice were then sacrificed, and the organs were collected and imaged with the live imaging system MX3 Art Optix in the FITC channel with laser excitation. B, The signal in each organ was quantified, normalized to the tissue weight and the ratio tissue/kidney was graphed in bar graph. LyP-1 is a peptide that targets p32 protein on the surface of activated macrophages. Results from n=3 mice. Bars of panel B represent mean+SEM.

Figure 7:
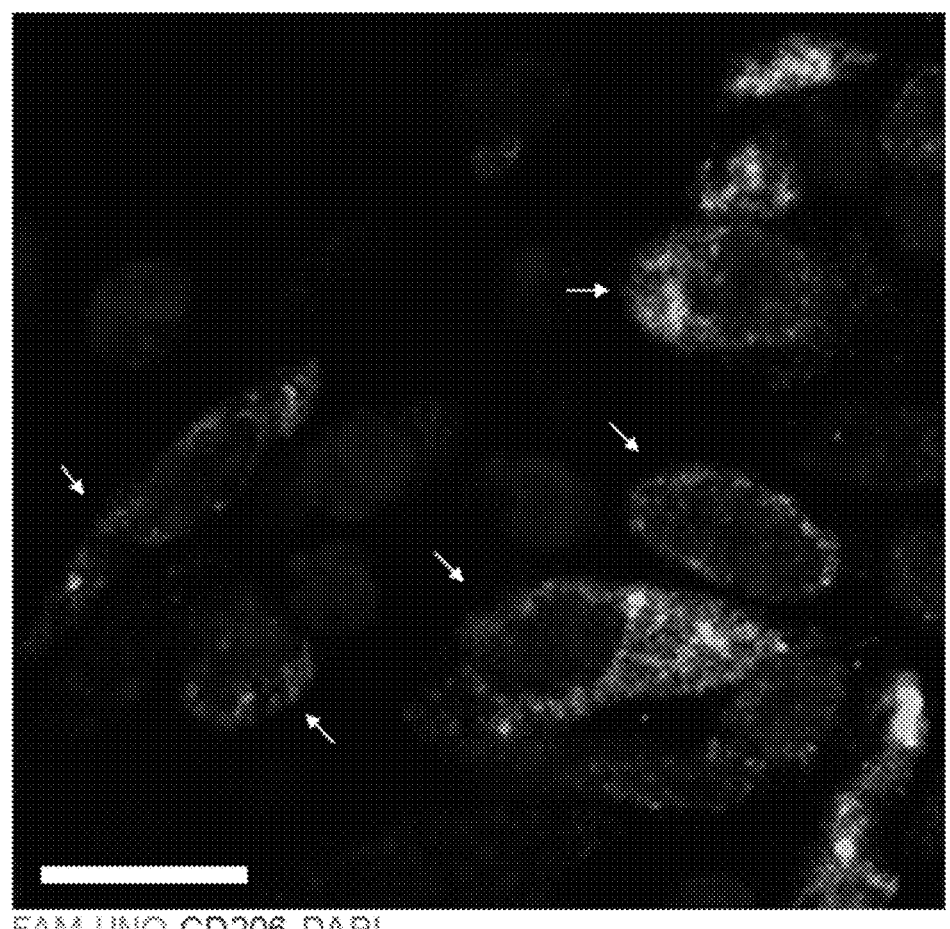
FIG. 7 shows confocal microscopy imaging of FAM-UNO in MEMs.

FIG. 7. Confocal microscopy using low optical thickness and high magnification, of FAM-UNO in MEMs. Thirty nmoles of FAM-UNO were injected intravenously into 4T1 tumor-bearing mice and allowed to circulate for 2 hours. Mice were then sacrificed and tumors were analyzed by immunofluorescence using rabbit anti-FAM (green) and rat anti-CD206. Sections were imaged using 0.9 µm optical thickness at 63×. Scale bar: 10 µm. Representative image from n=3 mice. FAM and CD206 showed significant colocalization (arrows). For 3D reconstruction of FAM-UNO in MEM, thirty nmoles of FAM-UNO were injected intravenously into 4T1 tumor-bearing mice and allowed to circulate for 2 hours. Mice were then sacrificed and tumors were analyzed by immunofluorescence using rabbit anti-FAM (green) and rat anti-CD206 (red). Then, Z-stack images were taken using 0.9 µm optical thickness at 63× and spaced 1 µm apart and three dimensionally reconstructed using ImageJ.

Figure 8:
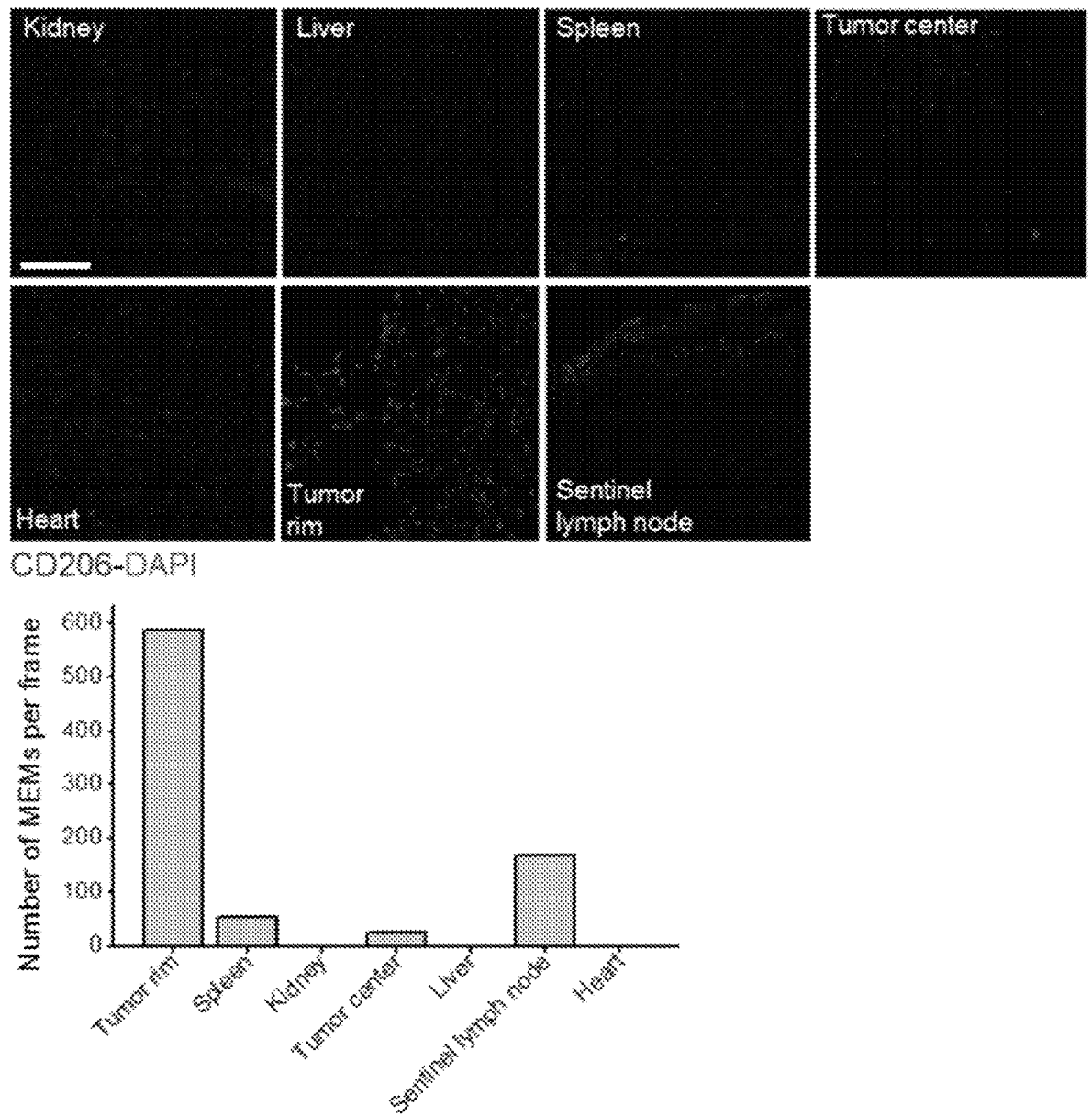
FIG. 8 shows fluorescence imaging of MEMs which highly overpopulate the tumor rim and are abundant in a sentinel lymph node.

FIG. 8. MEMs highly overpopulate the tumor rim and are abundant in a sentinel lymph node. Tumor and organs from a 4T1 tumor mouse were stained for CD206, using rat anti-CD206 (red) and counterstained with DAPI (blue). Scale bar: 100 µm. Representative images from n=3 mice. The tumor rim and sentinel lymph node exhibited significant CD206 staining.

Figure 9:
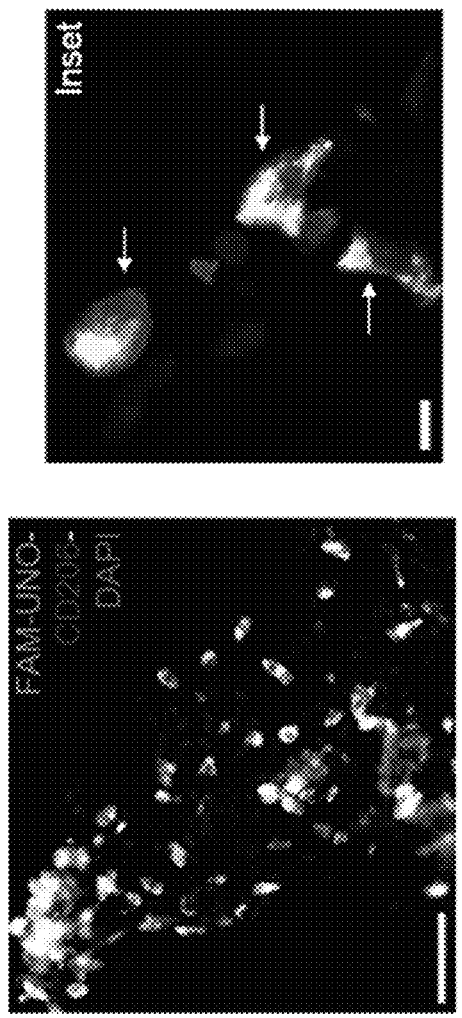
FIG. 9 shows fluorescence imaging of FAM-UNO accumulation in MEMs in 4T1 breast cancer tissue.

FIG. 9. FAM-UNO accumulates in MEMs after 12-hour circulation in 4T1 breast cancer. Thirty nmoles of FAM-UNO were injected intravenously in mice bearing 4T1 tumors, 10 days after orthotopic inoculation of 10$^6$ cells. Peptide was allowed to circulate for 12 hours. Mice were then sacrificed, and tumor and tissues analyzed by immunofluorescence using rabbit anti-FAM (green) together with rat anti-CD206 (red) and counterstained with DAPI (blue). Scale bars: 50 µm (left) and 10 µm (right). Representative images from n=3 mice.

Figure 10:
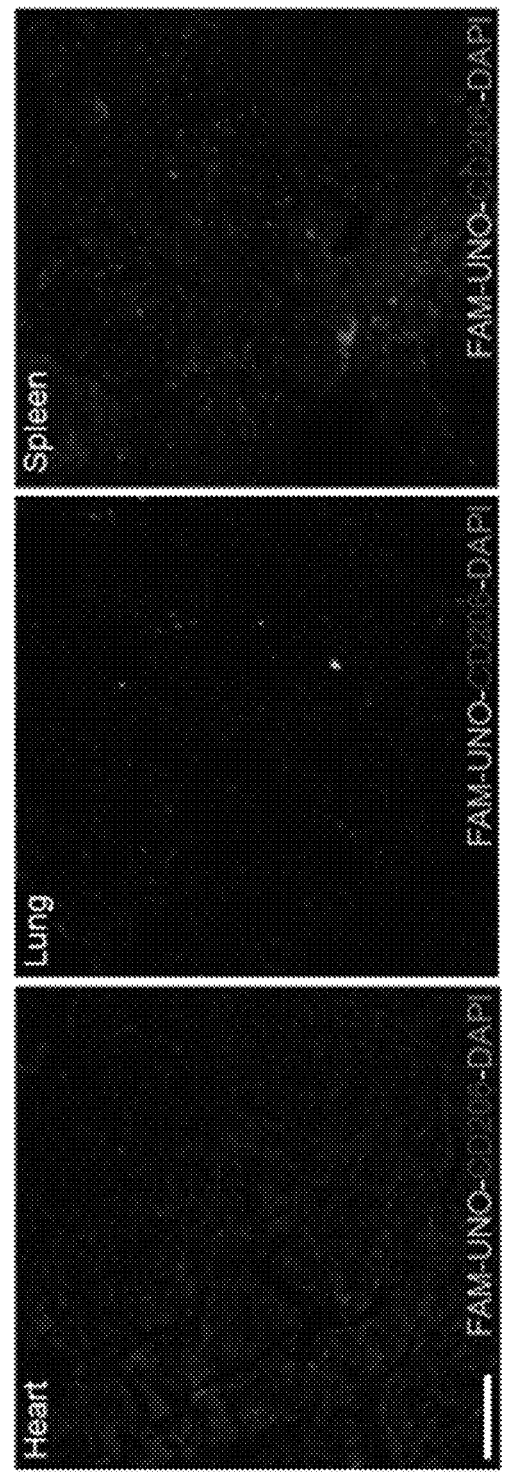
FIG. 10 shows fluorescence imaging indicating that FAM-UNO does not accumulate in heart, lung and spleen.

FIG. 10. FAM-UNO does not accumulate in heart, lung and spleen. Heart, lung and spleen of FIG. 2. Scale bar: 100m. Representative images from n=3 mice.

FIG. 11. FAM-UNO accumulates in MEMs in MCF-7 breast cancer. A, Thirty nmoles of FAM-UNO were injected intravenously in mice bearing MCF-7 tumors, 21 days after orthotopic inoculation of 5×10$^6$ cells. The peptide was allowed to circulate for 2 hours, the mouse was then sacrificed, and the tumor and tissues were analyzed by immunofluorescence using rabbit anti-FAM (green), rat anti-CD206 (red) and counterstained with DAPI (blue). All images were taken with the same imaging conditions. Scale bar: 100 µm and 50 µm (blow up). FAM-UNO and CD206 showed significant colocalization (circled). B, FAM-UNO does not home to cancer cells. The tumor tissue from panel A was analyzed by immunofluorescence using rabbit anti-FAM (green), rat anti-HLA ABC (red) and counterstained with DAPI (blue). Scale bar: 50 µm. C, MCF-7 tumors are leaky. Tumor sections were immunostained for endogenous mouse IgG and counterstained with DAPI using the same staining and imaging conditions as in FIG. 17. Scale bar: 100 µm. Representative images from n=3 mice. FAM-UNO (arrowheads) did not localize to the same cells as HLA ABC (arrows).

FIG. 12. FAM-UNO is internalized by perivascular cells in WT-GBM tumor. Thirty nmoles of FAM-UNO were injected intravenously in tumor mice. Peptide was allowed to circulate for 2 hours. Mice were then sacrificed and tumor and tissues were analyzed by immunofluorescence using rabbit anti-FAM (green, arrows) together with rat anti-CD31

(blood vessels; red, double-headed arrow) and counterstained with DAPI. Scale bar: 20 µm. Representative images from n=3 mice.

Figure 13:
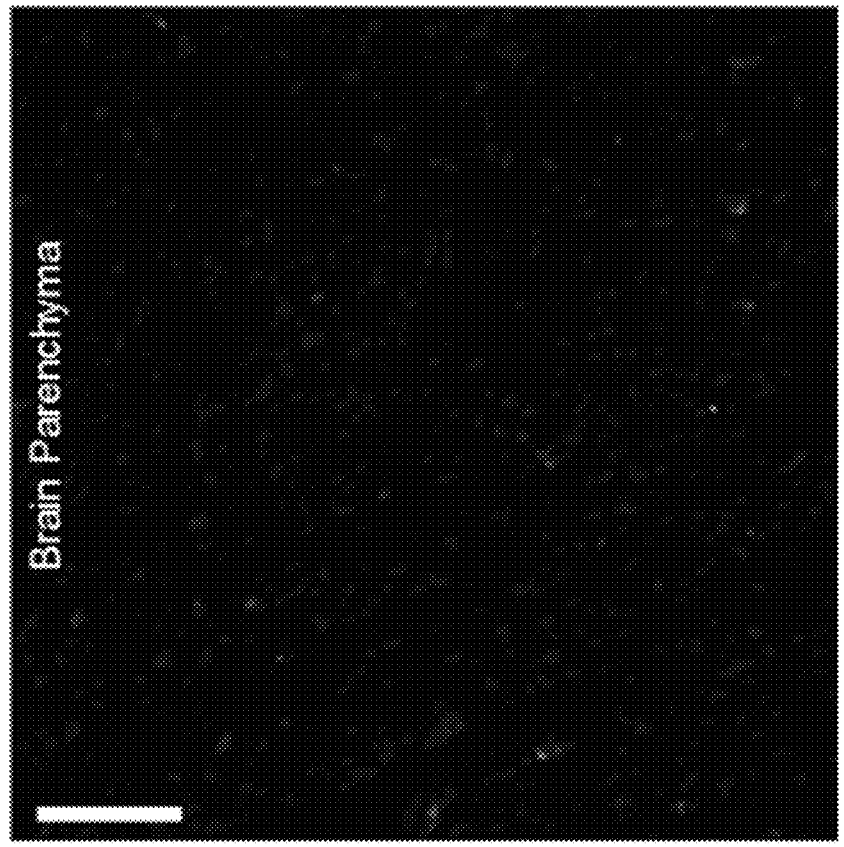
FIG. 13 shows fluorescence imaging of FAM-UNO in brain parenchyma.

FIG. 13. FAM-UNO does not home to brain parenchyma. The contralateral side of the brain shown in FIG. 3A stained and imaged under the same conditions as in FIG. 3A. Scale bar: 50 µm. Representative images from n=3 mice. Almost no FAM or CD206 was detected.

Figure 14:
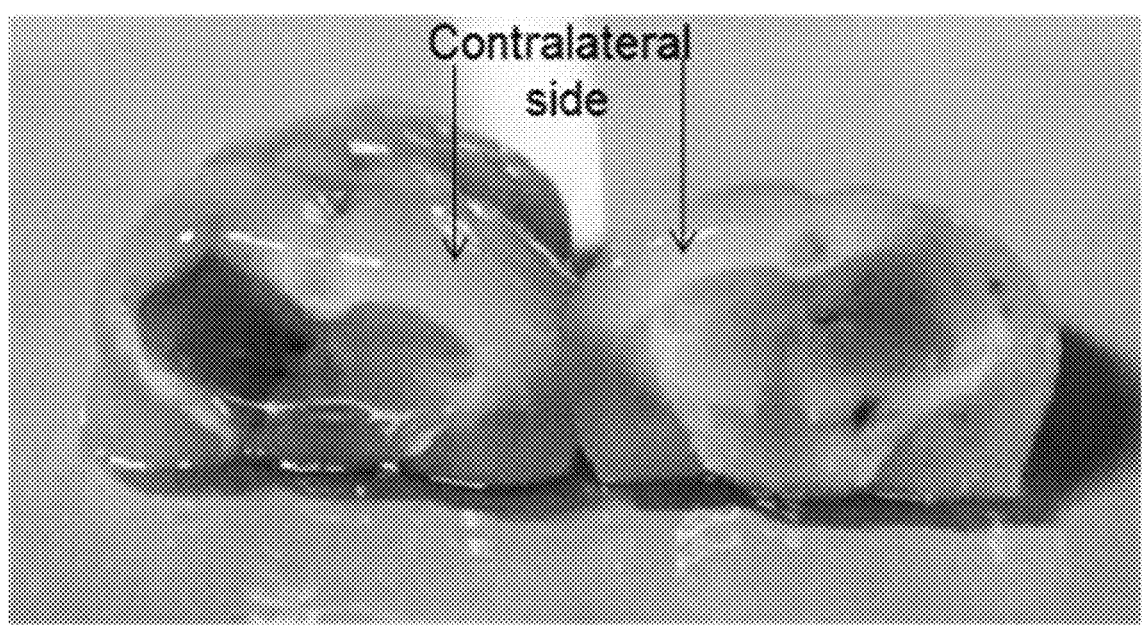
FIG. 14 shows a photographic image of mouse brains showing Evans blue staining within the brains seven days following orthotopic implantation of WT-GBM cells.

FIG. 14. WT-GBM tumors are leaky. Seven days after orthotopic implantation of WT-GBM cells, mice were intravenously injected with 1004, of 0.5% Evans blue solution in PBS and allowed to circulate for 1 h. Mice were then perfused with PBS and brains were extracted and photographed. Representative images from n=3 mice.

FIG. 15. FAM-control peptide does not accumulate in MEMs in gastric carcinoma, glioblastoma and melanoma tumors. Thirty nmoles of FAM-CRKQGEAKC (SEQ ID NO: 5) were injected intravenously in mice. The peptide was allowed to circulate for 2 hours. Mice were then sacrificed, and tumor and tissues analyzed by immunofluorescence using rabbit anti-FAM (green) together with rat anti-CD206 (red), and counterstained with DAPI. FAM-CRKQGEAKC (SEQ ID NO: 5) injections were made at the same day after tumor inoculation as FAM-UNO injections in FIG. 4, and the images were taken under the same conditions. Scale bar: 100 µm. Representative images from n=3 mice. Little to no FAM-Control peptide was observed in the tumors and tissues of WT-GBM and B16F10 injected mice (FIG. 15A, FIG. 15C). Some FAM-Control peptide was observed in the MKN45-P injected ice, but the signal did not colocalize with CD206 (FIG. 15B).

Figure 16:
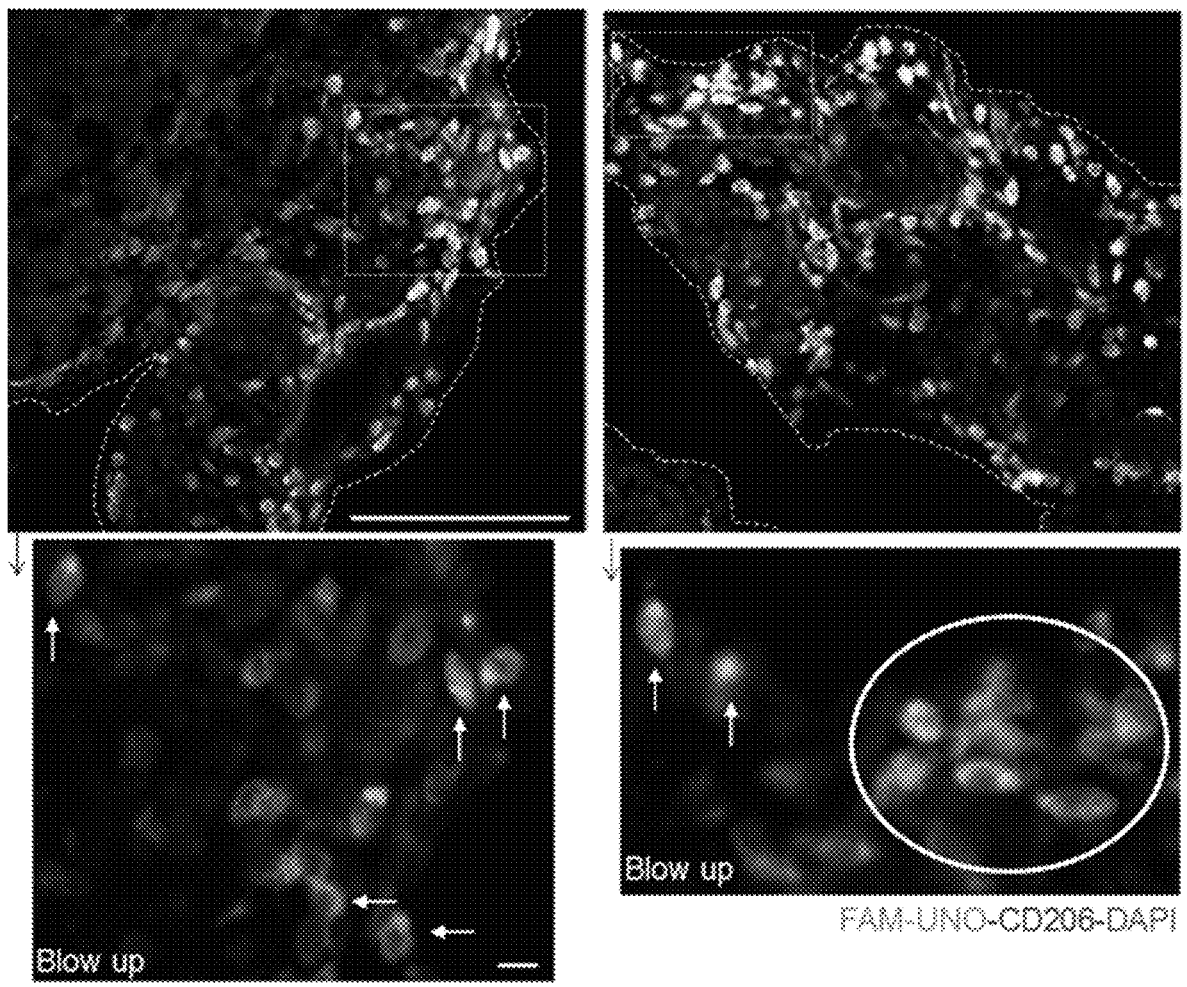
FIG. 16 shows that FAM-UNO homes to MEMs in the rim of MKN45-P tumor nodules.

FIG. 16. FAM-UNO homes to MEMs in the rim of MKN45-P tumor nodules. Thirty nmoles of FAM-UNO were injected intravenously in mice. The peptide was allowed to circulate for 2 hours. The mice were then sacrificed and the tumors and tissues were analyzed by immunofluorescence using rabbit anti-FAM (green) together with rat anti-CD206 (red), and counterstained with DAPI. FAM-UNO and CD206 signals showed significant colocalization (see arrows and circle in bottom zoomed in panels). Scale bar: 100 µm and 10 µm (blow up). Representative images from n=3 mice.

Figure 17:
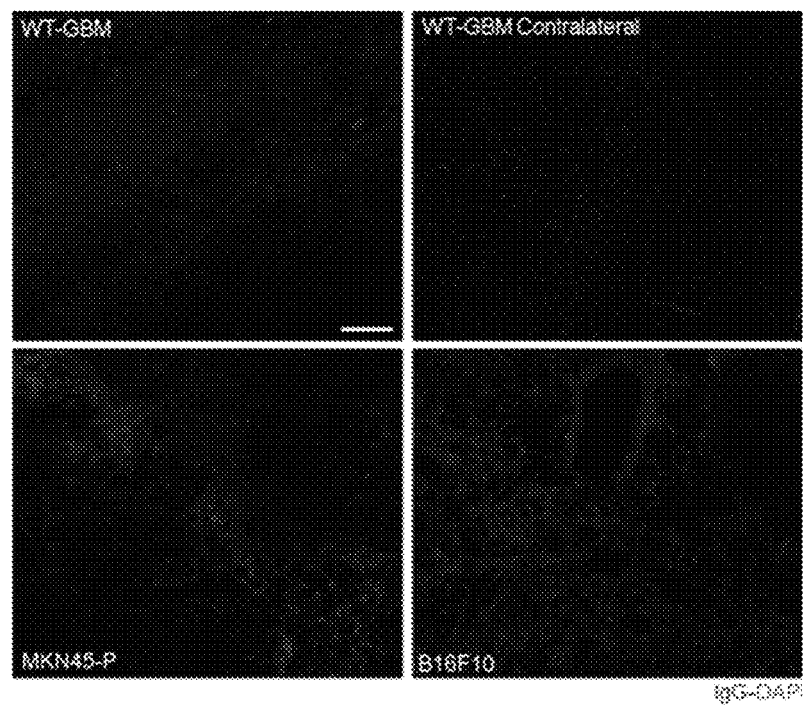
FIG. 17 shows endogenous IgG immunostaining (red) of WT-GBM, MKN45-P and B16F10 tumors.

FIG. 17. Endogenous IgG immunostaining (red) of WT-GBM, MKN45-P and B16F10 tumors. Scale bar: 100 µm. Representative images from n=3 mice.

Figure 18:
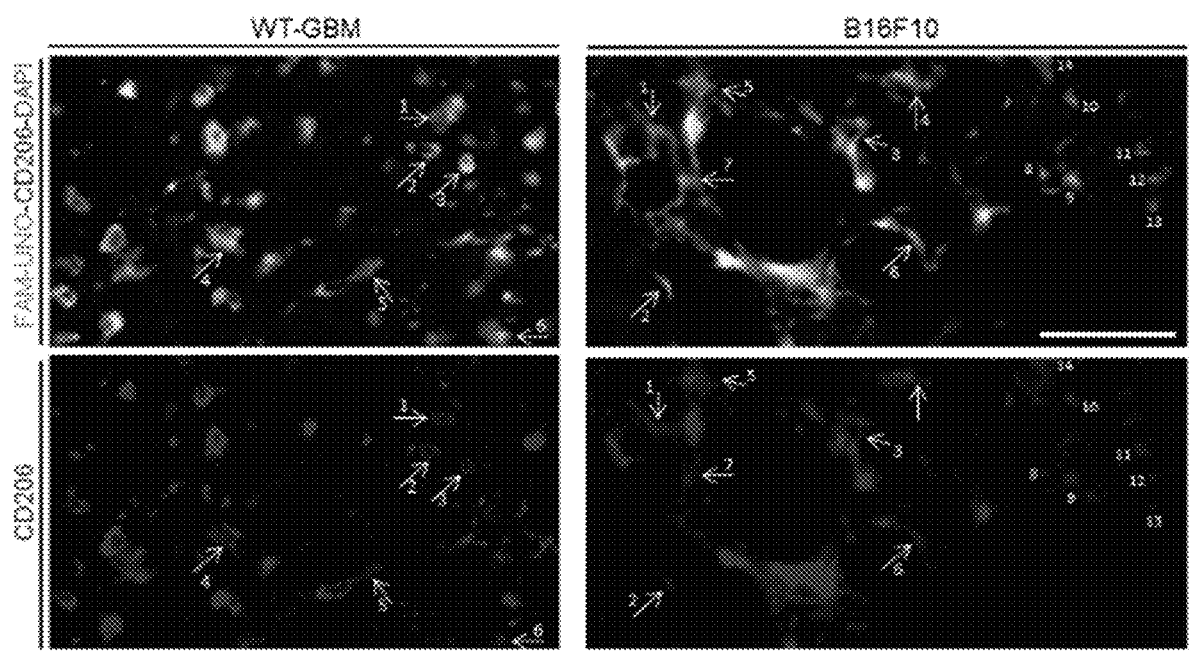
FIG. 18 shows the coincidence between FAM-UNO⁺ and CD206⁺ structures in WT-GBM and B16F10 tumors using fluorescence imaging.

FIG. 18. Coincidence between FAM-UNO+ and CD206+ structures in WT-GBM and B16F10 tumors, where CD206 (red) channel is shown separately. Arrows point to regions that at first sight seem green in the merged image. Scale bar: 50 µm. Representative images from n=3 mice.

Figures 19A, 19B, 19C:
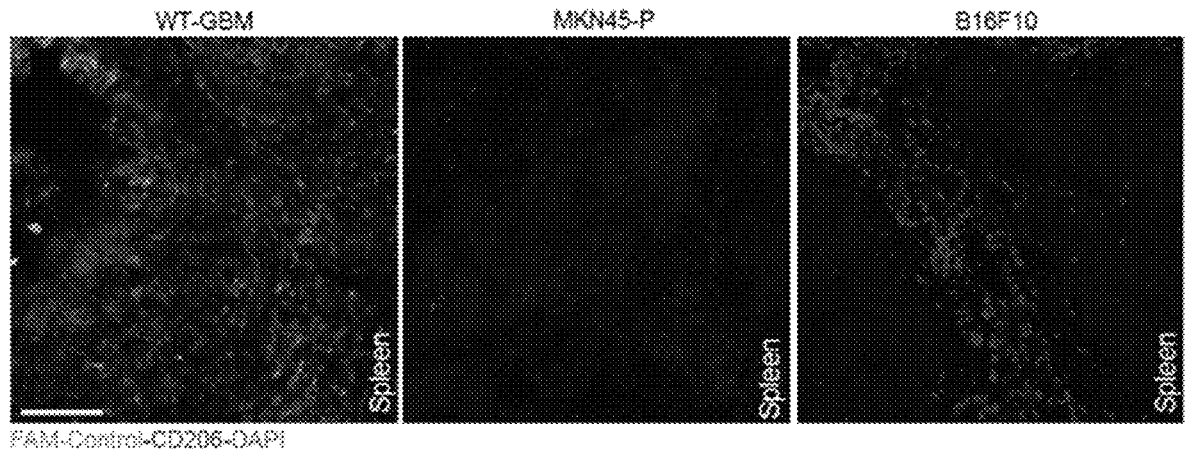
FIG. 19 shows that FAM-Control peptide does not accumulate in the spleen of gastric carcinoma, glioblastoma or melanoma tumor mice using fluorescence imaging.

FIG. 19. FAM-Control does not accumulate in the spleen of gastric carcinoma, glioblastoma or melanoma tumor mice. Thirty nmoles of FAM-Control were injected intravenously in mice. The peptide was allowed to circulate for 2 hours. The mice were then sacrificed, and the tumors and tissues were analyzed by immunofluorescence using rabbit anti-FAM (green) together with rat anti-CD206 (red), and counterstained with DAPI. Both CD206 and FAM were present in WT-GBM cells, but the respective fluorescence signals had low correlation with the strongest CD206 signal in the upper left quadrant and the strongest FAM signal in the lower right quadrant (FIG. 19A). MKN45-P cells showed almost no signal for CD206 or FAM (FIG. 19B). B16F10 cells had a strong CD206 signal but no detectable FAM signal (FIG. 19C). All images were taken under the same conditions as those of FIG. 4. Scale bar: 100 µm. Representative images from n=3 mice.

Figure 20:
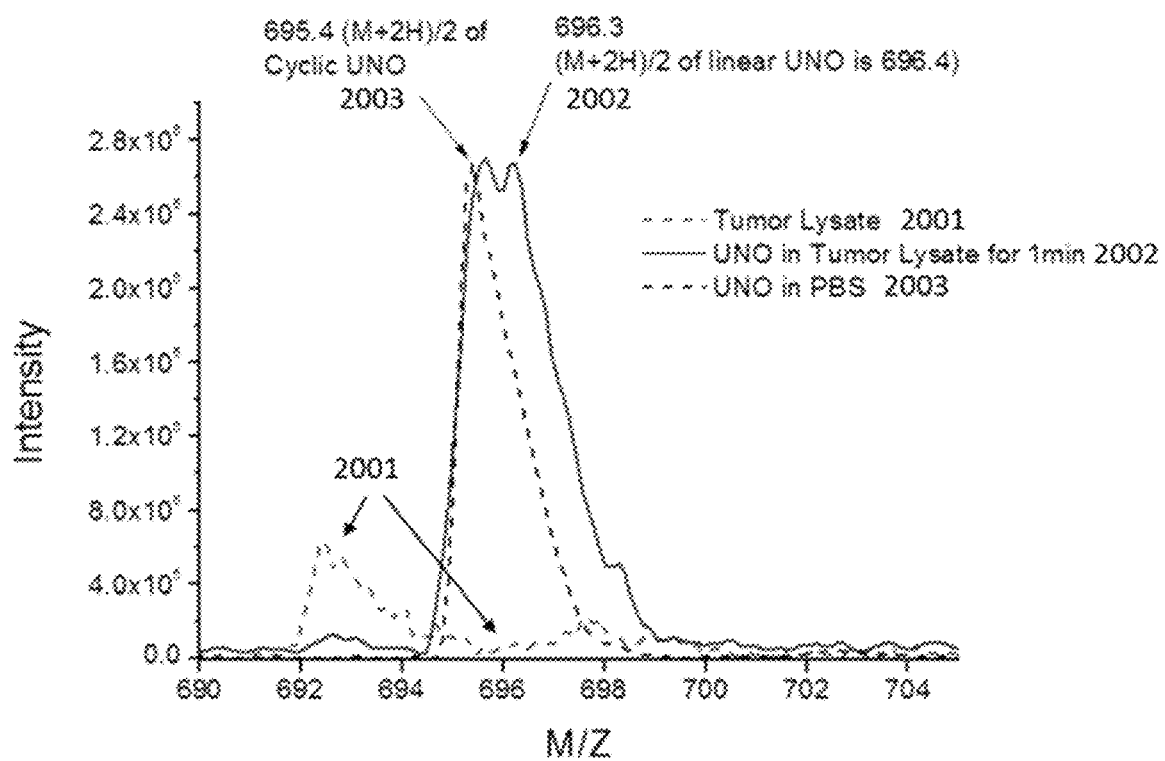
FIG. 20 shows the mass spectra indicating FAM-UNO gets linearized in presence of orthotopic 4T1 tumor lysate.

FIG. 20. FAM-UNO gets linearized in presence of orthotopic 4T1 tumor lysate. Mass spectra region m/z 690-705 for retention period 11.5-13.0 min, which corresponds to the retention of FAM-UNO (blue dotted line, 2003). [M+2H]2+ with m/z=695.4 was chosen as the representative signal for having the highest signal to noise ratio of all FAM-UNO related signals. Orthotopic 4T1 tumor lysate (green dotted line, 2001) lacks constituents with m/z 694-700 eluting at the same time frame. On the first minute upon FAM-UNO addition to tumor lysate the signal from the peptide (red solid line, 2002) is broadened, due to appearance of another peak with maximum intensity at 696.3. The new signal corresponds to a compound with two additional hydrogens compared with cyclic FAM-UNO.

Figure 21:
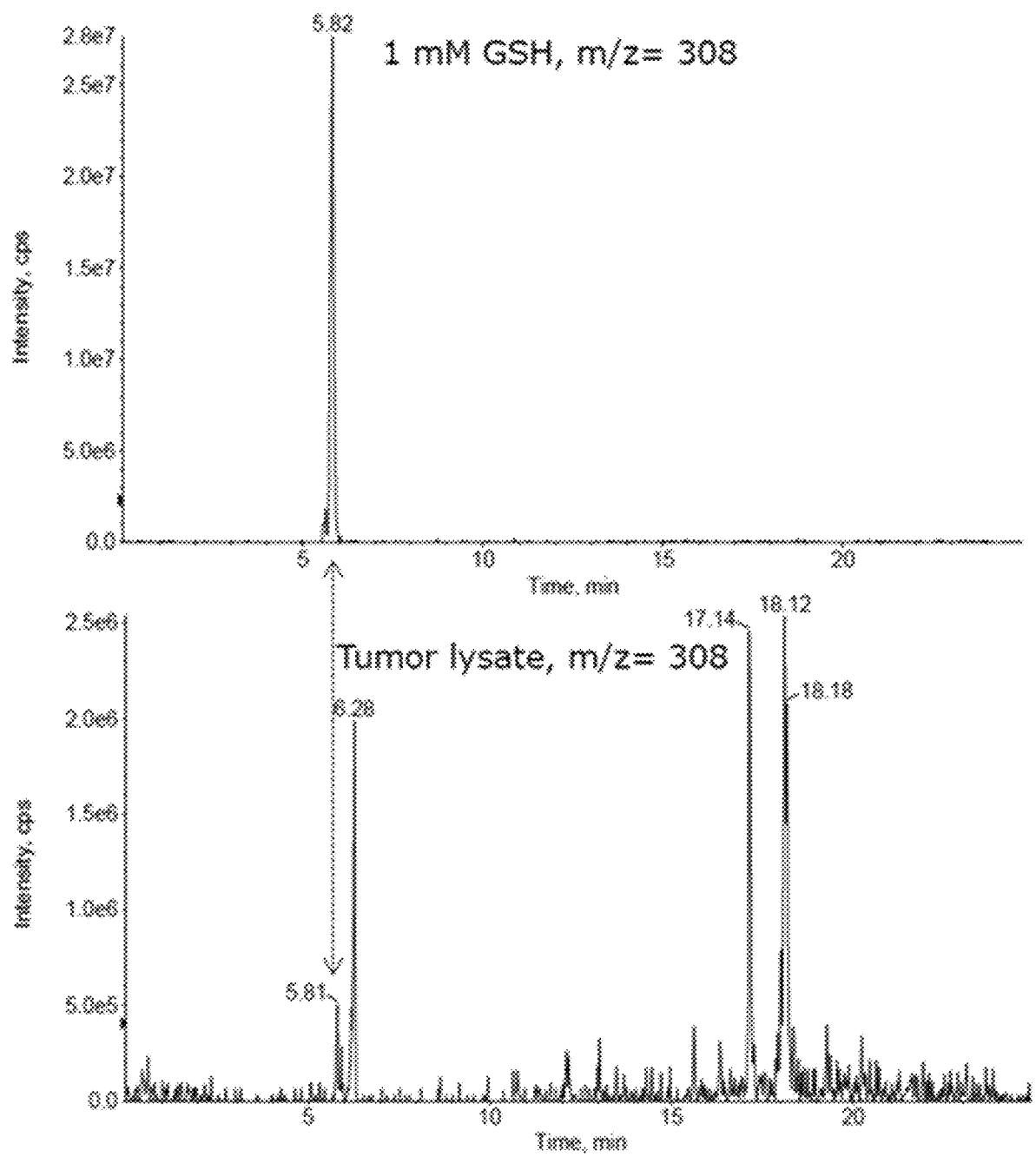
FIG. 21 shows mass spectra indicating the presence of Glutathione (GSH) in orthotopic 4T1 tumor lysate.

FIG. 21. Presence of Glutathione (GSH) in orthotopic 4T1 tumor lysate. Upper panel: chromatogram of m/z=308 (this mass corresponds to GSH molecular ion [M+H]+) on 1 mM GSH solution, showing the retention time (5.8 min) for GSH. Lower panel: chromatogram of m/z=308 on tumor lysate, showing a retention peak at 5.8 min, which is the same retention time as for pure GSH.

Figure 22:
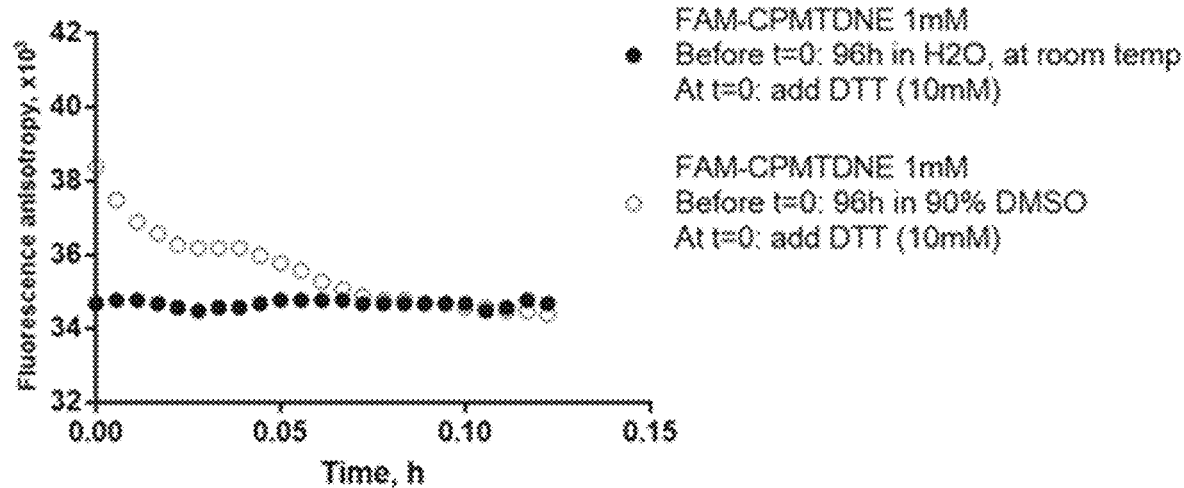
FIG. 22 shows a fluorescence anisotropy profile indicating FAM-CPMTDNE (SEQ ID NO: 7) does not dimerize in water.

FIG. 22. FAM-CPMTDNE does not dimerize in water. FAM-CPMTDNE peptide was preincubated in 90% DMSO for 4 days at room temperature to enhance the disulphide bond formation (open circles). The observed higher FA signal in comparison with peptide kept in H2O (filled circles) is caused by a rotational mobility decrease due to a mass increase upon dimer formation in DMSO. Addition of DTT caused time-dependent decrease of FA signal, linked to the dissociation of the dimer to FAM-CPMTDNE monomers.

Figure 23A:
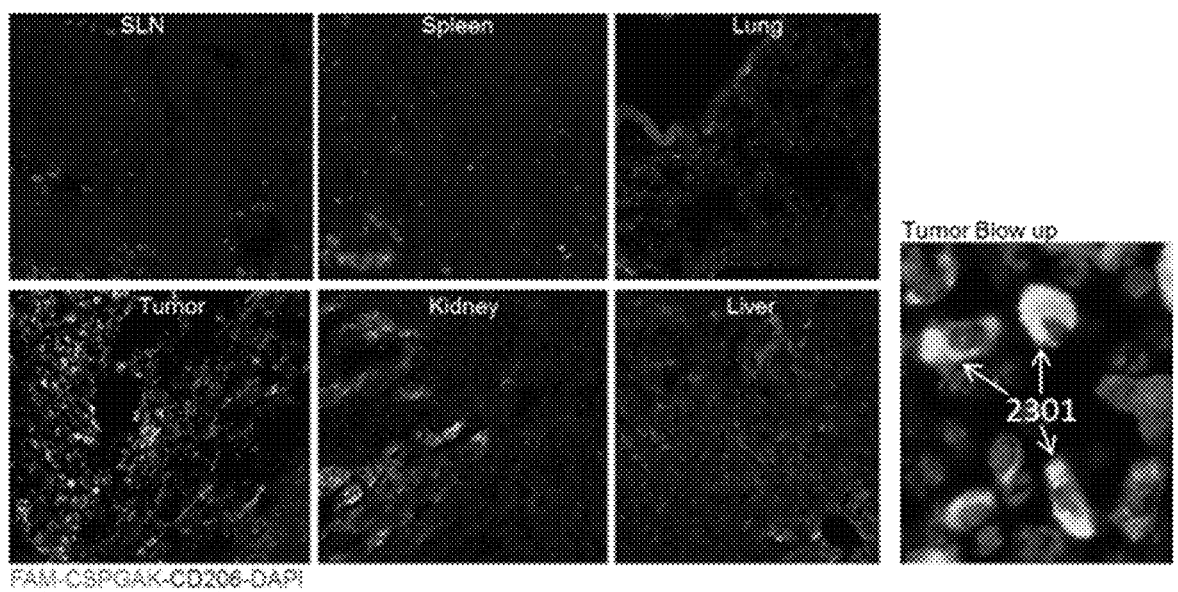
FIG. 23A shows colocalization of FAM-CSPGAK (SEQ ID NO: 6) and CD206.
Figure 23B:
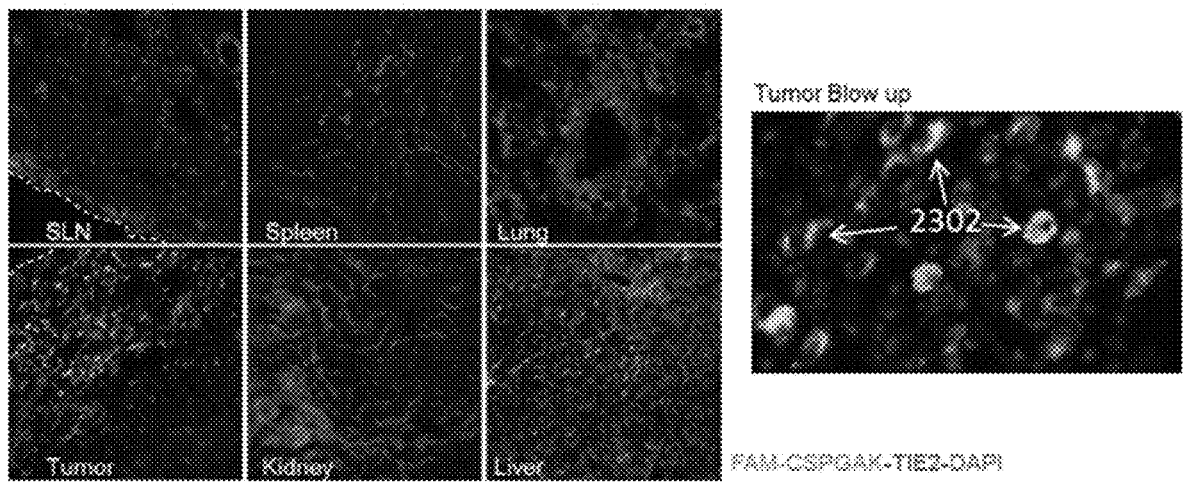
FIG. 23B shows colocalization of FAM-CSPGAK (SEQ ID NO: 6) and TIE2.

FIG. 23. FAM-CSPGAK accumulates in MEMs. Thirty nmoles of FAM-CSPGAK were injected intravenously in mice bearing 4T1 tumors, 10 days after orthotopic inoculation of $10^6$ Cells. Peptide was let to circulate for two hours, mice were then sacked and tumor and tissues analyzed by immunofluorescence using rabbit anti-FAM (green) together with rat anti-CD206 (FIG. 23A) or anti-TIE2 (FIG. 23B) (red), which are both markers of MEMs and counterstained with DAPI (Blue). The "Tumor blow up" panels show zoomed in views of the tumor tissues with cells having fluorescence signals showing co-localization of FAM and CD206 (2301) or FAM and TIE2 (2302). All images were taken with the same imaging conditions. Representative images from n=3 mice.

Figure 24:
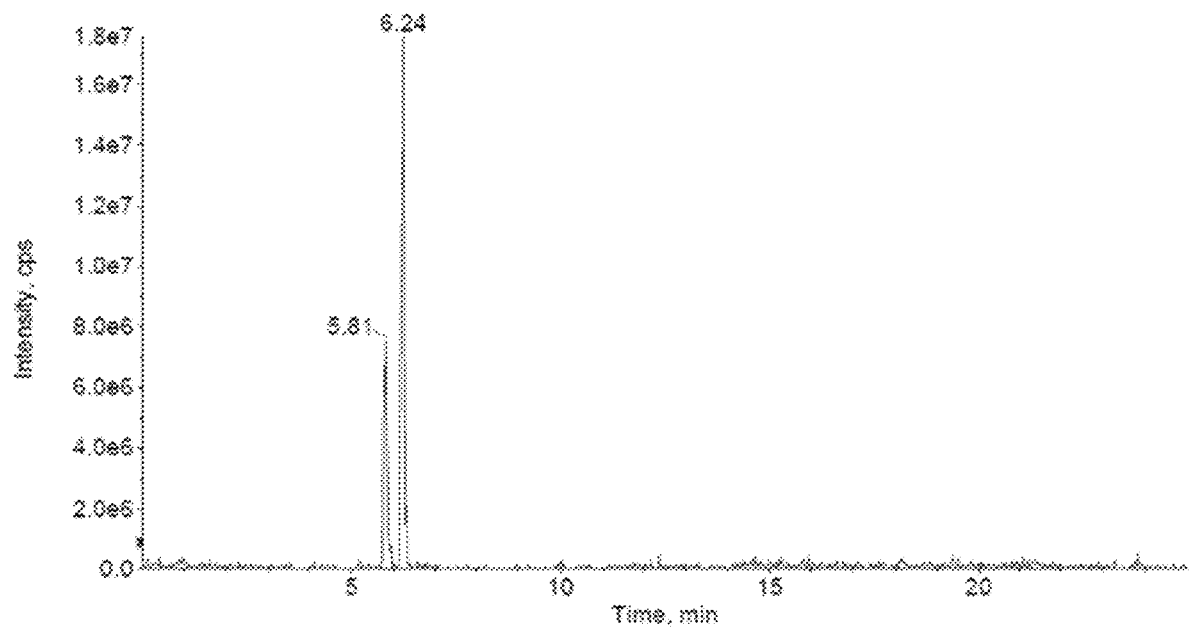
FIG. 24 shows a chromatogram indicating the presence of Glutathione (GSH) in i.p. fluid of orthotopic 4T1 tumor bearing mouse.

FIG. 24. Presence of Glutathione (GSH) in i.p. fluid of orthotopic 4T1 tumor bearing mouse. Chromatogram of m/z=308 on i.p. fluid from 4T1 tumor-bearing mouse, showing a retention peak at 5.8 min, which is the same retention time as for pure GSH (see upper panel of FIG. 21).

FIG. 25. A liver section from a 4T1 tumor mouse imaged using higher gain than in FIG. 2. Scale bar: 50 µm. Representative images from n=3 mice.

FIG. 26. CSPGAKVRC is not selected in phage library screening on cultured CD206− mouse macrophages. A, Cultured RAW 267.4 mouse macrophages were fixed with PFA and stained with rat anti-CD206 (red) and counterstained with DAPI (blue). B, Phage display on RAW 267.4 cells. Cells were lifted using a cell scraper, centrifuged, brought to 4° C. and incubated with 0.5 mL of the same phage library used for the in vivo experiments (0.5 mL of $7 \times 10^{10}$ pfu/mL)+0.5 mL of DMEM, at 4° C. overnight. Cells were then washed four times resuspending in PBS and placing in a new tube every time, lastly the cells were suspended in LB+NP40%, lysed and phage insert were sequenced. The UNO clone is underrepresented in position 2140 of the list (red). Only the top 50 hits from the screen are shown. Scale bar: 50 μm.

Figure 27A:
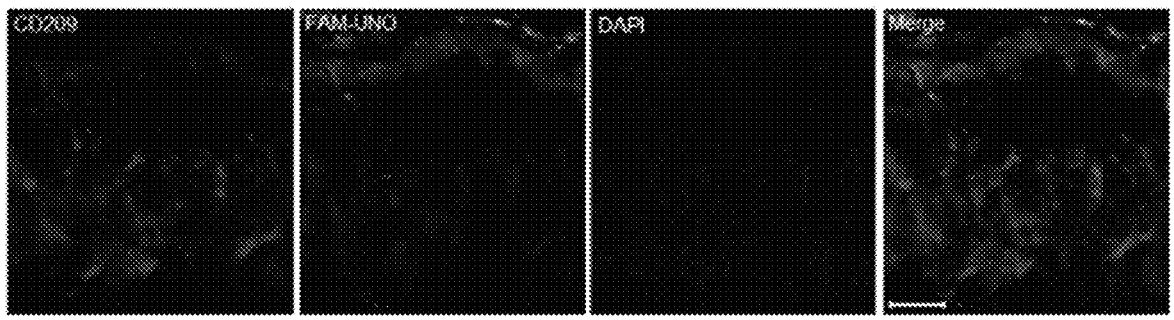
FIG. 27 shows that FAM-UNO does not bind to CD209 using fluorescence imaging of intestinal tissue (FIG. 27A) and 4T1 tumors (FIG. 27B).

FIG. 27. FAM-UNO does not bind to CD209. A, Thirty nmoles of FAM-UNO were injected intravenously in healthy Balb/C mice. Peptide was allowed to circulate for 2 hours. Mice were then sacrificed and intestinal tissue was analyzed by immunofluorescence using rabbit anti-FAM (green) together with rat anti-CD209 (red) and counterstained with DAPI. B, Thirty nmoles of FAM-UNO were injected intravenously in mice bearing 4T1 tumors, 10 days after orthotopic inoculation of $10^6$ Cells. Peptide was let to circulate for two hours, mice were then sacked and tumor and tissues analyzed by immunofluorescence using rabbit Anti-FAM (green) together with rat anti-CD209 (red) and counterstained with DAPI (Blue). Images in A and B were taken using the same imaging conditions. Scale bar: 50 11m (images in B are at the same scale as in A). Representative images from n=3 mice.

Figure 28:
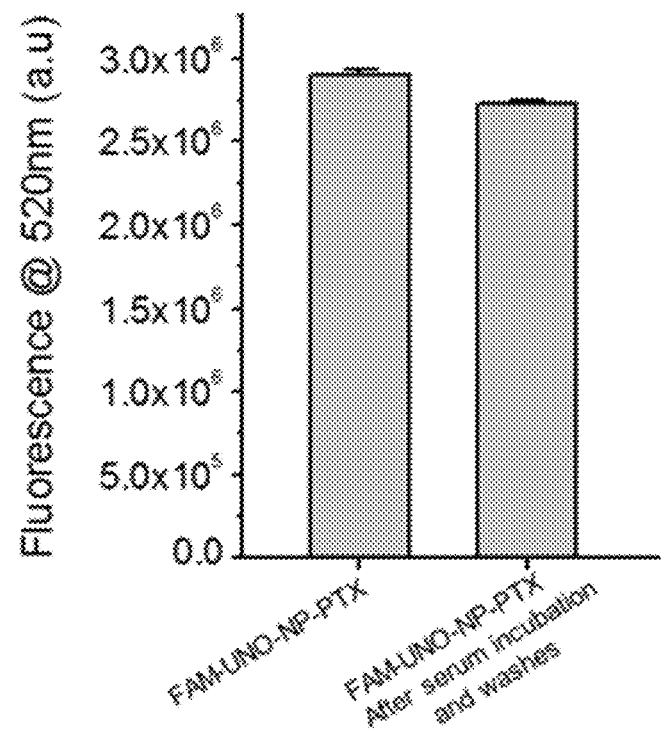
FIG. 28 shows that FAM-UNO does not significantly dissociate from nanoparticles after 6 hours of serum incubation using fluorescence measurements.

FIG. 28. FAM-UNO does not significantly dissociate from nanoparticles after 6 hours of serum incubation. 200 μL of blood were extracted from the tail vein of a mouse bearing orthotopic 4T1 breast tumor (10 days after inoculation of $10^6$ cells) in a blood collection tube and plasma was separated by centrifugation. Later, 150 μL of FAM-UNO-NP-PTX in PBS were mixed with 150 μL of serum and incubated for 6 hours at 37·C with shaking, then particles were washed by 3 centrifugation cycles (21000 g for 30 minutes), and redispersed in 150 μL of PBS to obtain "FAM-UNO-NP-PTX-Serum". Then, 150 μL of the original FAM-UNO-NP-PTX in PBS and 1504 of FAM-UNO-NP-PTX-Serum were placed in a 96 well plate and the fluorescence was measured using a FlexStation 3 Multi-Mode Microplate Reader (Molecular Devices) using 490 nm excitation and collecting at 520 nm. Mean+SEM from three independent experiments FIG. 29. FAM-UNO does not home to healthy lymph nodes. Thirty nmoles of FAM-UNO were injected intravenously in healthy Balb/C female mice. Peptide was allowed to circulate for 2 hours. Mice were then sacrificed, and inguinal lymph node and kidney analyzed by immunofluorescence using rabbit anti-FAM together with rat anti-CD206 (red, 2901) and counterstained with DAPI (blue). FAM-UNO is absent from the healthy inguinal lymph node (left panel), while some CD206 is observed (2901). In the kidney (right panel), the FAM fluorescence signal is detected throughout the tissue. Scale bars: 100 μm. Representative images from n=3 mice.

Figure 30:
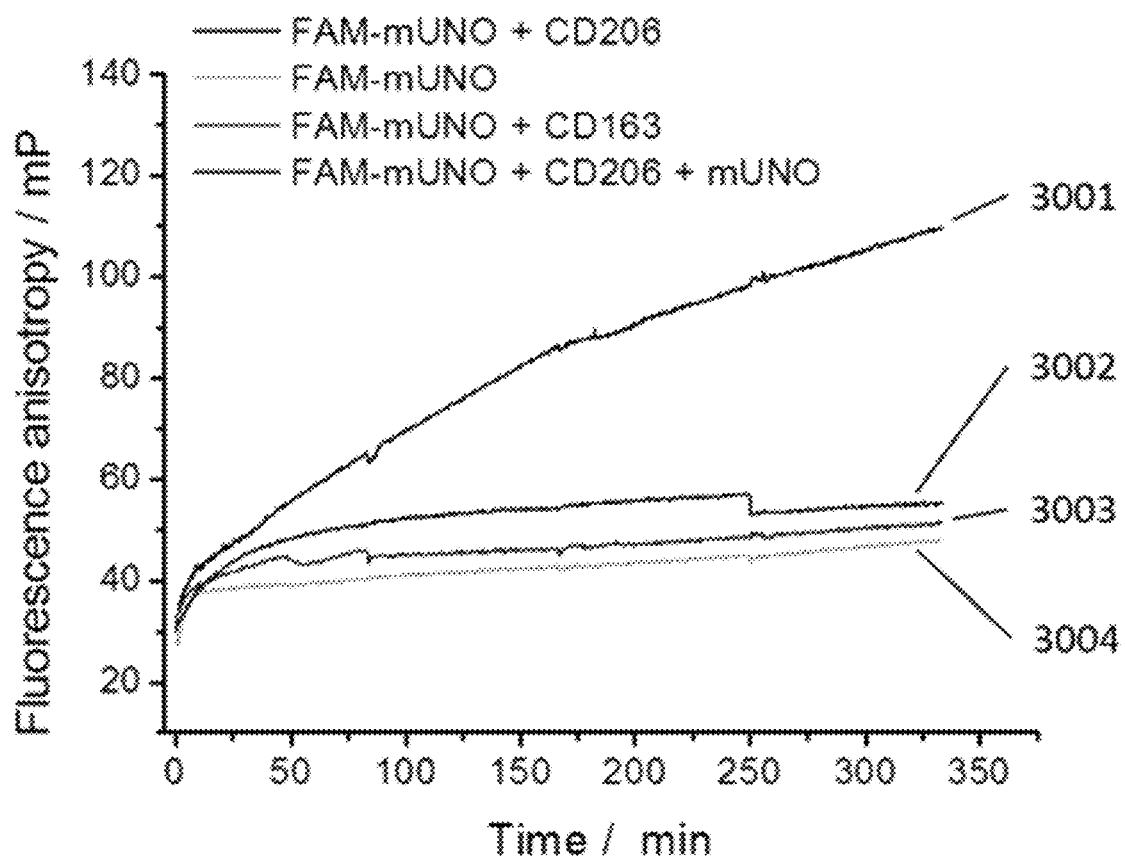
FIG. 30 shows fluorescence anisotropy indicating that mUNO binds to recombinant hCD206.

FIG. 30. mUNO binds to recombinant hCD206. Time course of fluorescence anisotropy of FAM-mUNO during incubation with human recombinant CD206 (black curve, 3001) or with CD163 (red curve, 3003). The concentration of FAM-mUNO was 100 nM and the concentration of CD206 and CD163 was 0.4 μM. The anisotropy for the FAM-mUNO alone is shown in the green curve 3004. Unlabeled mUNO (100 μM) was coincubated with FAM-mUNO and CD206 (blue curve, 3002), indicating that binding of FAM-mUNO was due to the peptidic portion and not the linker or the FAM.

While preferred embodiments have been shown and described herein, it will be obvious to those skilled in the art that such embodiments are provided by way of example only. It should be understood that various alternatives to the embodiments described herein may be employed in practicing the inventions described herein.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1. Experimental Procedures

Materials

Fluorescent peptides were synthesized by using 5(6)-carboxyfluorescein (FAM) with 6-aminohexanoic acid spacer attached to the N-terminus of the peptide. FAM-Cys-UNO used for nanoparticle coupling was synthesized at Sanford Burnham Prebys Medical Discovery Institute. Peptides were synthesized using Fmoc/t-Bu chemistry on a microwave assisted automated peptide synthesizer (Liberty, CEM Corporation, NC, USA). Peptides were purified by HPLC using 0.1% TFA in acetonitrile-water mixtures to 90%-95% purity and validated by Q-TOF mass spectral analysis. All other peptides were purchased from TAG Copenhagen.

Cell Lines and Experimental Animals

Cell lines were purchased from ATCC (VA, USA). The cells were cultivated in DMEM (Lonza, Belgium) containing 100 IU/mL of penicillin, streptomycin, and 10% of heat-inactivated fetal bovine serum (GE Healthcare, UK) in 5% CO2 atmosphere. For animal experimentation athymic nude mice were purchased from HSD (Holland) and Balb/c mice were purchased from Charles River (Wilmington, MA, USA). Animal experimentation protocols were approved by the Estonian Ministry of Agriculture, Committee of Animal Experimentation (Project #42); all methods were performed in accordance with the relevant guidelines and regulations.

In Vivo Phage Display

In vivo phage display was performed according to protocols approved by the Estonian Ministry of Agriculture, Committee of Animal Experimentation (permit #48). Eight-week old Balb/c mice (Charles River, Wilmington, MA, USA) were injected in the mammary fat pad with $10^6$ 4T1 cells in PBS. Ten days later, the 4T1 mouse and a Balb/c female mouse of the matched age, were injected with 5004, of a $7 \times 10^{10}$ pfu/mL of purified CX7C long-circulating library that bears a mutation on the p17 protein of tail fiber[45]. After 2 h the mice were anesthetized and peritoneal cells were collected, washed by centrifugation, and lysed by hand-held homogenizer in 2 mL of LB+NP40 1%. The phage was amplified in *E. coli* strain BLT5403 for high throughput sequencing of peptide encoding segment of the phage genomic DNA using Ion Torrent semiconductor sequencing system.

Extraction and Immunostaining of Peritoneal Cells

For extraction of peritoneal cells, Balb/c mice (healthy and 2 weeks after inoculation of $10^6$ 4T1 cells orthotopically) were anesthetized and intraperitoneally injected with 5 mL of PBS+1% BSA, the abdomen was massaged to detach macrophages and the peritoneal fluid was collected. This procedure typically yielded $5-9 \times 10^6$ cells. The cells were immediately plated on coverslips, let to attach for 2 h, washed with PBS, fixed with PFA for 10 minutes, permeabilized with Triton-X-100 for 10 minutes, and the immunofluorescence protocol was followed, using rat anti-CD206 (Bio-Rad, CA, USA. Product code MCA2235GA) at a 1/100 dilution and anti-rat Alexa Fluor 647 (Invitrogen, CA, USA. Catalog #: A-20991) at a 1/200 dilution.

Phage Biopanning on Raw 267.4 Cells

Mouse macrophage cell line Raw 267.4 (ATCC, VA, USA) was cultured in DMEM with FBS and antibiotics. Cells from a 25 cm² flask (~3×10⁶ cells) were lifted using a cell scraper, centrifuged, brought to 4.0 and incubated with 0.5 mL of the same purified library used for the in vivo experiments (0.5 mL of 7×10¹⁰ pfu/mL)+0.5 mL of DMEM, at 4.0 overnight. Cells were then washed four times by re-suspending in PBS and placing them in a new tube every time, and finally suspended in LB+1% NP40, lysed and subjected to high throughput sequencing.

Peptide Binding on Raw 267.6 Cell Line

Mouse macrophage cell line Raw 267.4 (ATCC, VA, USA) was cultured on coverslips in DMEM containing FBS and antibiotics. Cells were incubated with 0.5 μg/mL of FAM-peptides for 30 minutes at 37·C. Cells were then washed with PBS three times, and three times with PBS-T (PBS-Tween). Cells were then fixed with 4% PFA, permeabilized with Triton-X and stained for CD206 using Rat anti-CD206 (Bio-Rad, CA, USA. Product code MCA2235GA) 1/500 overnight incubation at 4.0 and A647 anti rat 1/1000. Coverslips were mounted and imaged using Zeiss LSM710 Confocal microscope.

Flow Cytometry

Peritoneal cells were extracted from Balb/c mice 2 weeks after inoculation of 10⁶ cells orthotopically). Mice were anesthetized and intraperitoneally injected with 5 mL of PBS+1% BSA, the abdomen was massaged to detach macrophages and the peritoneal fluid was collected. This procedure typically yielded 5-9×10⁶ cells. Cells were concentrated to 1 mL in the same peritoneal fluid. ForFAM-peptide incubation, the peptides were incubated for 30 minutes at 4° C. For antibody incubation the cells were incubated with antibody for 1 h at 4° C. A647 Rat anti-CCR2 (Biolegend, CA, USA. Catalog number 150603) was incubated for 1 h at 4° C. at a dilution of 1/200. FAM-peptides were incubated at a concentration of 0.5 μg/mL, and Rat anti-CD206 (Bio-Rad, CA, USA. Product code MCA2235GA) was incubated at a concentration of 10 μg/mL. Binding of FAM-peptides was monitored with 488 nm channel and CCR2 labeling was assessed in the 647 nm channel using A647 Anti-CCR2 (Biolegend, CA, USA). After incubation of FAM-Peptides or antibodies, the cells were washed 3 times at 4° C. with PBS-T by centrifugation at 250 g for 6 minutes, followed by flow cytometry analysis (Accuri, BD Biosciences, CA, USA).

Tumor Models

Tumor models were induced according to protocols approved by the Estonian Ministry of Agriculture, Committee of Animal Experimentation (permit #48). For the 4T1 breast model, 8-week old female Balb/c mice were injected in the mammary fat pad with 10⁶ cells dispersed in 50 μL of PBS. For homing studies, mice were used 10 days later, when the tumor had reached ~150 mm³. For MCF-7 breast model, 8-week old female nude mice were implanted with an estrogen pellet, and 1 week later inoculated with 5×10⁶ MCF-7 cells in 100 μL of cold Matrigel (BD Biosciences, CA, USA). Mice were used for homing studies three weeks later (tumor volume ~150 mm³). For the metastatic gastric carcinoma, 10⁶ MKN45-P cells in PBS were injected intraperitoneally in 8-week old female nude mice. Mice were used for homing studies two weeks later. For the metastatic melanoma model, 2×10⁵ B16F10 cells were injected intravenously in 1004 of PBS in C57 BL6 mice. The mice were used for homing studies 10 days after. For the angiogenic glioblastoma model, WT-GBM[24], 7×10⁵ cells were stereotactically injected in the right striatum of Fox/Nu mice 2 mm lateral and posterior of bregma of 2.5 mm deep. The mice were used for homing studies 6-7 days after the injection.

Homing Studies and Immunofluorescence

For free peptide homing studies, mice were injected intravenously with 30 nmoles of FAM-peptides in 100 μL of PBS. For nanoparticle homing studies-FAM-UNO-NP-PTX-, mice were injected intravenously in mice bearing MCF-7 breast tumors with 1 mg of Polymer in 100 μL pf PBS and allowed to circulate for 6 h. For tissue collection, the mice were anesthetized and the tissues collected and immediately placed in 4% cold PFA and left overnight at 4·C. Tissues were washed with PBS for 2 h at room temperature and cryoprotected with sucrose 15% at 4·C overnight and then in sucrose 30% at 4.0 overnight. The tumor and the control organs were placed together in the same block with OCT compound (Leica Biosystems, Wetzlar, Germany), snap-frozen in isopentane, and sectioned at 10 μm. FAM was detected using Rabbit anti-FITC (Invitrogen, CA, USA. Catalog #A-889) at a dilution of 1/100 and using Alexa Fluor-546 anti-rabbit antibody (Invitrogen, Ca, USA. Catalog #A-11035) at a dilution of 1/200. CD31 was detected using rat anti-mouse CD31 (BD Biosciences, CA, USA. Catalog #: 553370), TIE2 was detected using rat anti-mouse TIE2 (Biolegend, CA, USA. Catalog #124001), CD209 was detected using rat anti-mouse CD209 (Biolegend, CA, USA. Catalog #147802), HLA ABC was detected using rat anti Human HLA ABC (Bio-Rad, CA, USA. Product code MCA485G), and CD206 was detected using ratanti-mouse CD206 (Bio-Rad, CA, USA. Product code MCA2235GA); using 1/100 primary antibody dilution and Alexa Fluor-647 anti-Rat antibody (Invitrogen, CA, USA. Catalog #21247) at 1/200 dilution. To quantify FAM signal from confocal images, the green channel of images taken by using 20× magnification objective was opened with ImageJ, converted to 8-bit grayscale and the integrated pixel intensity was measured. Different regions of tumors from three different mice were used. These measures were normalized to the number of cells in each image; to count the number of DAPI⁺ cells, the blue channel was opened with ImageJ, converted to 8 bit grayscale, thresholded and cells were counted using the analyze particle tool. The ratio: FAM signal/number of DAPI⁺ cells was graphed and is shown in FIG. 21. The same procedure was used to count the number of CD206⁺ cells.

Nanoparticle Synthesis, Loading and Characterization

Polyethylene glycol-polycaprolactone (PEG(5000)-PCL (10000)) and Maleimide-polyethylene glycol-polycaprolactone (Mal-PEG(5000)-PCL(10000)) were purchased from Advanced Polymer Materials Inc. (Canada). The Mal-PEG (5000)-PCL(10000) copolymer (10 mg, 0.7 μmol) was dissolved in 1 mL of nitrogen-purged dimethylformamide. Two equivalents of FAM-Cys-UNO or FAM-Cys, wherein the cysteine is used for conjugation, were dissolved in 0.5 mL of nitrogen-purged dimethylformamide, and 2 μL of triethylamine were added to the solution. The mixture was mixed overnight at room temperature. The solution was dialyzed against water using a cellulose membrane of 3 KDa MWCO (Thermo Scientific, USA). The resulting suspension was freeze-dried and a yellow powder was obtained. To generate Paclitaxel (PTX) loaded, FAM-UNO or FAM labeled polymersomes, denoted as FAM-UNO-NP-PTX and FAM-NP-PTX respectively: 1 mg of FAM-PEG-PCL or FAM-UNO-PEG-PCL copolymer was mixed with 9 mg of unlabeled PEG-PCL copolymer dissolved in 2 mL of acetone in a glass vial, and 0.75 μmol of PTX dissolved in MeOH were added to the copolymer solution. The solution was then dried under vacuum to allow for the formation of the polymer-drug film. The films were hydrated with 1 mL of PBS (pH 7.4) and sonicated for 2 h. The amount of FAM-labeled peptides in polymersomes was quantified by fluorometry (FlexStation II, Molecular Devices) at 485/520 nm. Dynamic Light Scattering ("DLS"; Zetasizer Nano ZS, Malvern Instruments, USA) was used to assess the polydispersity and average size of the polymersomes. Transmission electron microscopy (TEM) was used to assess the size, surface topology and morphology of assembled vesicles. Briefly, polymersomes dispersed in PBS at pH 7.4 were deposited onto copper grids at 1 mg/mL, stained with 0.75% phosphotungstic acid (pH 7), air-dried, and imaged by TEM (Tecnai 10, Philips, Netherlands). To evaluate stability of FAM-UNO on FAM-UNO-NP-PTX in serum: 200 4 of blood were extracted from the tail vein of a mouse bearing orthotopic 4T1 breast tumor (10 days after inoculation of $10^6$ cells) in a blood collection tube (BD vacutainer, REF: 368494), plasma was separated by centrifugation (300 g for 7 minutes). Later, 150 µL of FAM-UNO-NP-PTX in PBS were mixed with 150 µL of serum and incubated for 6 h at 37·C with shaking, then particles were washed by 3 centrifugation cycles (21000 g for 30 minutes), and redispersed in 150 4 of PBS to obtain "FAM-UNO-NP-PTX-Serum". Then, 150 4 of the original FAM-UNO-NP-PTX in PBS and 150 4 of FAM-UNO-NP-PTX-Serum were placed in a 96 well plate and the fluorescence was measured using a FlexStation 3 Multi-Mode Microplate Reader (Molecular Devices) using 490 nm excitation and collecting at 520 nm.

Fluorescence Anisotropy

The stocks of fluorescent ligands (FAM-UNO, FAM-CSPGAK and FAM-CPMTDNE) in mQ water were stored at −20° C. mMNa-HEPES, 150 mM NaCl, 1 mM CaCl2, 0.1% Pluronic F-127, pH 7.4) on the day of experiment. The concentration of fluorescent ligands was determined by absorbance of FAM ($E495=75000$ $M^{-1}$ $cm^{-1}$).

The recombinant mouse macrophage mannose receptor rmMMR/CD206 (R&D Systems, catalog number: 2535-MM-050) and recombinant mouse CD163 (R&D Systems, catalog number: 7435-CD-050) were reconstituted at 1 mg/ml in IB, aliquoted and stored at −20° C. To generate linearized version of cyclic FAM-UNO peptide, the peptide at 1 mM concentration was preincubated for 24 h at room temperature in a dark place with 3 mM DTT and diluted with IB $2\times10^5$ times before the FA assay. The control experiment with FAM-CPMTDNE peptide (FIG. 22) was performed to rule out the possibility of disulphide bond formation, which could affect the binding properties of linear peptides. Initially, the peptide was preincubated in DMSO for 4 days at room temperature to enhance the disulphide bond formation, and then diluted in IB buffer with 3 mM DTT, and the disappearance of preformed dimer was observed as a change in FA signal.

Fluorescence anisotropy was also carried out using recombinant human macrophage mannose receptor rhMMR/CD206 to determine whether UNO peptide interactions with mouse CD206 carried over to human CD206. The recombinant human macrophage mannose receptor rhMMR/CD206 (R&D Systems, catalog number: 2534-MR-050) and recombinant mouse CD163 (R&D Systems, catalog number: 7435-CD-050) were reconstituted at 1 mg/ml in IB, aliquoted and stored at −20° C. In all experiments, FA signal measurements were done under pseudo first-order conditions with 100 nM singly labelled FAM peptides and 0.4 µM proteins.

In all experiments, FA signal measurements were done under pseudo first-order conditions with 50 nM singly labelled FAM peptides and 1 µM proteins. Black 384-well round bottom polystyrene NBS surface microplates (Corning, Product No. 3676) that were found to give optimal results for our assays (low background of fluorescence and low adsorption of ligands onto plastic surface) were used in all FA experiments. Assays were carried out in kinetic mode in a total volume of 30 µl at 25° C. on the PHERAstar (BMG Labtech, Germany) microplate reader using an optical module with excitation and emission filters of 485 nm (slit 10 nm) and 520 nm (slit 10 nm), respectively. Dual emission detection mode allows simultaneous recording of intensities that are parallel ($\parallel$) and perpendicular ($\perp$) to the plane of excitation light. Sensitivities of channels (G factor) were corrected with gain adjustment of the photomultiplier tubes (PMTs) using fluorescein as a standard. The background fluorescence (receptor and buffer components in the absence of fluorescent ligand) was subtracted independently from all intensity channels. FA signals at time t after initiation of binding reaction was calculated as parameters r(t) from the equation:

$$r(t) = \frac{I(t)_{II} - I(t)_\perp}{I(t)_{II} + 2 \cdot I(t)_\perp}$$

Liquid-Chromatography Mass Spectrometry (LC-MS) Analysis

High-performance liquid chromatography (Agilent 1200 series, USA)—mass spectrometry (SciexQ-Trap 4500, Canada) analysis was done using a C18 column (Kinetex 2.6 µm EVO C18 100×4.6 mm, Phenomenex, USA). Ionization was performed at 300° C. with declustering potential set 30 V. Chromatography gradient started with 2 min 5% acetonitrile in water, followed by linear increase to 95% acetonitrile in 10 min and finally 10 min isocratic flow of 95% acetonitrile in water. Both eluents, water and acetonitrile, contained 0.2% formic acid. Flow rate was 0.3 ml/min. Column temperature was maintained at 40° C. Autosampler temperature was set to 37° C. Retention times and m/z signals of FAM-UNO, were determined from 30 µM FAM-UNO solution in PBS. Tumor lysate was split into two aliquots of 200 µL in each. From one aliquot, 20 µL were injected and the LC-MS profile obtained. The second aliquot was mixed with 50 µL of 30 µM FAM-UNO in PBS and injected within 1 min to LC-MS and the LC-MS profile obtained.

Statistical Analysis

All data represents mean value ±SEM. Significance analysis were done using Statistica 8.0 software, using one-way ANOVA.

Example 2. CSPGAKVRC (SEQ ID NO: 1) Peptide is Enriched in Phage Display Screens on Peritoneal Macrophages in Breast Cancer Mice In vivo phage display was carried out on orthotopic breast cancer bearing mice as outlined in FIG. 1A. Compared to peritoneal cells of healthy mice, CD206+ macrophages were ~5-fold overrepresented in Balb/c mice bearing metastatic syngeneic 4T1 breast tumors (FIG. 1B). We hypothesized that a peptide that binds to peritoneal macrophages in tumor-bearing mice may also target M2-like TAMs. Mice with 4T1 tumors were injected intraperitoneally (i.p.) with a phage library expressing 9-amino acid cyclic CX7C peptides. After 2 h, peritoneal cells were collected, bound phages were rescued by amplification, and the resulting phage pool was subjected to high-throughput sequencing of the peptide-encoding segment of the phage genome. Among the peptide sequences, CSPGAKVRC (SEQ ID NO: 1) was the most highly represented non-truncated peptide (the NNK codons we used to encode the library allow the presence of one stop codon, which results in some truncated peptides). Whereas most peptides showed similar representation in peritoneal cells from the 4T1 tumor-bearing and healthy mice, the phage displaying the sequence CSPGAKVRC (SEQ ID NO: 1) was ~10-fold overrepresented in the peritoneal cells from 4T1 tumor-bearing mice (FIGS. 11C and D). Interestingly, the second most abundant phage clone overrepresented in the cancer mice was CGEKRTRGC (FIG. 1C; SEQ ID NO: 3), a clone that was previously identified together with LyP-1 (CGNKRIRGC; SEQ ID NO: 4), a peptide known to target the p32 protein overexpressed on the surface of TAMs and tumor lymphatic endothelial cells. Interestingly, the GSPGAK motif (SEQ NO: 2) is present in physiological ligands of CD206, a marker of M2-skewed macrophages (Table 2). The CSPGAKVRC peptide (codenamed "UNO"; SEQ ID NO: I) was used for subsequent studies.

TABLE 2

| PDB ID | Name | Length of protein | Position of GSPGAK motif (SEQ ID NO: 2) |
|---|---|---|---|
| Q8IZC6.1 | Collagen alpha-1(XXVII) chain | 1860 | 730-735 |
| P12107.4 | Collagen alpha-1(XI) chain | 1806 | 1480-1485 |
| Q9QZS0.2 | Collagen alpha-3(IV) chain | 1669 | 796-801 |
| P02461.4 | Collagen alpha-1(III) chain | 1466 | 345-350 |
| P02452.5 | Collagen alpha-1(I) chain | 1464 | 1028-1033 |
| P12108.3 | Collagen alpha-2(IX) | 677 | 58-63 |
| P23206.1 | Collagen alpha-1(X) chain | 674 | 317-322 |

Example 3. Systemic FAM-UNO Targets CD206+/TIE2+ Macrophages in Breast Cancer Models To assess in vivo targeting potential of synthetic UNO peptide, the biodistribution of intravenously (i.v.) injected, fluorescently labeled UNO (FAM-UNO), in orthotopic 4T1 tumor-bearing mice was studied and compared with a FAM-labeled control peptide. FAM-UNO accumulated in MEMs in tumors and in sentinel lymph nodes (FIG. 2A-C; arrowheads indicate colocalization of FAM-UNO and CD206 in FIG. 2B). High resolution confocal microscopy, using low optical slice thickness suggested that FAM-UNO was internalized in MEMs (FIG. 7). The MEMs containing FAM-UNO were also positive for angiopoietin receptor TIE2+ (FIG. 2D, II; arrowheads indicate colocalization of FAM-UNO and TIE2 in FIG. 2H). The MEMs were highly abundant in the tumors and the sentinel lymph nodes (FIG. 8), and their distribution correlated with the homing pattern of FAM-UNO. In tumors, 96% of cells positive for FAINT-UNO were also positive for CD206. The signal from FAM-UNO remained readily detectable in the MEMs for up to 12 h after peptide administration (FIG. 9). As a specificity control. 4T1 tumor-bearing mice were injected with a control peptide of the same charge and molecular weight as FAM-UNO, FAM-CRKQGEAKC (FAM-control; SEQ ID NO: 5), and saw no tumor homing (FIG. 2G). The accumulation of FAM-UNO was low in the liver (FIG. 2E), heart, lungs and spleen (FIG. 10). At the 2 h time point, FAM-fluorescence was observed in the kidneys, which are the normal excretion route for peptides (FIG. 2F). The biodistribution of i.v.-injected FAM-UNO in an orthotopic estrogen receptor (ER)-positive xenograft model of breast cancer (MCF-7) was studied. FAM-UNO also selectively accumulated in MEMs in this tumor model (FIG. 11A). The accumulation of FAM-UNO in some CD206⁻ regions (arrowhead in blow-up of FIG. 11A) did not correlate with the presence of HLA ABC+ cells (FIG. 11B), suggesting that FAM-UNO did not target the tumor cells of human origin. Instead, the accumulation of FAM-UNO in such regions was likely due to entrapment of extravasated peptide, as the vessels in these tumors appeared to be leaky as suggested by immunostaining for mouse endogenous IgG (FIG. 11C).

Example 4. FAM-UNO Targets MENU Across a Spectrum of Solid Tumors of Different Origins The applicability of UNO for payload targeting was tested using a spectrum of solid tumor models: orthotopic angiogenic glioblastoma (WT-GBM) 24 generated by stereotactic brain implantation of tumor cells, model of metastatic melanoma (B16F10) generated by intravenous injection of tumor cells, and peritoneal gastric carcinoma (MKN45-P)[25] generated by intraperitoneal injection of tumor cells. Tumor mice were injected i.v. with FAM-UNO; after 2 h the mice were sacrificed, tissues were collected, and cryosections were analyzed by confocal microscopy. In the WT-GBM tumors, the FAM-UNO peptide accumulated in the tumor areas containing MEMs (FIG. 3A; zoomed in panels show colocalization of FAM-UNO and CD206). Intracellular presence of FAM-UNO was also evident in these tumors. The MEMs that internalized FAM-UNO were perivascular (FIG. 12). No signal from FAM-UNO was observed in the normal brain parenchyma (FIG. 13). Even though the blood-brain-barrier is breached in these tumors (FIG. 14), the control peptide did not accumulate in the tumor (FIG. 15A), showing that the tumor homing of LAO is specific and not due to entrapment of the peptide around leaky tumor blood vessels. Systemic FAM-UNO also accumulated in MEMs in a model of peritoneal carcinomatosis, generated by intraperitoneal inoculation of MKN45-P gastric carcinoma cells (FIG. 3B). In this model, FAM-UNO was detected in the periphery of peritoneal tumor nodules, enriched in MEMs (FIG. 16; arrows and circle show colocalization of FAM-UNO and CD206). Whereas some accumulation of control FAM-peptide in MKN45-P tumors was seen in the regions exhibiting higher vascular leakiness (FIG. 15B and FIG. 17), no accumulation was detected in CD206+ cells (FIG. 15B). Finally, FAM-UNO homing to B16F10 melanoma lung metastases was similar to that seen with the other tumors (FIG. 3C and FIG. 15C). For different tumor models, FAM-UNO and CD206 immunoreactivities showed extensive overlap (FIGS. 16 and Is). In contrast, FAM-UNO did not home to non-malignant control tissues, even in the presence of CD206+ macrophages (FIG. 19). These data suggest that UNO targets MEMs in solid tumors independent of the tumor type and location.

Example 5. Linear CSPGAKVRC (SEQ ID NO: 1) and CSPGAK (SEQ ID NO: 6) Bind to CD206

Protein database searches revealed that the GSPGAK motif (SEQ ID NO: 2) is present in collagens type I, III and IV (see Table 2)—all ligands of CD206. In contrast, the motif is absent in type V collagen, which does not bind to CD206. This observation, in combination with the CD206 and FAM-UNO colocalization data, suggested that CD206 might be the target of UNO peptide. Binding of FAM-UNO to mouse recombinant CD206 was studied in a cell-free, solution-based, fluorescence anisotropy (FA) assay. Incubation of FAM-UNO with CD206 did not cause a change in the fluorescence anisotropy (FIG. 4A) indicating the absence of interaction. This suggested that if CD206 is the receptor, perhaps the cyclic peptide gets processed in vivo to yield a CD206 binder. Liquid-chromatography mass spectrometry (LC-MS) analysis showed that upon incubation of FAM-UNO with the 4T1 tumor lysate, the disulfide bridge was reduced to yield a linear peptide "FAM-LinUNO" (FIG. 20). The levels of glutathione, the cofactor of the glutaredoxin involved in reducing disulfides, are known to be elevated in tumors and the reducing capacity in the tumor microenvironment is known to be higher than in healthy tissues. Glutathione presence in tumor lysate was confirmed in the orthotopic 4T1 breast model (FIG. 21). The glutaredoxin system in the tumor microenvironment may contribute to the reduction of the disulfide-bridged FAM-LinUNO observed upon incubation with the tumor lysate. In contrast to FAM-UNO, FAM-LinUNO (obtained by preincubating FAM-UNO with 1,4-dithiothreitol, DTT) did interact with CD206 (FIG. 4A). Since binding to CD206 appeared to require linearity of the peptide, it was hypothesized that the linear CSPGAK (SEQ ID NO: 6) motif—present in UNO and almost identical to GSPGAK (SEQ ID NO: 2)-might contain the minimal CD206-binding motif, and decided to test it in F A assay. Incubation of FAM-CSPGAK (SEQ ID NO: 6) with CD206 caused a clear time-dependent increase of anisotropy, indicating their binding, but there was no change in anisotropy when the peptide was incubated with CD163 (FIG. 4B). The binding of FAM-CSPGAK (SEQ IL) NO: 6) to CD206 was specific, as incubation of CD206 with control peptide FAM-CPMTDNE (SEQ ID NO: 7) did not cause significant changes in anisotropy values (FIG. 4B). The possibility that the control peptide might be dimerized through a disulfide bond (FIG. 22) was excluded, which would eliminate the free sulfhydryl, possibly accounting for the absence of interaction of FAM-CPMTDNE (SEQ ID NO: 7) with CD206. In line with the interaction of FAM-CSPGAK with recombinant CD206, i.v. administered FAM-CSPGAK (SEQ ID NO: 6) accumulated in MEMs in orthotopic 4T1 breast tumor-bearing mice at levels comparable to FAM-UNO (FIG. 23). However, compared to FAM-UNO, the signal from FAM-CSPGAK in non-malignant control tissue that expresses CD206, i.e. liver, was ~7 fold higher.

Figure 27B:
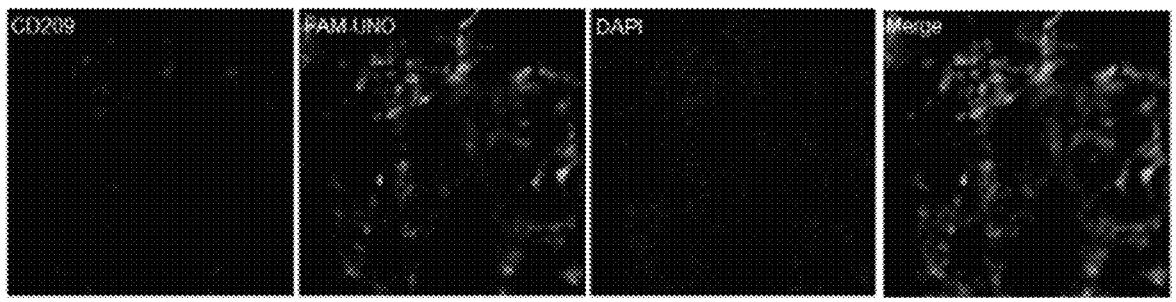

The effect of a blocking anti-CD206 antibody on FAM-UNO binding to peritoneal cells isolated from 4T1 tumor mice was studied. Flow cytometry experiments were performed by incubating FAM-peptide with the cells suspended in the peritoneal fluid; this i.p. fluid also contained glutathione (FIG. 24). Flow cytometry analysis showed that 94% of cells gated for the macrophage marker $CCR2^+$, known to be coexpressed in mouse peritoneal macrophages with CD206, were positive for FAM-UNO binding. Pre-incubation with the anti-CD206 antibody (validated by immunostaining of liver sections, FIG. 25) reduced the binding by 25% (FIG. 4C). In contrast, anti-CD206 antibody had no effect on the cellular binding of FAM-LyP-1 peptide that targets a different receptor, cell surface p32 (FIG. 4D), No UNO-displaying phages were recovered in a phage library screen on $CD206^-$ RAW 267.4 cells (FIG. 26). As an additional indication of homing specificity for FAM-UNO, it was observed that the peptide was not recruited to intestinal tissue of healthy mice, known to express another mannose binding C-type lectin, CD209 (FIG. 27A) and that FAM-UNO showed only a moderate overlap with CD209 in sections from 4T1 tumors (FIG. 27B). Therefore UNO recruitment is unlikely to be mediated by a promiscuous binding of FAM-UNO to the family of mannose-binding lectins. These data established that non-cyclic UNO derivatives interact with CD206 and suggested that conversion of cyclic UNO to linUNO by reducing tumor microenviroment may actuate peptide binding to CD206 in vivo for increased tumor selectivity.

Figure 5B:
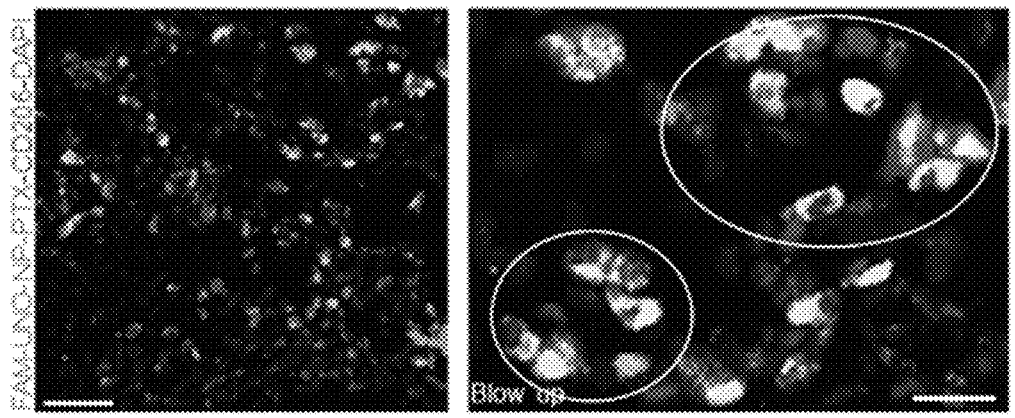
FIG. 5B and FIG. 5C show that FAM-UNO guides cargo-loaded nanoparticles inside MEMs following intravenous injection into mice.
Figure 5C:
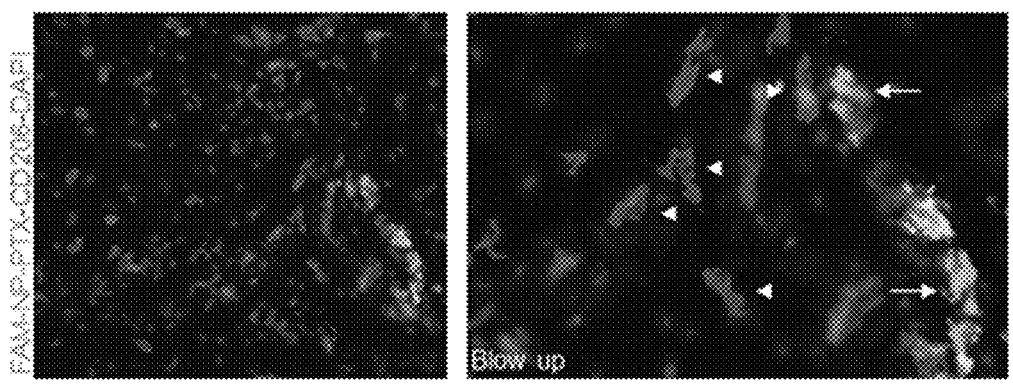
Figure 29:
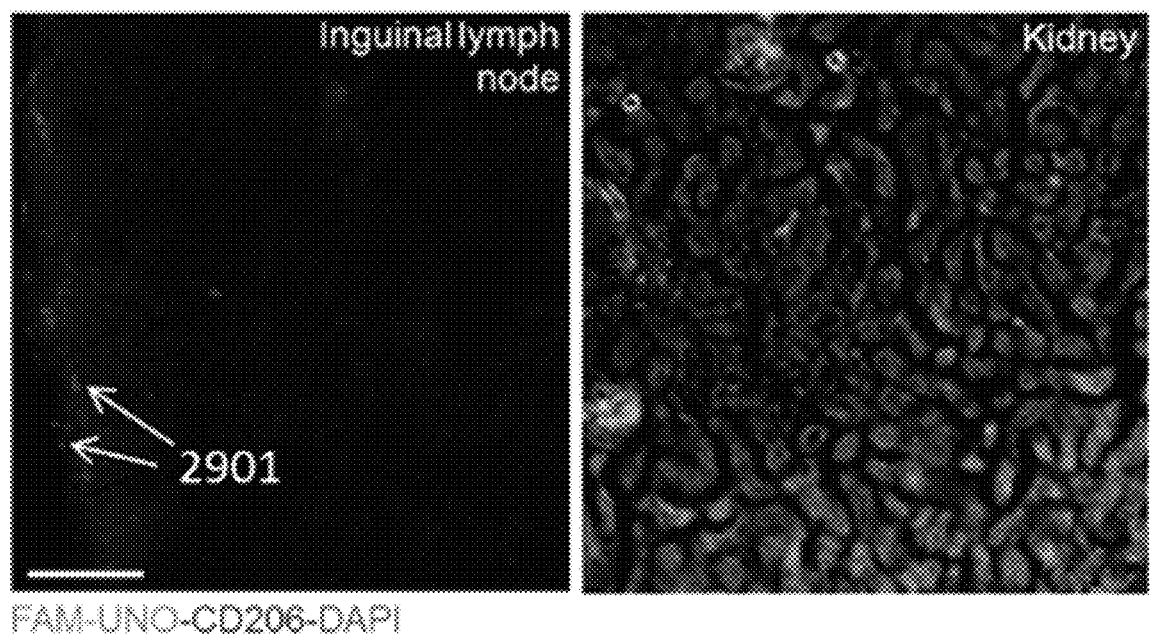
FIG. 29 shows that FAM-UNO does not home to healthy lymph nodes using immunofluorescence.

Example 6. FAM-UNO Guides Cargo to MEMs and is a Potential Sentinel Lymph Node Imaging Agent To assess suitability of UNO for targeting of nanoscale cargo, the peptide was coated on paclitaxel-loaded 120-nm polyethylene glycol-polycaprolactone (PEG-PCL) polymersomes (FIG. 5A). After i.v. injection in orthotopic. MCF-7 breast cancer-bearing mice, the FAM-UNO-derivatized polymersomes loaded with paclitaxel ("FAM-UNO-NP-PTX") accumulated in MEMs (FIG. 5B; circles show areas of colocalization of FAM-UNO and CD206), whereas the non-peptide control particles did not ("FAM-NP-PTX", FIG. 5C; arrows show FAM-NP and arrowheads show CD206). To study whether the FAM-UNO particles are stable, FAM-UNO-NP-PTX was incubated with the sera of 4T1 orthotopic breast tumor mice for 6 h at 37·C, followed by washes and fluorometry at 520 nm (corresponding to FAM). After incubation ~6% of the initial fluorescence was lost (FIG. 28), indicating that the bulk of the peptide remains on the particles and suggesting that the FAM signal observed in the tumors can be attributed to the FAM-UNO-conjugated particles. UNO was evaluated as a guiding module for a contrast agent to image tumor-draining lymph nodes. After administration of FAM-UNO and FAM-LyP-1 to orthotopic 4T1 breast tumor mice, ex vivo quantification of the FAM signal showed a significantly higher accumulation of the FAM in the sentinel lymph node for mice injected with FAM-UNO (FIG. 6). FAM-UNO did not home to the lymph nodes of healthy Balb/C mice (FIG. 29). Some tissues such as the kidney absorb the green fluorescence from the FAM probe; the real measure of FAM accumulation in kidney can be based on the immunodetection of the FAM probe on kidney sections (FIG. 2F). This series of experiments suggested potential applications for UNO-targeted imaging agents for live imaging of tumor-draining lymph nodes.

Example 7. Linear CSPGAKVRC (SEQ ID NO:1) and CSPGAK (SEQ ID NO:6) Bind to Human CD206

Binding of FAM-UNO to human recombinant CD206 was studied in cell-free, solution-based, fluorescence anisotropy (FA) assay. Incubation of FAM-UNO with CD206 did not cause a change in the fluorescence anisotropy. hCD206, when incubated with FAM-mUNO, caused a clear time-dependent increase of anisotropy (FIG. 30, black curve, 3001) indicating their interaction. This increase was not from to the peptide alone as the peptide alone showed a minimal increase (FIG. 30, green curve, 3004). In contrast, FAM-mUNO did not interact with CD163 (FIG. 30, red curve, 3003), as the increase in anisotropy seen in this case was the same as that of the peptide alone. CD163 is another scavenger receptor, which is also a marker of M2-TAMs and also contains a cysteine-rich domain. Furthermore, when hCD206 was pre-incubated with an excess of unlabeled mUNO, a minimal increase of anisotropy was seen from FAM-mUNO (FIG. 30, blue curve, 3002), indicating that the binding of FAM-mUNO to hCD206 is due to the peptide and not the FAM label or the aminohexanoic acid linker.

The examples and embodiments described herein are for illustrative purposes only and various modifications or changes suggested to persons skilled in the art are to be included within the spirit and purview of this application and scope of the appended claims.

SEQUENCE LISTING

```
Sequence total quantity: 78
SEQ ID NO: 1               moltype = AA  length = 9
FEATURE                    Location/Qualifiers
REGION                     1..9
                           note = Synthetic polypeptide
source                     1..9
                           mol_type = protein
                           organism = synthetic construct
SEQUENCE: 1
CSPGAKVRC                                                                  9

SEQ ID NO: 2               moltype = AA  length = 6
FEATURE                    Location/Qualifiers
REGION                     1..6
                           note = Synthetic polypeptide
source                     1..6
                           mol_type = protein
                           organism = synthetic construct
SEQUENCE: 2
GSPGAK                                                                     6

SEQ ID NO: 3               moltype = AA  length = 9
FEATURE                    Location/Qualifiers
REGION                     1..9
                           note = Synthetic polypeptide
source                     1..9
                           mol_type = protein
                           organism = synthetic construct
SEQUENCE: 3
CGEKRTRGC                                                                  9

SEQ ID NO: 4               moltype = AA  length = 9
FEATURE                    Location/Qualifiers
REGION                     1..9
                           note = Synthetic polypeptide
source                     1..9
                           mol_type = protein
                           organism = synthetic construct
SEQUENCE: 4
CGNKRTRGC                                                                  9

SEQ ID NO: 5               moltype = AA  length = 9
FEATURE                    Location/Qualifiers
REGION                     1..9
                           note = Synthetic polypeptide
source                     1..9
                           mol_type = protein
                           organism = synthetic construct
SEQUENCE: 5
CRKQGEAKC                                                                  9

SEQ ID NO: 6               moltype = AA  length = 6
FEATURE                    Location/Qualifiers
REGION                     1..6
                           note = Synthetic polypeptide
source                     1..6
                           mol_type = protein
                           organism = synthetic construct
SEQUENCE: 6
CSPGAK                                                                     6

SEQ ID NO: 7               moltype = AA  length = 7
FEATURE                    Location/Qualifiers
REGION                     1..7
                           note = Synthetic polypeptide
source                     1..7
                           mol_type = protein
                           organism = synthetic construct
SEQUENCE: 7
CPMTDNE                                                                    7

SEQ ID NO: 8               moltype = AA  length = 9
FEATURE                    Location/Qualifiers
REGION                     1..9
                           note = Synthetic polypeptide
source                     1..9
                           mol_type = protein
                           organism = synthetic construct
```

```
SEQUENCE: 8
CDSRSRKRC                                                                        9

SEQ ID NO: 9              moltype = AA  length = 9
FEATURE                   Location/Qualifiers
REGION                    1..9
                          note = Synthetic polypeptide
source                    1..9
                          mol_type = protein
                          organism = synthetic construct
SEQUENCE: 9
CPKGAGSKC                                                                        9

SEQ ID NO: 10             moltype = AA  length = 9
FEATURE                   Location/Qualifiers
REGION                    1..9
                          note = Synthetic polypeptide
source                    1..9
                          mol_type = protein
                          organism = synthetic construct
SEQUENCE: 10
CRKGTLGRC                                                                        9

SEQ ID NO: 11             moltype = AA  length = 9
FEATURE                   Location/Qualifiers
REGION                    1..9
                          note = Synthetic polypeptide
source                    1..9
                          mol_type = protein
                          organism = synthetic construct
SEQUENCE: 11
CVKGTVKTC                                                                        9

SEQ ID NO: 12             moltype = AA  length = 9
FEATURE                   Location/Qualifiers
REGION                    1..9
                          note = Synthetic polypeptide
source                    1..9
                          mol_type = protein
                          organism = synthetic construct
SEQUENCE: 12
CRGTIRGRC                                                                        9

SEQ ID NO: 13             moltype = AA  length = 9
FEATURE                   Location/Qualifiers
REGION                    1..9
                          note = Synthetic polypeptide
source                    1..9
                          mol_type = protein
                          organism = synthetic construct
SEQUENCE: 13
CLDRRKKPC                                                                        9

SEQ ID NO: 14             moltype = AA  length = 9
FEATURE                   Location/Qualifiers
REGION                    1..9
                          note = Synthetic polypeptide
source                    1..9
                          mol_type = protein
                          organism = synthetic construct
SEQUENCE: 14
CPARRSNRC                                                                        9

SEQ ID NO: 15             moltype = AA  length = 9
FEATURE                   Location/Qualifiers
REGION                    1..9
                          note = Synthetic polypeptide
source                    1..9
                          mol_type = protein
                          organism = synthetic construct
SEQUENCE: 15
CKDSAEMRC                                                                        9

SEQ ID NO: 16             moltype = AA  length = 9
FEATURE                   Location/Qualifiers
REGION                    1..9
                          note = Synthetic polypeptide
source                    1..9
                          mol_type = protein
```

```
                              -continued

SEQUENCE: 16
CERSNNVSC                                                                9

SEQ ID NO: 17           moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 17
CGKRAPFRC                                                                9

SEQ ID NO: 18           moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 18
CVSSSSGRC                                                                9

SEQ ID NO: 19           moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 19
CTVAGSGPC                                                                9

SEQ ID NO: 20           moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 20
CIGNSKKKC                                                                9

SEQ ID NO: 21           moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 21
CVRLREKRC                                                                9

SEQ ID NO: 22           moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 22
CRKKSRAQC                                                                9

SEQ ID NO: 23           moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 23
CAANDYSDC                                                                9

SEQ ID NO: 24           moltype = AA   length = 9
FEATURE                 Location/Qualifiers
REGION                  1..9
                        note = Synthetic polypeptide
source                  1..9
```

```
                         mol_type = protein
                         organism = synthetic construct
SEQUENCE: 24
CLEDDSAKC                                                                            9

SEQ ID NO: 25            moltype = AA  length = 5
FEATURE                  Location/Qualifiers
REGION                   1..5
                         note = Synthetic polypeptide
source                   1..5
                         mol_type = protein
                         organism = synthetic construct
SEQUENCE: 25
CNDKS                                                                                5

SEQ ID NO: 26            moltype = AA  length = 9
FEATURE                  Location/Qualifiers
REGION                   1..9
                         note = Synthetic polypeptide
source                   1..9
                         mol_type = protein
                         organism = synthetic construct
SEQUENCE: 26
CVGRKVRGC                                                                            9

SEQ ID NO: 27            moltype = AA  length = 9
FEATURE                  Location/Qualifiers
REGION                   1..9
                         note = Synthetic polypeptide
source                   1..9
                         mol_type = protein
                         organism = synthetic construct
SEQUENCE: 27
CVDRRESRC                                                                            9

SEQ ID NO: 28            moltype = AA  length = 9
FEATURE                  Location/Qualifiers
REGION                   1..9
                         note = Synthetic polypeptide
source                   1..9
                         mol_type = protein
                         organism = synthetic construct
SEQUENCE: 28
CRQEEESRC                                                                            9

SEQ ID NO: 29            moltype = AA  length = 9
FEATURE                  Location/Qualifiers
REGION                   1..9
                         note = Synthetic polypeptide
source                   1..9
                         mol_type = protein
                         organism = synthetic construct
SEQUENCE: 29
CGKTRYSRC                                                                            9

SEQ ID NO: 30            moltype = AA  length = 8
FEATURE                  Location/Qualifiers
REGION                   1..8
                         note = Synthetic polypeptide
source                   1..8
                         mol_type = protein
                         organism = synthetic construct
SEQUENCE: 30
CIGVSSDC                                                                             8

SEQ ID NO: 31            moltype = AA  length = 9
FEATURE                  Location/Qualifiers
REGION                   1..9
                         note = Synthetic polypeptide
source                   1..9
                         mol_type = protein
                         organism = synthetic construct
SEQUENCE: 31
CRTLRSKAC                                                                            9

SEQ ID NO: 32            moltype = AA  length = 9
FEATURE                  Location/Qualifiers
REGION                   1..9
                         note = Synthetic polypeptide
```

```
source                      1..9
                            mol_type = protein
                            organism = synthetic construct
SEQUENCE: 32
CRRTRQRSC                                                                     9

SEQ ID NO: 33               moltype = AA  length = 5
FEATURE                     Location/Qualifiers
REGION                      1..5
                            note = Synthetic polypeptide
source                      1..5
                            mol_type = protein
                            organism = synthetic construct
SEQUENCE: 33
CIGNK                                                                         5

SEQ ID NO: 34               moltype = AA  length = 9
FEATURE                     Location/Qualifiers
REGION                      1..9
                            note = Synthetic polypeptide
source                      1..9
                            mol_type = protein
                            organism = synthetic construct
SEQUENCE: 34
CVLNESGDC                                                                     9

SEQ ID NO: 35               moltype = AA  length = 9
FEATURE                     Location/Qualifiers
REGION                      1..9
                            note = Synthetic polypeptide
source                      1..9
                            mol_type = protein
                            organism = synthetic construct
SEQUENCE: 35
CRDKRGSKC                                                                     9

SEQ ID NO: 36               moltype = AA  length = 9
FEATURE                     Location/Qualifiers
REGION                      1..9
                            note = Synthetic polypeptide
source                      1..9
                            mol_type = protein
                            organism = synthetic construct
SEQUENCE: 36
CKRPNENVC                                                                     9

SEQ ID NO: 37               moltype = AA  length = 9
FEATURE                     Location/Qualifiers
REGION                      1..9
                            note = Synthetic polypeptide
source                      1..9
                            mol_type = protein
                            organism = synthetic construct
SEQUENCE: 37
CNRRTKIGC                                                                     9

SEQ ID NO: 38               moltype = AA  length = 9
FEATURE                     Location/Qualifiers
REGION                      1..9
                            note = Synthetic polypeptide
source                      1..9
                            mol_type = protein
                            organism = synthetic construct
SEQUENCE: 38
CSPKMRATC                                                                     9

SEQ ID NO: 39               moltype = AA  length = 9
FEATURE                     Location/Qualifiers
REGION                      1..9
                            note = Synthetic polypeptide
source                      1..9
                            mol_type = protein
                            organism = synthetic construct
SEQUENCE: 39
CKRTRRREC                                                                     9

SEQ ID NO: 40               moltype = AA  length = 9
FEATURE                     Location/Qualifiers
REGION                      1..9
```

```
                          note = Synthetic polypeptide
source                    1..9
                          mol_type = protein
                          organism = synthetic construct
SEQUENCE: 40
CLSSITPEC                                                                    9

SEQ ID NO: 41             moltype = AA  length = 7
FEATURE                   Location/Qualifiers
REGION                    1..7
                          note = Synthetic polypeptide
source                    1..7
                          mol_type = protein
                          organism = synthetic construct
SEQUENCE: 41
CVDQDPL                                                                      7

SEQ ID NO: 42             moltype = AA  length = 9
FEATURE                   Location/Qualifiers
REGION                    1..9
                          note = Synthetic polypeptide
source                    1..9
                          mol_type = protein
                          organism = synthetic construct
SEQUENCE: 42
CRGTRSNRC                                                                    9

SEQ ID NO: 43             moltype = AA  length = 9
FEATURE                   Location/Qualifiers
REGION                    1..9
                          note = Synthetic polypeptide
source                    1..9
                          mol_type = protein
                          organism = synthetic construct
SEQUENCE: 43
CGPCQEGLC                                                                    9

SEQ ID NO: 44             moltype = AA  length = 9
FEATURE                   Location/Qualifiers
REGION                    1..9
                          note = Synthetic polypeptide
source                    1..9
                          mol_type = protein
                          organism = synthetic construct
SEQUENCE: 44
CMTLRSRKC                                                                    9

SEQ ID NO: 45             moltype = AA  length = 9
FEATURE                   Location/Qualifiers
REGION                    1..9
                          note = Synthetic polypeptide
source                    1..9
                          mol_type = protein
                          organism = synthetic construct
SEQUENCE: 45
CSTKTSLKC                                                                    9

SEQ ID NO: 46             moltype = AA  length = 5
FEATURE                   Location/Qualifiers
REGION                    1..5
                          note = Synthetic polypeptide
source                    1..5
                          mol_type = protein
                          organism = synthetic construct
SEQUENCE: 46
CGDEA                                                                        5

SEQ ID NO: 47             moltype = AA  length = 9
FEATURE                   Location/Qualifiers
REGION                    1..9
                          note = Synthetic polypeptide
source                    1..9
                          mol_type = protein
                          organism = synthetic construct
SEQUENCE: 47
CTTSTGADC                                                                    9

SEQ ID NO: 48             moltype = AA  length = 9
FEATURE                   Location/Qualifiers
```

```
                        -continued

REGION                  1..9
                        note = Synthetic polypeptide
source                  1..9
                        mol_type = protein
                        organism = synthetic construct
SEQUENCE: 48
CSTLKRRVC                                                             9

SEQ ID NO: 49           moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 49
CRGVAKVRC                                                             9

SEQ ID NO: 50           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 50
CSVGRLK                                                               7

SEQ ID NO: 51           moltype = AA  length = 5
FEATURE                 Location/Qualifiers
REGION                  1..5
                        note = Synthetic polypeptide
source                  1..5
                        mol_type = protein
                        organism = synthetic construct
SEQUENCE: 51
CHQDF                                                                 5

SEQ ID NO: 52           moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 52
CSFDEANPC                                                             9

SEQ ID NO: 53           moltype = AA  length = 5
FEATURE                 Location/Qualifiers
REGION                  1..5
                        note = Synthetic polypeptide
source                  1..5
                        mol_type = protein
                        organism = synthetic construct
SEQUENCE: 53
CRNRA                                                                 5

SEQ ID NO: 54           moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 54
CVSDRKVAC                                                             9

SEQ ID NO: 55           moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 55
CKRGRFAKL                                                             9

SEQ ID NO: 56           moltype = AA  length = 7
```

```
FEATURE                 Location/Qualifiers
REGION                  1..7
                        note = Synthetic polypeptide
source                  1..7
                        mol_type = protein
                        organism = synthetic construct
SEQUENCE: 56
CAQPNSR                                                                           7

SEQ ID NO: 57           moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 57
CRPTRRVSC                                                                         9

SEQ ID NO: 58           moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 58
CRNGLNKRC                                                                         9

SEQ ID NO: 59           moltype = AA  length = 6
FEATURE                 Location/Qualifiers
REGION                  1..6
                        note = Synthetic polypeptide
source                  1..6
                        mol_type = protein
                        organism = synthetic construct
SEQUENCE: 59
CGFRSD                                                                            6

SEQ ID NO: 60           moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 60
CRKTVGPRC                                                                         9

SEQ ID NO: 61           moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 61
CEVMQRKRC                                                                         9

SEQ ID NO: 62           moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 62
CVASVKRKC                                                                         9

SEQ ID NO: 63           moltype = AA  length = 5
FEATURE                 Location/Qualifiers
REGION                  1..5
                        note = Synthetic polypeptide
source                  1..5
                        mol_type = protein
                        organism = synthetic construct
SEQUENCE: 63
CDANQ                                                                             5
```

| | | |
|---|---|---|
| SEQ ID NO: 64<br>FEATURE<br>REGION<br><br>source<br><br><br><br>SEQUENCE: 64<br>CRRTAIKKC | moltype = AA   length = 9<br>Location/Qualifiers<br>1..9<br>note = Synthetic polypeptide<br>1..9<br>mol_type = protein<br>organism = synthetic construct<br><br> | <br><br><br><br><br><br><br><br><br>9 |
| SEQ ID NO: 65<br>FEATURE<br>REGION<br><br>source<br><br><br><br>SEQUENCE: 65<br>CLSKRTPRC | moltype = AA   length = 9<br>Location/Qualifiers<br>1..9<br>note = Synthetic polypeptide<br>1..9<br>mol_type = protein<br>organism = synthetic construct<br><br> | <br><br><br><br><br><br><br><br><br>9 |
| SEQ ID NO: 66<br>FEATURE<br>REGION<br><br>source<br><br><br><br>SEQUENCE: 66<br>CVDSEATDC | moltype = AA   length = 9<br>Location/Qualifiers<br>1..9<br>note = Synthetic polypeptide<br>1..9<br>mol_type = protein<br>organism = synthetic construct<br><br> | <br><br><br><br><br><br><br><br><br>9 |
| SEQ ID NO: 67<br>FEATURE<br>REGION<br><br>source<br><br><br><br>SEQUENCE: 67<br>CPRTAKVLC | moltype = AA   length = 9<br>Location/Qualifiers<br>1..9<br>note = Synthetic polypeptide<br>1..9<br>mol_type = protein<br>organism = synthetic construct<br><br> | <br><br><br><br><br><br><br><br><br>9 |
| SEQ ID NO: 68<br>FEATURE<br>REGION<br><br>source<br><br><br><br>SEQUENCE: 68<br>CQSRSPRNC | moltype = AA   length = 9<br>Location/Qualifiers<br>1..9<br>note = Synthetic polypeptide<br>1..9<br>mol_type = protein<br>organism = synthetic construct<br><br> | <br><br><br><br><br><br><br><br><br>9 |
| SEQ ID NO: 69<br>FEATURE<br>REGION<br><br>source<br><br><br><br>SEQUENCE: 69<br>CNKNGTAPC | moltype = AA   length = 9<br>Location/Qualifiers<br>1..9<br>note = Synthetic polypeptide<br>1..9<br>mol_type = protein<br>organism = synthetic construct<br><br> | <br><br><br><br><br><br><br><br><br>9 |
| SEQ ID NO: 70<br>FEATURE<br>REGION<br><br>source<br><br><br><br>SEQUENCE: 70<br>CTDRHSTNC | moltype = AA   length = 9<br>Location/Qualifiers<br>1..9<br>note = Synthetic polypeptide<br>1..9<br>mol_type = protein<br>organism = synthetic construct<br><br> | <br><br><br><br><br><br><br><br><br>9 |
| SEQ ID NO: 71<br>FEATURE<br>REGION<br><br>source<br><br><br><br>SEQUENCE: 71<br>CDALAPNSC | moltype = AA   length = 9<br>Location/Qualifiers<br>1..9<br>note = Synthetic polypeptide<br>1..9<br>mol_type = protein<br>organism = synthetic construct<br><br> | <br><br><br><br><br><br><br><br><br>9 |

```
SEQ ID NO: 72            moltype = AA   length = 9
FEATURE                  Location/Qualifiers
REGION                   1..9
                         note = Synthetic polypeptide
source                   1..9
                         mol_type = protein
                         organism = synthetic construct
SEQUENCE: 72
CIDGRTDLC                                                                   9

SEQ ID NO: 73            moltype = AA   length = 9
FEATURE                  Location/Qualifiers
REGION                   1..9
                         note = Synthetic polypeptide
source                   1..9
                         mol_type = protein
                         organism = synthetic construct
SEQUENCE: 73
CMNVESSPC                                                                   9

SEQ ID NO: 74            moltype = AA   length = 9
FEATURE                  Location/Qualifiers
REGION                   1..9
                         note = Synthetic polypeptide
source                   1..9
                         mol_type = protein
                         organism = synthetic construct
SEQUENCE: 74
CREKNSQRC                                                                   9

SEQ ID NO: 75            moltype = AA   length = 9
FEATURE                  Location/Qualifiers
REGION                   1..9
                         note = Synthetic polypeptide
source                   1..9
                         mol_type = protein
                         organism = synthetic construct
SEQUENCE: 75
CLVRPERKC                                                                   9

SEQ ID NO: 76            moltype = AA   length = 9
FEATURE                  Location/Qualifiers
REGION                   1..9
                         note = Synthetic polypeptide
source                   1..9
                         mol_type = protein
                         organism = synthetic construct
SEQUENCE: 76
CRKRMNRTC                                                                   9

SEQ ID NO: 77            moltype = AA   length = 9
FEATURE                  Location/Qualifiers
REGION                   1..9
                         note = Synthetic polypeptide
source                   1..9
                         mol_type = protein
                         organism = synthetic construct
SEQUENCE: 77
CVDITSPDC                                                                   9

SEQ ID NO: 78            moltype = AA   length = 9
FEATURE                  Location/Qualifiers
REGION                   1..9
                         note = Synthetic polypeptide
source                   1..9
                         mol_type = protein
                         organism = synthetic construct
SEQUENCE: 78
CSYEKEPVC                                                                   9
```

What is claimed is:

1. A method for directing a moiety to a MRC1-expressing tumor associated macrophage in a subject, comprising administering to the subject a composition comprising the moiety linked to an isolated peptide having a length of no more than 50 amino acid residues, comprising an amino acid sequence Cys-Ser-Pro-Gly-Ala-Lys (SEQ ID NO: 6), wherein the isolated peptide binds to a multi-ligand endocytic receptor mannose receptor (MRC1) expressed on a macrophage.

2. The method of claim 1, wherein the amino acid sequence further comprises Cys-Ser-Pro-Gly-Ala-Lys-Val-Arg-Cys (SEQ ID NO: 1).

3. The method of claim 1, wherein the macrophage is a tumor-associated macrophage.

4. The method of claim 1, wherein the macrophage is located within a tissue comprising a tumor.

5. The method of claim 4, wherein the tumor is a solid tumor.

6. The method of claim 1, wherein the isolated peptide is linked to a detectable agent.

7. The method of claim 6, wherein the detectable agent is a fluorescent molecule or a radionuclide.

8. The method of claim 7, where in the detectable agent is Feridex, a tantalum compound, iodine, radioactive iodine, an organic iodo acid, iron oxide, gadolinium, an enzyme, biotin, a metal, barium sulfate, diatrizoic acid sodium salt dehydrate, Lissamine Rhodamine PE, Rhodamine, a radioisotope, a ferromagnetic compound, a paramagnetic compound, a diamagnetic compound, indium-111, technetium-99, carbon-11, carbon-13, or any combination thereof.

9. The method of claim 1, wherein the isolated peptide is linked to a nanoparticle.

10. The isolated peptide of claim 9, wherein the nanoparticle is a liposome.

11. The isolated peptide of claim 9, wherein the nanoparticle is a polymersome.

12. The method of claim 11, wherein the polymersome comprises polyethylene glycol-polycaprolactone.

13. The method of claim 9, wherein the nanoparticle comprises a therapeutic agent.

14. The isolated peptide of claim 13, where the nanoparticle encapsulates the therapeutic agent.

15. The method of claim 1, wherein the isolated peptide further comprises a therapeutic agent linked to the isolated peptide.

16. The method of claim 15, wherein the therapeutic agent is a therapeutic protein, a therapeutic compound, a therapeutic composition, a chemotherapeutic agent, a cancer chemotherapeutic agent, a radiopharmaceutical, a toxin, a cytotoxic agent, Abraxane, paclitaxel, taxol, imatinib, a virus, a nucleic acid molecule, an antibody, a small interfering RNA, a microRNA, a polypeptide, a peptide, an anti-angiogenic agent, a pro-angiogenic agent, an anti-inflammatory agent, a TGF-β inhibitor, a β-2 agonist, an endothelin (ET-1) receptor antagonist, interferon-a and tasquinimod, or any combination thereof.

17. The method of claim 1, wherein the isolated peptide is a cyclic peptide.

18. The method of claim 1, wherein the isolated peptide is a peptide is linear.

19. The method of claim 1, wherein the isolated peptide is a modified peptide.

* * * * *